US012600785B2

(12) United States Patent
Pan et al.

(10) Patent No.: US 12,600,785 B2
(45) Date of Patent: Apr. 14, 2026

(54) METHOD OF SCREENING FOR COMPOUNDS THAT INHIBIT PROLIFERATION OF PANCREATIC CANCER CELLS HAVING A LOSS-OF-FUNCTION MUTATION IN THE RNF43 GENE

(71) Applicant: ANTLERA THERAPEUTICS INC., Foster City, CA (US)

(72) Inventors: Guohua Pan, Oakville (CA); Jason Moffat, Toronto (CA); Sachdev Sidhu, Toronto (CA); Stephane Angers, Mississauga (CA); Zachary Steinhart, Toronto (CA); Xiaowei Wang, Toronto (CA)

(73) Assignee: Antlera Therapeutics Inc., Foster City, CA (US)

( * ) Notice: Subject to any disclaimer, the term of this patent is extended or adjusted under 35 U.S.C. 154(b) by 326 days.

(21) Appl. No.: 17/176,155

(22) Filed: Feb. 15, 2021

(65) Prior Publication Data

US 2021/0253718 A1     Aug. 19, 2021

Related U.S. Application Data

(63) Continuation of application No. 16/073,198, filed as application No. PCT/CA2017/050090 on Jan. 27, 2017, now Pat. No. 10,919,968.

(60) Provisional application No. 62/289,012, filed on Jan. 29, 2016.

(51) Int. Cl.
| | |
|---|---|
| *A61P 35/00* | (2006.01) |
| *A61K 47/68* | (2017.01) |
| *C07K 16/28* | (2006.01) |
| *G01N 33/574* | (2006.01) |
| *A61K 39/00* | (2006.01) |

(52) U.S. Cl.
CPC ...... *C07K 16/2863* (2013.01); *A61K 47/6849* (2017.08); *A61K 47/6851* (2017.08); *A61P 35/00* (2018.01); *G01N 33/574* (2013.01); *A61K 2039/505* (2013.01); *C07K 2317/21* (2013.01); *C07K 2317/52* (2013.01); *C07K 2317/55* (2013.01); *C07K 2317/56* (2013.01); *C07K 2317/565* (2013.01); *C07K 2317/567* (2013.01); *C07K 2317/73* (2013.01); *C07K 2317/76* (2013.01); *C07K 2317/92* (2013.01); *G01N 2333/726* (2013.01); *G01N 2800/7028* (2013.01)

(58) Field of Classification Search
CPC ............ C07K 16/2863; A61K 47/6849; A61K 2039/505
See application file for complete search history.

(56) References Cited

U.S. PATENT DOCUMENTS

| | | | | |
|---|---|---|---|---|
| 6,403,325 B1 * | 6/2002 | Kosik | ................ | G01N 33/6896 435/7.1 |
| 8,158,761 B2 * | 4/2012 | Wands | ............... | G01N 33/5067 530/388.1 |
| 8,551,789 B2 * | 10/2013 | Gurney | .................. | C07K 16/28 435/7.1 |

FOREIGN PATENT DOCUMENTS

| | | | | |
|---|---|---|---|---|
| WO | WO2014066328 | * | 5/2014 | ........... A61K 39/395 |
| WO | 2014121196 A1 | | 8/2014 | |
| WO | 2015023851 A1 | | 2/2015 | |

OTHER PUBLICATIONS

Carmon et al. Development of a bioassay for detection of Wnt-binding affinities for individual frizzled receptors. Anal. Biochem. 401, 288-294, 2010. (Year: 2010).*
Carmon et al. Wnt7a interaction with Fzd5 and detection of signaling activation using a split eGFP. Biochem. Biophys. Res. Commun.368, 285-291, 2008. (Year: 2008).*
Karlin and Altschul, 1990, Proc. Natl. Acad. Sci. U.S.A. 87:2264-2268.
Karlin and Altschul, 1993, Proc. Natl. Acad. Sci. U.S.A. 90:5873-5877.
Kinde I, et al. (2013) Sci Transl Med 5(167):167ra4).
Kohler and Milstein, Nature, 256:495 (1975).
Koo BK, et al. (2012) . Nature 488(7413):665-669.
Kostelny SA et al, J Immunol. Mar. 1, 1992;148(5):1547-53.
Kozbor, et al. 1983 Immunol Today 4:72.
Lam KS, Anticancer Drug Des. Apr. 1997;12(3):145-67.
Lefranc et al., 2003. Development and Comparative Immunology 27:55-77.
Lipi et al. 2015 RNA Biology 12 : 1232-1245.
Liu et al., 2016. Oncotarget 7:49130.
Madan and Virshup, 2015. Mol Cancer Ther 14:1087-1094.
Malmqvist, Nature 361:186-87 (1993).
McEnaney et al, 2015 J. Am. Chem. Soc., 2014, 136 (52), pp. 18034-18043.
Myers and Miller, 1988, Cabios 4:11-17.
Ong CK, et al. (2012) Nat Genet 44(6):690-693.
Parashar 2016 International Journal of Bioassays vol. 5, No. 02.
Persson et al. 2013. Journal of molecular biology 425:803-811.
Polakis, 2012. Cold Spring Harb Perspect Biol 4.
Rajan and Sidhu, 2012. Methods Enzymol 502:3-23.
Schuijers and Clevers, 2012. Embo J 31:685-2696.
Rizo and Gierasch Ann. Rev. Biochem. 61:387 (1992).
Ryland GL, et al. (2013) J Pathol 229(3):469-476.
Tutt et al. 1991 Eur. J. Immunol., 21, 1351-1358.
Veber and Freidinger Tins p. 392 (1985).

(Continued)

*Primary Examiner* — Elly-Gerald Stoica
(74) *Attorney, Agent, or Firm* — Cognition IP, P.C.; Edward Steakley

(57) ABSTRACT

The present disclosure is directed to novel FZD5-binding agents and methods and uses thereof for treating a disease or disorder associated with aberrant expression of activity of Frizzled protein.

5 Claims, 44 Drawing Sheets

Specification includes a Sequence Listing.

(56) References Cited

OTHER PUBLICATIONS

Waddell et al., 2015. Nature 518:495-501.
Wang K, et al. (2014) Nat Genet 46(6):573-582.
Wodarz and Nusse, 1998. Annu Rev Cell Dev Biol 14:59-88.
Wu J, et al. (2011) Proc Natl Acad Sci USA 108(52):21188-21193.
Zhang and Mo, 2016. Zhonghua Nan Ke Xue 22(2):128.
Afelik et al., 2015. Dev Biol 399:204-217.
Altschul et al. 1990. J. Mol. Biol. 215:403.
Altschul et al. 1997. Nucleic Acids Res. 25:3389-3402.
Anastas and Moon, 2013. Nat Rev Cancer 13:11-26.
Blakely et al. 2011. Methods Mol Biol 781:161-182.
Bookout et al. 2006. Curr Protoc Mol Biol Chapter 15, Unit 15 18.
Chothia and Lesk, 1987. J. Mol. Biol. 196:901-917.
Chothia et al. 1989. Nature 342:878-883.
Cole, et al. 1985 In: Monoclonal Antibodies and Cancer Therapy, AlanR. Liss, Inc., pp. 77-96.
Colwill et al. 2011. Nat Methods 8:51-558.
Cruse and Lewis (Editors), Conjugate Vaccines (Contributions to Microbiology and Immunology vol. 10). 1989.
Cote et al. 1983. Proc Natl Acad Sci USA 80:2026-2030.
Davies et al. 1990. Annual Rev Biochem 59:439-473.
Eden et al. 2009. BMC Bioinformatics 10:48.
Evans et al. 1987. J. Med. Chem. 30:1229.
Fauchere J. 1986. Adv. Drug Res. 15:29 ( ).
Fellouse and Sidhu, 2007. In "Making and using antibodies" (G. C. Howard & M. R. Kaser, Eds.), pp. 157-180, CRC Press, Boca Raton, FL.
Furukawa T, et al. (2011) Sci Rep 1:161.
Giannakis et al. Nature Genetics 46:1264-1266 (2014).
Green and Sambrook. Molecular Cloning: A Laboratory Manual (4th edition Cold Spring Harbor Laboratory Press, Cold Spring Harbor, N.Y, (2012)).

Gruber,M et al. 1994. J. Immunol., 152, 5368-5374.
Hao et al., 2012. Nature 485:195-200.
Harlow E and Lane D, 1988. Antibodies: A Laboratory Manual, Cold Spring Harbor Laboratory Press, Cold Spring Harbor, NY.
Hart et al. 2014. Molecular systems biology 10:733.
Hart et al. 2015. Cell 163:1515-26.
Hart and Moffat , 2015. Bagel: A computational framework for identifying essential genes from pooled library screens. bioRxiv 2015.
Holliger et al, 1993 . Proc Natl Acad Sci U S A. Jul. 15, 1993 ; 90(14) :6444-8.
Hsu et al. 2013. Nat Biotechnol 31:27-832.
Huse et al. 1989. Science 246:1275-1281.
Ivanov et al., 2007. Oncogene 26:2873-2884.
Janssens et al. 2004. Tumour Biol. 25(4):161-71).
Jiang et al. 2013. Proc Natl Acad Sci USA 110(31):12649-12654.
Kabat et al. 1991. Sequences of Proteins of Immunological Interest, 5th Ed. Public Health Service, National Institutes of Health, Bethesda, Md.
Lolyd et al. Protein Engineering, Design & Selection, 22: 159-168, 20009.
International Search Report and Written Opinion of the International Search Authority in international application No. PCT/CA2017/050090, mailed on May 2, 2017.
Tsukiyama, Tadasuke, et al. "Molecular role of RNF43 in canonical and noncanonical Wnt signaling." Molecular and cellular biology 35.11 (2015): 2007-2023.
Jiang, Xiaomo, et al. "Dishevelled promotes Wnt receptor degradation through recruitment of ZNRF3/RNF43 E3 ubiquitin ligases." Molecular cell 58.3 (2015): 522-533.
Steinhart, Zachary, et al. "Genome-wide CRISPR screens reveal a Wnt-FZD5 signaling circuit as a druggable vulnerability of RNF43-mutant pancreatic tumors." Nature medicine 23.1 (2017): 60-68.

* cited by examiner

METHOD OF SCREENING FOR COMPOUNDS THAT INHIBIT PROLIFERATION OF PANCREATIC CANCER CELLS HAVING A LOSS-OF-FUNCTION MUTATION IN THE RNF43 GENE

RELATED APPLICATIONS

This application is a continuation of U.S. application Ser. No. 16/073,198, filed on Jul. 26, 2018, which is a 371 U.S. National Stage application of International Application No. PCT/CA2017/050090, filed on Jan. 27, 2017, which claims the benefit of priority to U.S. Provisional application No. 62/289,012 filed on Jan. 29, 2016, the contents of which are incorporated herein by reference in their entirety.

A computer readable form of the Sequence Listing submitted via EFS-WEB and created on Feb. 15, 2021, is herein incorporated by reference.

FIELD

This disclosure relates generally to Frizzled protein-binding agents, and to methods and uses of these binding agents.

BACKGROUND

Wnt signaling pathways activated by binding a Wnt-protein ligand to a Frizzled family receptor are normally implicated in various important biological processes, including development, cell proliferation, differentiation, survival and migration (Wodarz and Nusse 1998; Schuijers and Clevers 2012; Afelik et al., 2015). Aberrant Wnt signaling pathways, however, are involved in initiation and/or maintenance of numerous major diseases (Polakis 2012; Waddell et al., 2015) for which effective, or optimally effective, therapeutic agents are urgently required (Anastas and Moon 2013). Such diseases include pancreatic cancers (Furukawa et al., 2011; Wu et al., 2011; Jiang et al., 2013), colorectal adenocarcinomas and endometrial carcinomas (Giannakis et al., 2014; Koo et al., 2012; Kinde et al., 2013), ovarian tumors (Ryland et al., 2013), cholangiocarcinoma (Ong et al., 2012), stomach cancers (Wang et al., 2014), liver cancers (Ong et al., 2012), renal cell carcinoma (Janssens et al., 2004), breast cancer (Liu et al., 2016), prostate cancer (Zhang and Mo, 2016) and lung cancer. To date, however, developing drugs against the Wnt pathway for treating such diseases has proven challenging (Madan and Virshup, 2015).

SUMMARY

The present inventors have identified novel Frizzled protein-binding antibody variable regions that, when incorporated into antibodies and Fabs, enable these to recognize one or more Frizzled proteins. Frizzled proteins are receptors involved in many important biological processes such as development, cell proliferation, survival, migration and stem cell maintenance. Abnormal expression and signaling of these receptors and their ligands, Wnt proteins, have been associated with numerous pathological conditions including cancer.

In particular, the inventors have identified novel Frizzled protein-binding antibody variable regions (antibody variable region IDs Fv-2898 to Fv-2936) that, when incorporated into Fabs, enable these to bind to cell surface expressed Frizzled-5 (FZD5) protein. In addition enabling binding to FZD5, novel antibody variable regions disclosed herein also enable antibodies and Fabs to further bind to one or more of the cell-surface expressed Frizzled proteins FZD1, FZD2, FZD4, FZD7, FZD8, FZD9 and FZD10. The inventors have further shown that antibodies incorporating novel antibody variable regions disclosed herein bind FZD5 with high affinity. The inventors have also shown that antibodies and Fabs incorporating novel antibody variable regions disclosed herein have anti-proliferative activity against various FZD5-expressing cancer cells such as those with mutations in RNF43, a negative regulator of Wnt signaling.

The inventors have determined the amino acid sequences of the complementarity determining regions (CDRs) of antibody variable regions Fv-2898 to Fv-2936, as shown in Tables 3A-C (VL domain CDRs), and Tables 4A-C (VH domain CDRs), and have determined the nucleotide sequences encoding these CDRs, as shown in Tables 5A-C (VL domain CDRs) and Tables 6A-C (VH domain CDRs). The inventors have further determined the amino acid sequences, and nucleotide sequences encoding same, of the framework (FR) regions of antibody variable regions Fv-2898 to Fv-2936, as shown in Table 7. In one exemplary embodiment, the amino acid sequence, and nucleotide sequence encoding same, of antibody IgG-2919 having antibody variable region Fv-2919 is provided, as shown in Table 8.

Accordingly, the present disclosure provides an isolated FZD5-binding agent that binds FZD5 with an affinity ($K_D$) less than or equal to 200 picomolar. In various embodiments, the $K_D$ is less than or equal to 110 pM, less than or equal to 88 pM, or less than or equal to 10 pM.

In various embodiments, the FZD5-binding agent further has one or more Frizzled protein-binding affinities selected from:

(i) a FZD8-binding affinity ($K_D$) selected from an affinity less than or equal to 60 pM, an affinity less than or equal to 50 pM, an affinity less than or equal to 45 pM, an affinity less than or equal to 42 pM, and an affinity less than or equal to 25 pM;

(ii) a FZD1-binding affinity ($K_D$) less than or equal to 1.5 pM;

(iii) a FZD2-binding affinity ($K_D$) less than or equal to 910 pM; and (iv) a FZD7-binding affinity ($K_D$) less than or equal to 500 pM.

In another embodiment, the FZD5-binding agent binds the Ala27-Pro167 segment of FZD5 (SEQ ID NO: 368).

In other embodiments, the FZD5-binding agent none of, or one or more of: FZD1, FZD2, FZD4, FZD7, FZD8, FZD9 and FZD10, e.g. as determined via flow cytometry analysis of binding of the FZD5-binding agent to cells expressing Frizzled protein. In one embodiment, the FZD5-binding agent binds at least 2, at least 3, at least 4, at least 5, at least 6, at least 7 or at least 8 Frizzled proteins.

In other embodiments, the FZD5-binding agent has a Frizzled protein-binding profile selected from:

(i) a profile wherein the FZD5-binding agent binds FZD4 and FZD8; and does not bind one or more Frizzled proteins selected from FZD1, FZD2, FZD3, FZD4, FZD6, FZD7, FZD9 and FZD10;

(ii) a profile wherein the FZD5-binding agent binds FZD4, FZD8 and FZD10; and does not bind one or more Frizzled proteins selected from FZD1, FZD2, FZD3, FZD6, FZD7 and FZD9;

(iii) a profile wherein the FZD5-binding agent binds FZD4 and FZD8; and does not bind one or more Frizzled proteins selected from FZD1, FZD2, FZD3, FZD6, FZD7, FZD9 and FZD10;

(iv) a profile wherein the FZD5-binding agent binds FZD2, FZD4, FZD7 and FZD8; and does not bind one or more Frizzled proteins selected from FZD1, FZD3, FZD6, FZD9 and FZD10;

(v) a profile wherein the FZD5-binding agent binds FZD1 and FZD7; and does not bind one or more Frizzled proteins selected from FZD2, FZD3, FZD4, FZD6, FZD8, FZD9 and FZD10;

(vi) a profile wherein the FZD5-binding agent binds FZD1, FZD2 and FZD8; and does not bind one or more Frizzled proteins selected from FZD3, FZD4, FZD6, FZD7, FZD9 and FZD10;

(vii) a profile wherein the FZD5-binding agent binds FZD1, FZD2 and FZD7; and does not bind one or more Frizzled proteins selected from FZD3, FZD4, FZD6, FZD8, FZD9 and FZD10;

(viii) a profile wherein the FZD5-binding agent binds FZD1, FZD2, FZD7 and FZD8; and does not bind one or more Frizzled proteins selected from FZD3, FZD4, FZD6, FZD9 and FZD10;

(ix) a profile wherein the FZD5-binding agent binds FZD1, FZD2, FZD4 and FZD7; and does not bind one or more Frizzled proteins selected from FZD3, FZD6, FZD8, FZD9 and FZD10;

(x) a profile wherein the FZD5-binding agent binds FZD1, FZD2, FZD4, FZD7 and FZD8; and does not bind one or more Frizzled proteins selected from FZD3, FZD6, FZD9 and FZD10; and (xi) a profile wherein the FZD5-binding agent binds FZD1, FZD2, FZD4, FZD7, FZD8, FZD9 and FZD10; and does not bind one or more Frizzled proteins selected from FZD3 and FZD6.

In another embodiment, the Frizzled protein-binding profile is a profile of binding to cell surface-expressed Frizzled proteins as determined via flow cytometry.

In another embodiment, the FZD5-binding agent binds FZD5 and FZD8. In various embodiments, the FZD5-binding agent binds FZD8 with an affinity ($K_D$) less than or equal to 1 nM, less than or equal to 60 pM, less than or equal to 50 pM, less than or equal to 45 pM, less than or equal to 42 pM, or less than or equal to 25 pM. In one embodiment, the FZD5-binding agent binds FZD8 with an affinity ($K_D$) less than or equal to 1 nM, less than or equal to 60 pM, less than or equal to 50 pM, less than or equal to 45 pM, less than or equal to 42 pM, or less than or equal to 25 pM.

The disclosure also provides a FZD5-binding agent comprising an antibody variable region that specifically binds human FZD5.

In one embodiment, the antibody variable region comprises the complementarity determining regions (CDRs) of an antibody variable region selected from antibody variable regions Fv-2898 to Fv-2936, wherein the amino acid sequences of the CDRs of antibody variable regions Fv-2898 to Fv-2936 are shown in Tables 3A-C and Tables 4A-C.

In another embodiment, the antibody variable region comprises the CDRs of an antibody variable region selected from antibody variable regions Fv-2898 to Fv-2936, wherein the amino acid sequences of the CDRs of antibody variable regions Fv-2898 to Fv-2936 are shown in Tables 3A-C and Tables 4A-C, and further comprises the amino acid residues at positions 39, 55 and 66 of the VH domain of the selected antibody variable region, as also shown in Tables 3A-C and Tables 4A-C.

In other embodiments, the amino acid sequences of CDR-L1, CDR-L2, CDR-L3, CDR-H1, CDR-H2 and CDR-H3 of the antibody variable region correspond to SEQ ID NOs: 35, 36, 58, 97, 134, and 155, respectively, or conservative functional variants thereof.

In another embodiment, the amino acid sequences of CDR-11, CDR-L2, CDR-L3, CDR-H1, CDR-H2 and CDR-H3 of the antibody variable region are shown in SEQ ID NOs: 35, 36, 58, 97, 134, and 155, respectively, and the amino acid residues at positions 39, 55 and 66 in the VH domain of the antibody variable region are an isoleucine residue, a serine residue and a serine residue, respectively.

In further embodiments, the antibody variable region is selected from antibody variable regions Fv-2898 to Fv-2936.

In another embodiment, the antibody variable region is an antibody variable region selected from Fv-2898, Fv-2899, Fv-2900, Fv-2901, Fv-2902, Fv-2903, Fv-2904, Fv-2905, Fv-2906, Fv-2907, Fv-2908, Fv-2909, Fv-2910, Fv-2911, Fv-2912, Fv-2913, Fv-2914, Fv-2915, Fv-2916, Fv-2917, Fv-2918, Fv-2919, Fv-2920, Fv-2921, Fv-2922, Fv-2923, Fv-2924, Fv-2925, Fv-2926, Fv-2927, Fv-2928, Fv-2929, Fv-2930, Fv-2931, Fv-2932, Fv-2933, Fv-2934, Fv-2935 and Fv-2936.

The disclosure further provides an isolated FZD5-binding agent that binds to the same epitope as any of the FZD5-binding agents comprising an antibody variable region as disclosed herein.

In one embodiment, the FZD5-binding agent is selected from the group consisting of a FZD5-binding antibody, aFZD5-binding antibody fragment, a FZD5-binding Fab, a FZD5-binding scFv and a phage-Fab wherein the Fab is a FZD5-binding Fab.

In another embodiment, the FZD5-binding agent comprises human antibody constant regions.

In another embodiment, the FZD5-binding agent is an IgG molecule.

In another embodiment, the binding agent is labelled with a detection agent.

The disclosure also provides a conjugate comprising (1) a FZD5-binding agent as disclosed herein attached to (2) an effector agent.

In one embodiment, the effector agent is an anti-neoplastic agent.

In another embodiment, the effector agent is a toxin.

The disclosure also provides a pharmaceutical composition comprising a FZD5-binding agent or a conjugate as disclosed herein, and a carrier.

The disclosure also provides use of an effective amount of a FZD5-binding agent as disclosed herein, a conjugate as disclosed herein or a pharmaceutical composition as disclosed herein for treating or preventing a cancer.

Also provided is use of an effective amount of a FZD5-binding agent as disclosed herein, a conjugate as disclosed herein or a pharmaceutical composition as disclosed herein in the manufacture of a medicament for treating or preventing a cancer.

Yet further provided is use of an effective amount of a FZD5-binding agent as disclosed herein, a conjugate as disclosed herein, or a pharmaceutical composition as disclosed herein, for treating or preventing a cancer.

The disclosure also provides a method of treating or preventing a cancer comprising administering an effective amount of a FZD5-binding agent as disclosed herein, a conjugate as disclosed herein or a pharmaceutical composition as disclosed herein to a subject in need thereof.

Herein also provided is a method of treating or preventing cancer comprising administering an effective amount of an inhibitor of binding between FZD5 and Wnt7B to a subject in need thereof.

Further provided is use of an effective amount of an inhibitor of binding between FZD5 and Wnt7B for treating or preventing a cancer in a subject in need thereof.

Also provided is use of an effective amount of an inhibitor of binding between FZD5 and Wnt7B in the manufacture of a medicament for treating or preventing a cancer in a subject in need thereof.

Yet further provided is use of an effective amount of an inhibitor of binding between FZD5 and Wnt7B for treating or preventing a cancer in a subject in need thereof.

In embodiments of the uses and methods disclosed herein, the inhibitor of binding between FZD5 and Wnt7B inhibits the cellular production of Wnt7B or FZD5, optionally by CRISPR/Cas-mediated knockout of the gene which encodes Wnt7B or FZD5, respectively.

In various embodiments of the uses and methods disclosed herein, the cancer is associated with one or more of: a loss of function of a negative regulator of Wnt signaling, elevated levels of FZD5 signaling, and elevated levels of cell surface-expressed FZD5.

In an embodiment, the negative regulator of Wnt signaling is RNF43.

In various embodiments of the uses and methods disclosed herein, the cancer is colorectal cancer, endometrial cancer, ovarian cancer, cholangiocarcinoma, pancreatic cancer, stomach cancer, liver cancer, breast cancer, renal cancer or lung cancer The disclosure also provides a FZD5-binding agent as disclosed herein, a conjugate as disclosed herein or a pharmaceutical composition as disclosed herein for detecting FZD5-expressing cells and/or for quantitating levels of FZD5 expression of FZD5-expressing cells.

In one embodiment, the FZD5-expressing cells are cancer cells.

The disclosure also provides a method of screening for agents that inhibit binding FZD5 and Wnt7B, comprising:

a) measuring binding between FZD5 and Wnt7B;
b) exposing FZD5 and Wnt7B to a test agent; and
c) determining if the test agent inhibits binding between FZD5 and Wnt7B.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DRAWINGS

Embodiments are described below in relation to the drawings in which:

FIGS. 1A-C are a series of illustrations depicting a genome-wide CRISPR/Cas9 screen identifying genetic vulnerabilities of RNF43-mutant PDAC cells. FIG. 1A depicts fold change distributions of gRNA targeting essential genes (solid lines) or nonessential genes (dashed lines) at the indicated time points after infection. Guides targeting essential genes drop out of the population. FIG. 1B depicts ranked differential fitness score reveals context dependent lethality in HPAF-II. Bayes Factor (BF) scores from HPAF-II were compared to mean BF scores from HeLa, HCT116, DLD-1, RPE-1 and GBM and converted to a Z-score. FIG. 1C depicts selected GO biological process terms enriched among genes ranked in (B).

FIG. 2 is a graph depicting enrichment and depletion of Wnt pathway genes in HPAF-II TKO screen. Genes ranked by BF. Multiple genes involved in Wnt signal transduction are above the 5% false discovery rate threshold for essential genes. APC, GSK3B and ZNRF3 are in the bottom 80 BFs, indicating possible positive enrichment with gene knockout.

FIG. 3 is a histogram depicting GO Term enrichment for differential essential genes in HPAF-II. Full list of enriched and depleted GO terms for HPAF-II versus published TKO screens, as in FIG. 1C.

FIGS. 4A-G are a series of illustrations depicting that FZD5 knockout inhibits proliferation of RNF43-mutant PDAC cell lines and activation of Wnt target genes. FIG. 4A depicts proliferation assay in HPAF-II cells stably expressing Cas9 and transduced with indicated gRNA. Cells were plated at low density post-selection and were fixed and stained with crystal violet 10 days later. FIG. 4B depicts T7 endonuclease I cleavage assay confirming gRNA-mediated gene editing in transduced cells. Expected digest products are located in Table 1. FIG. 4C depicts cell viability assays in various PDAC cell lines stably expressing Cas9, transduced with indicated gRNAs. HPAF-II, PaTu 8988s and AsPC-1 are sensitive to Wnt pathway inhibition and contain RNF43 mutations. PANC-1 and BxPC-3 are insensitive to Wnt pathway inhibition and are RNF43-wild type. FIG. 4D-F depicts RT-qPCR of Wnt target genes (AXIN2, NKD1) and differentiation induced gene, MUC5AC, in HPAF-II and PaTu8988s Cas9 cell lines transduced with indicated gRNA, 7 days post-infection. All data are represented as means+/−SD, n=3. *p<0.001, p<0.01, and *p<0.05, two-tailed unpaired t test, all comparisons to LacZ control gRNA. FIG. 4G depicts inhibition of proliferation of HPAF-II cells by transduction of WNT7B gRNA, supporting results indicating that Wnt7B-FZD5 signaling is responsible for the bulk of beta-catenin signaling in RNF43-mutant PDAC cells.

FIG. 5 depicts gel electrophoresis photographs of a T7 endonuclease I cleavage assay to confirm Cas9 activity in PDAC cell lines. Indicated cell lines expressing Cas9 were transduced with lentiviruses delivering indicated gRNA. Five to seven days post transduction genomic DNA was harvested. The FZD7 locus was subsequently PCR amplified and subjected to T7 endonuclease I cleavage assay to detect the presence of indels.

FIG. 6 is a histogram depicting that anti-FZD5 Fabs generated specifically bind recombinant FZD5-Fc, as determined via ELISA.

FIGS. 7A-E are a series of illustrations depicting that Wnt and Frizzled expression patterns are not predictive of essentiality. FIG. 7A depicts that Frizzled receptors are composed of an extracellular N-terminal cysteine rich domain (CRD), seven-pass transmembrane domain (7TM), and the intracellular C-terminal domain (CD). FIG. 7B depicts a sequence identity tree among CRDs of human Frizzled proteins. FIG. 7C depicts a schematic for Fab selection by phage display. Phage-displayed Fabs are selected for binding to an immobilized Frizzled CRD of interest. Unbound phages are washed away, and bound phages are amplified over 3-4 rounds to enrich for specific Fabs. Candidate Fabs are validated by flow cytometry using Frizzled-CRD-GPI over-expressing CHO cell lines for each human Frizzled. FIG. 7D depicts a specificity profile of anti-Frizzled Fabs forming the 'Frizzled profiler'. Black boxes indicate the intended Frizzled family member target for each Fab. Grey boxes indicate cross-reactivity with other Frizzled family members. FIG. 7E depicts determination of Frizzled protein membrane expression in HPAF-II cells. Value indicates median fluorescence intensity (MFI). MFI greater than 1.35× the secondary antibody alone was taken as evidence of endogenous expression.

FIG. 8 is a diagram depicting specificity profiling of anti-Frizzled Fabs with flow cytometry. Specificity profiling of the Frizzled profiler Fabs by flow cytometry in CHO-GPI cells over-expressing CRDs of FZD1, FZD2, FZD3, FZD4, FZD5, FZD6, FZD7, FZD8, FZD9 or FZD10. Numerical values indicate a fold-increase in mean fluorescence intensity of the reacting Fab over the background (secondary antibody alone) normalized to the control (C, CHO-GPI).

Figure 10A:
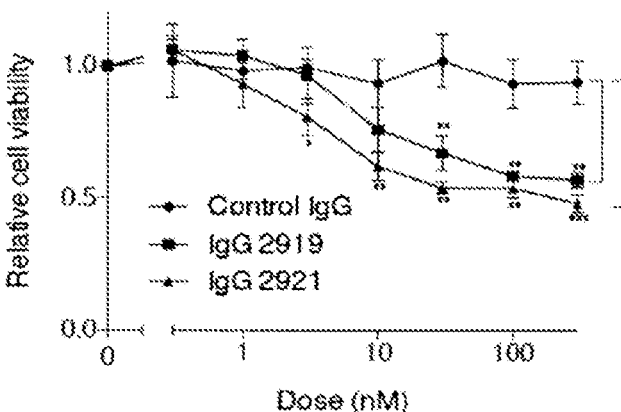
Figure 10B:
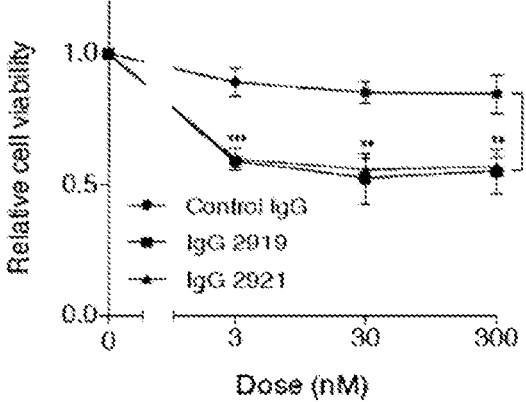
Figure 10C:
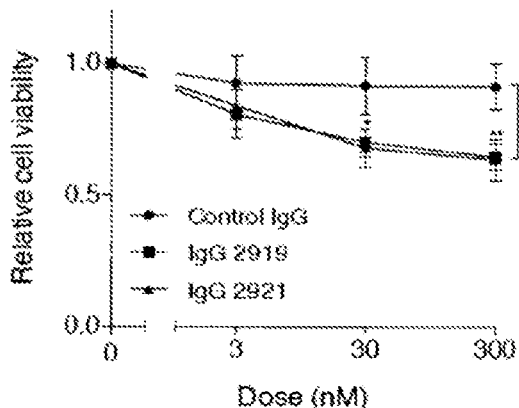
Figure 10D:
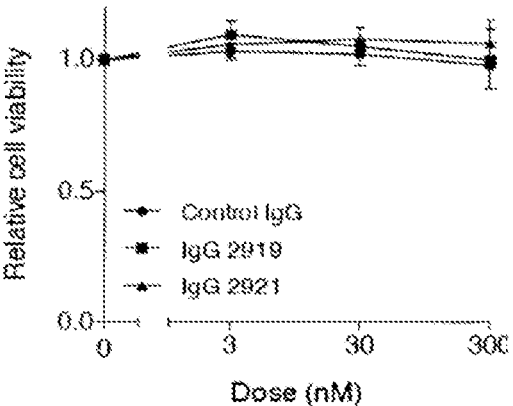
Figure 10E:
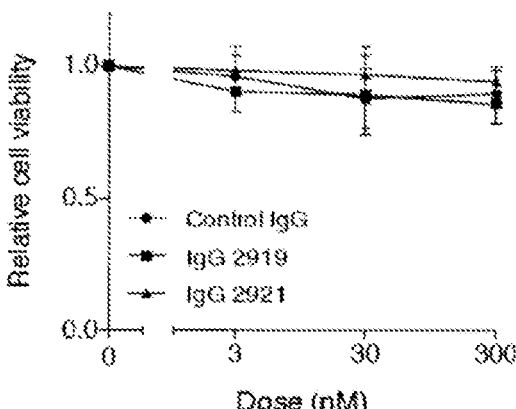
Figure 10F:
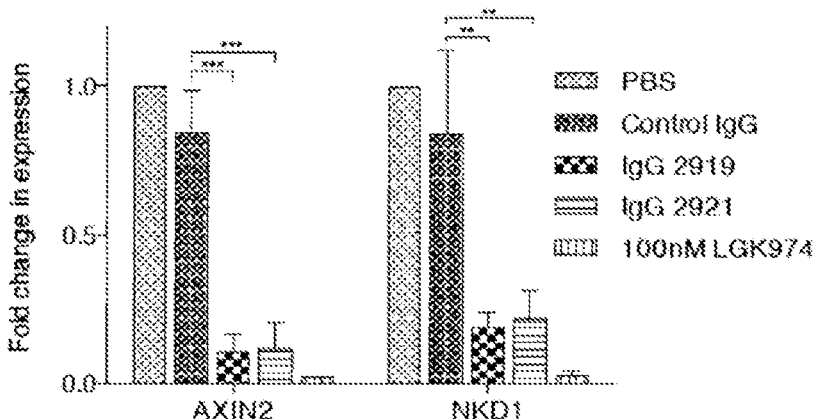
Figure 10G:
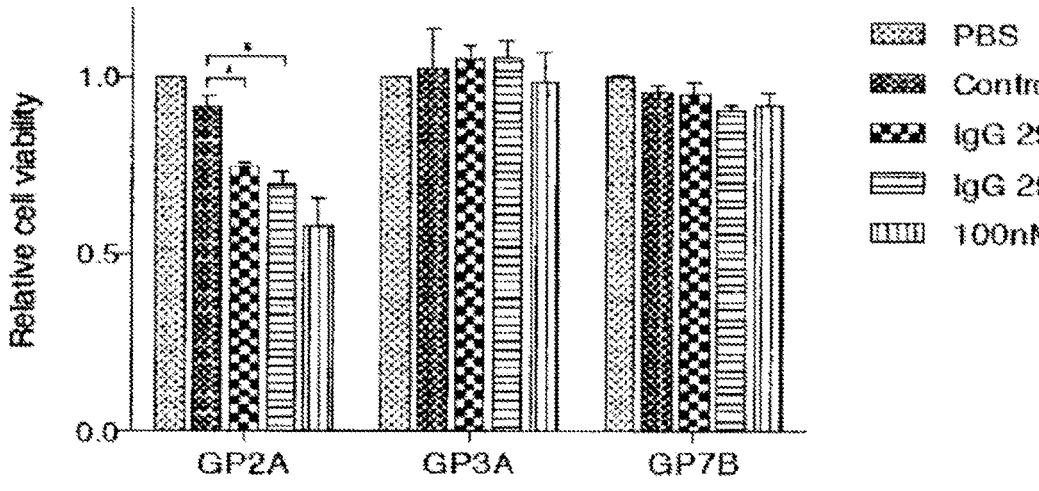

FIGS. 10A-G are a series of illustrations depicting that anti-FZD5 antibodies inhibit growth of RNF43-mutant PDAC in vitro and in vivo. FIGS. 10A-E depict cell viability assays in RNF43-mutant and RNF43-wild type cell lines. RNF43-mutant cell lines HPAF-II (FIG. 10A), AsPC-1 (FIG. 10B), PATU8988T (FIG. 10C) exhibit sensitivity to anti-FZD5 IgGs (IgG-2919/IgG-2921), whereas RNF43-wild type cell lines PANC-1 (FIG. 10D) and BxPC-3 (FIG. 10E) do not. FIG. 10F depicts that treatment with 300 nM IgG-2919 or IgG-2921 suppresses expression of Wnt-beta-catenin target genes AXIN2 and NKD1 in HPAF-II. FIG. 10G depicts cell viability assays in patient derived cell lines. GP2A (having homozygous R117H mutation in RNF43) is sensitive to IgG-2919 or IgG-2921 whereas GP3A and GP7A (both RNF43-wild type) are insensitive. All data are represented as means+/−SD, n=3, unless otherwise noted. *$p<0.001$, $p<0.01$, and *$p<0.05$, two-tailed unpaired t test.

Figure 11:
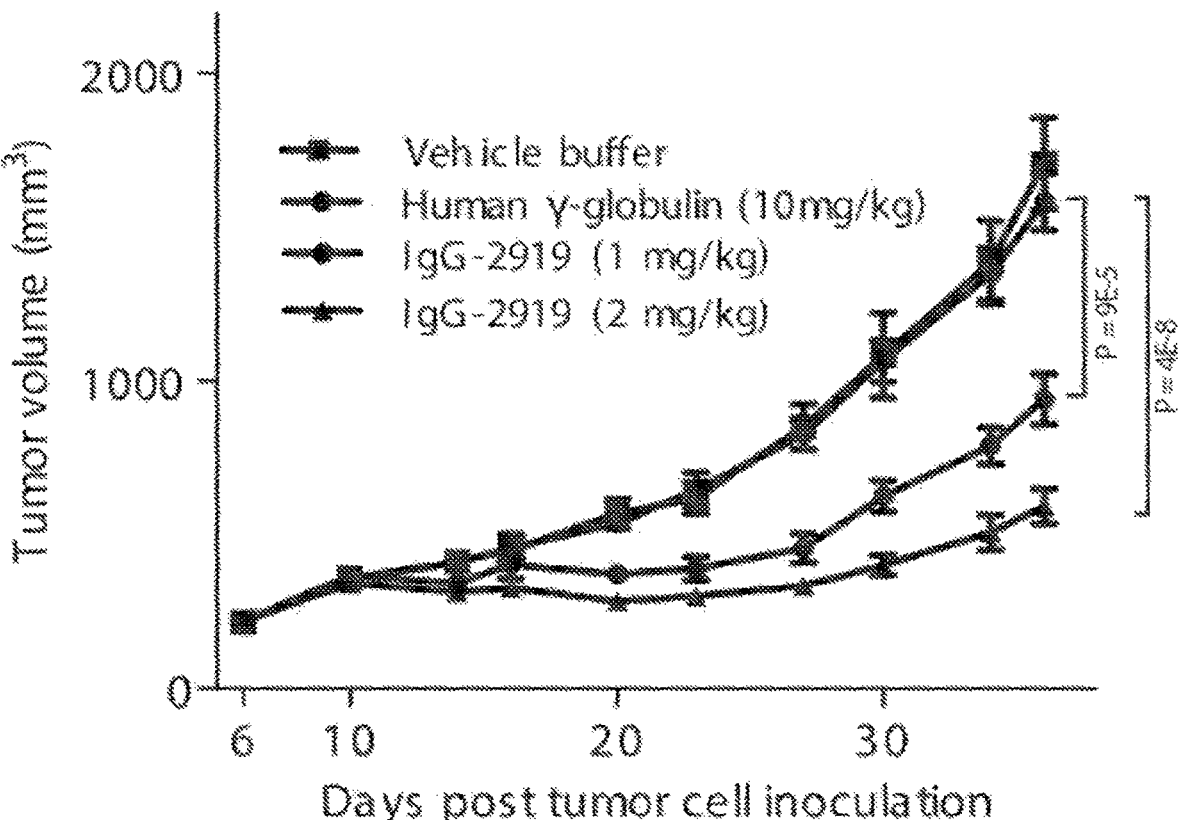

FIG. 11 is a graph depicting that treatment with IgG-2919 suppresses growth of RNF43-mutant tumors in HPAF-II mouse xenografts (n=10 for each condition). All data are represented as means+/−SD, n=3, unless otherwise noted. *$p<0.001$, $p<0.01$, and *$p<0.05$, two-tailed unpaired t test.

Figure 12A:
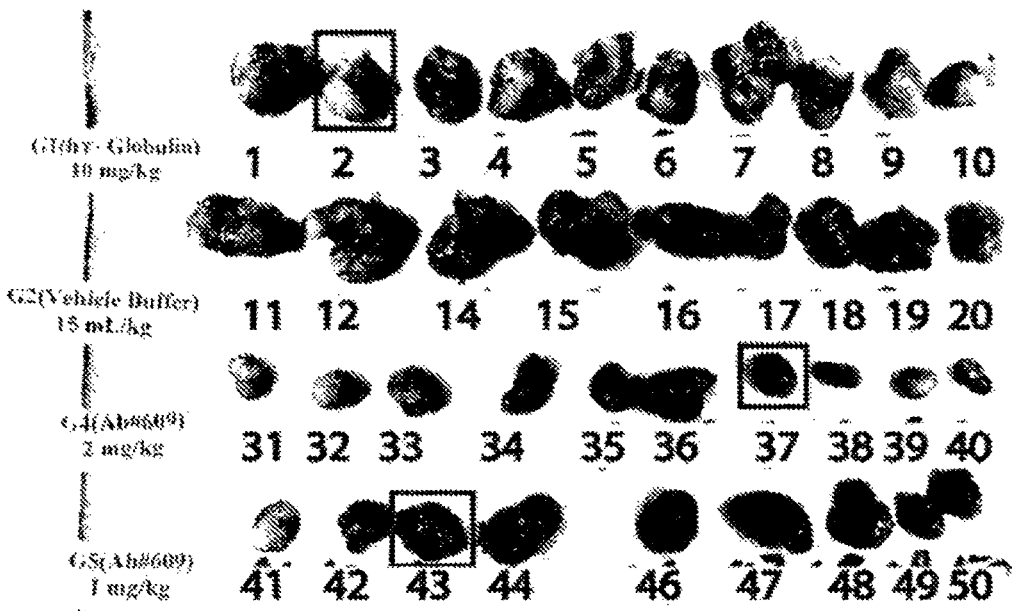
Figure 12B:
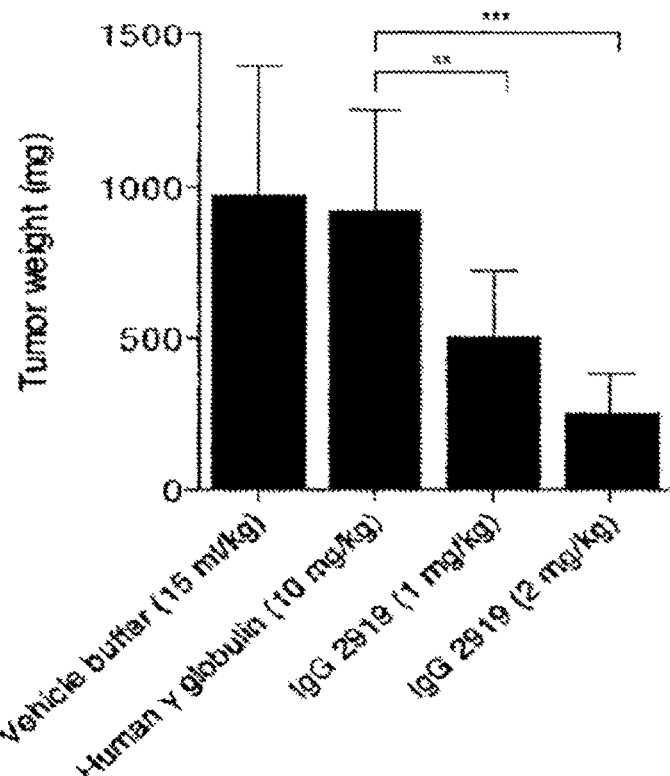
Figure 12C:
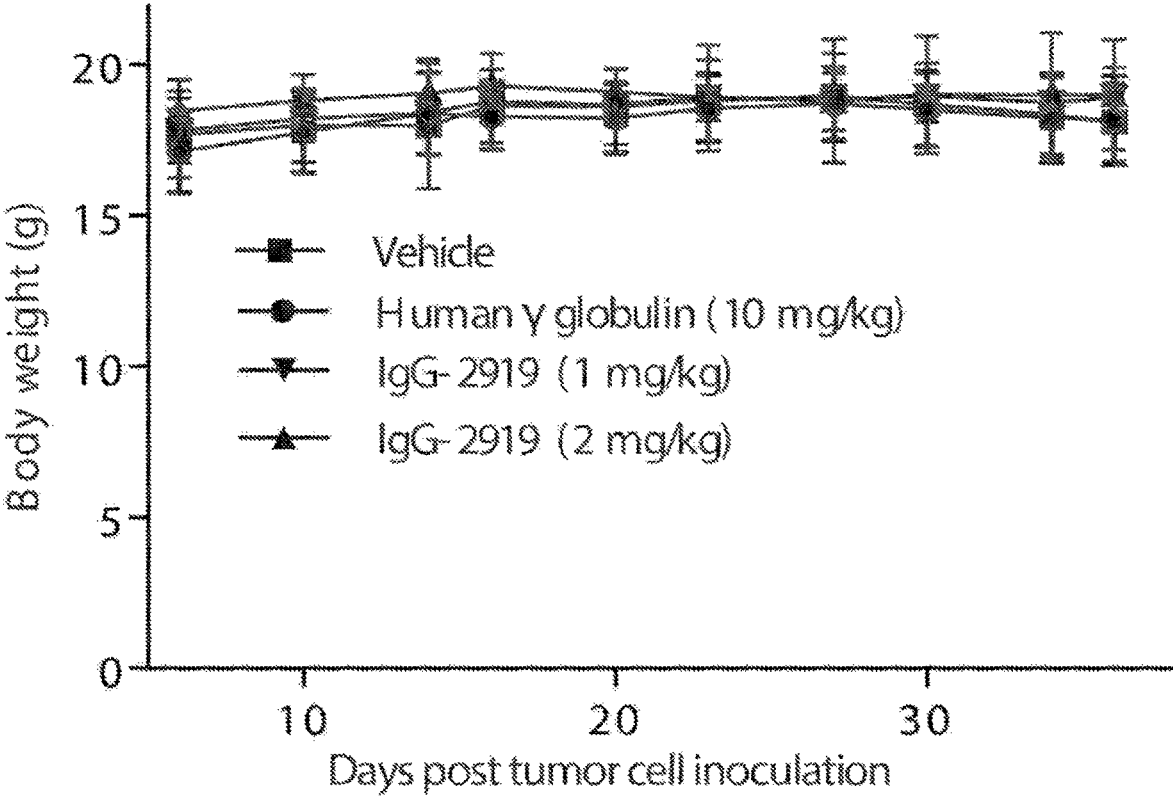

FIGS. 12A-C are a series of illustrations depicting that anti-FZD5 IgG-2919 inhibits HPAF-II growth in vivo (mouse xenograft). FIG. 12A depicts images of all tumors at the end of treatment. Black boxes indicate tumors analyzed at end of treatment and showing increased mucin as determined via Alcian blue staining, consistent with differentiation following treatment with the IgG 2919. FIG. 12B depicts tumor weights at the end of treatment. *$p<0.001$, $p<0.01$, two-tailed unpaired t test, n=9. FIG. 12C depicts stable mouse body weights over course of treatment.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. For example, the term "a cell" includes a single cell as well as a plurality or population of cells. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Compositions of Matter

FZD5-Binding Agents

The present inventors have identified novel Frizzled protein-binding antibody variable regions (antibody variable region IDs Fv-2898 to Fv-2936. When incorporated into Fabs, these antibody variable regions enable the Fabs to bind to cell surface-expressed Frizzled-5 (FZD5) protein. In addition to enabling binding to FZD5, novel antibody variable regions disclosed herein also enable antibodies and Fabs to further bind to one or more of the cell-surface expressed Frizzled proteins FZD1, FZD2, FZD4, FZD7, FZD8, FZD9 and FZD10. The inventors have further shown that antibodies incorporating novel antibody variable regions disclosed herein bind FZD5 with high affinity. The inventors have also shown that antibodies and Fabs incorporating novel antibody variable regions disclosed herein have anti-proliferative activity against various FZD5-expressing cancer cells such as those with mutations in RNF43, a negative regulator of Wnt signaling.

The inventors have determined the amino acid sequences of the complementarity determining regions (CDRs) of antibody variable regions Fv-2898 to Fv-2936, as shown in Tables 3A-C (VL domain CDRs), and Tables 4A-C (VH domain CDRs), and have determined the nucleotide sequences encoding these CDRs, as shown in Tables 5A-C (VL domain CDRs) and Tables 6A-C (VH domain CDRs). The inventors have further determined the amino acid sequences, and nucleotide sequences encoding same, of the framework (FR) regions of antibody variable regions Fv-2898 to Fv-2936, as shown in Table 7. In one exemplary embodiment, the amino acid sequence, and nucleotide sequence encoding same, of antibody IgG-2919 having antibody variable region Fv-2919 is provided, as shown in Table 8.

The present disclosure therefore provides novel isolated binding agents that bind to Frizzled-5 (FZD5) protein, referred to herein as "FZD5-binding agents". As used herein, a FZD5-binding agent which "binds FZD5", "specifically binds FZD5" or is referred to as "anti-FZD5" is an agent which binds FZD5-expressing cells as opposed to cells not expressing FZD5 (as determined via flow cytometric analysis) and/or which binds human FZD5 according to other criteria described herein. The aforementioned terminology employs FZD5 merely for illustrative purposes and applies identically herein in reference to any other protein. The terms "immunoreacts with FZD5", or "is directed against FZD5" are also used herein for the same purpose.

In one embodiment, the FZD5-binding agent binds FZD5 with an affinity ($K_D$) less than or equal to 200 picomolar.

In various embodiments, the FZD5-binding agent further has one or more Frizzled protein-binding affinities selected from: a FZD8-binding affinity ($K_D$) selected from an affinity less than or equal to 60 pM, an affinity less than or equal to 50 pM, an affinity less than or equal to 45 pM, an affinity less than or equal to 42 pM, and an affinity less than or equal to 25 pM. In another embodiment, the FZD5-binding agent further has a FZD1-binding affinity ($K_D$) less than or equal to 1.5 pM.

In a further embodiment, the FZD5-binding agent further has a FZD2-binding affinity ($K_D$) less than or equal to 910 pM; and a FZD7-binding affinity ($K_D$) less than or equal to 500 pM.

In an additional embodiment, the FZD5-binding agent further has a FZD7-binding affinity ($K_D$) less than or equal to 500 pM.

In various embodiments, the FZD5-binding agent further has a Frizzled protein-binding profile selected from:

(i) a profile wherein the FZD5-binding agent binds FZD4 and FZD8; and does not bind one or more Frizzled proteins selected from FZD1, FZD2, FZD3, FZD6, FZD7, FZD9 and FZD10;

(ii) a profile wherein the FZD5-binding agent binds FZD4, FZD8 and FZD10; and does not bind one or more Frizzled proteins selected from FZD1, FZD2, FZD3, FZD6, FZD7 and FZD9;

(iii) a profile wherein the FZD5-binding agent binds FZD8; and does not bind one or more Frizzled proteins selected from FZD1, FZD2, FZD3, FZD4, FZD6, FZD7, FZD9 and FZD10;

(iv) a profile wherein the FZD5-binding agent binds FZD2, FZD4, FZD7 and FZD8; and does not bind one or more Frizzled proteins selected from FZD1, FZD3, FZD6, FZD9 and FZD10;

(v) a profile wherein the FZD5-binding agent binds FZD1 and FZD7; and does not bind one or more Frizzled proteins selected from FZD2, FZD3, FZD4, FZD6, FZD8, FZD9 and FZD10;

(vi) a profile wherein the FZD5-binding agent binds FZD1, FZD2 and FZD8; and does not bind one or more Frizzled proteins selected from FZD3, FZD4, FZD6, FZD7, FZD9 and FZD10;

(vii) a profile wherein the FZD5-binding agent binds FZD1, FZD2 and FZD7; and does not bind one or more Frizzled proteins selected from FZD3, FZD4, FZD6, FZD8, FZD9 and FZD10;

(viii) a profile wherein the FZD5-binding agent binds FZD1, FZD2, FZD7 and FZD8; and does not bind one or more Frizzled proteins selected from FZD3, FZD4, FZD6, FZD9 and FZD10;

(ix) a profile wherein the FZD5-binding agent binds FZD1, FZD2, FZD4 and FZD7; and does not bind one or more Frizzled proteins selected from FZD3, FZD6, FZD8, FZD9 and FZD10;

(x) a profile wherein the FZD5-binding agent binds FZD1, FZD2, FZD4, FZD7 and FZD8; and does not bind one or more Frizzled proteins selected from FZD3, FZD6, FZD9 and FZD10; and (xi) a profile wherein the FZD5-binding agent binds FZD1, FZD2, FZD4, FZD7, FZD8, FZD9 and FZD10; and does not bind one or more Frizzled proteins selected from FZD3 and FZD6.

Embodiments of the FZD5-binding agent include any one of various types of FZD5-binding molecule.

In one embodiment, the FZD5-binding agent is a polypeptide (polypeptidic FZD5-binding agent). In other embodiments, the FZD5-binding agent is a non-polypeptidic agent, such as a FZD5-binding nucleic acid or a FZD5-binding organic compound. The FZD5-binding agent may be monomeric or multimeric. The FZD5-binding agent may be polymeric or non-polymeric. Alternately, the FZD5-binding agent may be an engineered polypeptide (e.g. a naturally occurring polypeptide engineered to have a modified amino acid sequence; or a chimeric polypeptide engineered to comprise two or more naturally occurring amino acid sequences; or an engineered polypeptide selected from a library of engineered polypeptides having randomized amino acid sequences), or a chemically modified polypeptide.

In one embodiment, the FZD5-binding agent comprises an antibody variable region that specifically binds human FZD5 (also referred to herein as an "FZD5-binding antibody variable region").

In various embodiments, the FZD5-binding agent is an antibody, an antigen-binding fragment of an antibody, or an agent comprising a FZD5-binding antibody variable region.

As used herein, and unless otherwise specified, the term "antibody" refers to an immunoglobulin (Ig) molecule.

The basic antibody structural unit is known to comprise a tetramer composed of two identical pairs of polypeptide chains, each pair having one light ("L") (about 25 kDa) and one heavy ("H") chain (about 50-70 kDa). The amino-terminal portion of the light chain forms a light chain variable domain (VL) and the amino-terminal portion of the heavy chain forms a heavy chain variable domain (VH). Together, the VH and VL domains form the antibody variable region (Fv) which is primarily responsible for antigen recognition/binding. The carboxy-terminal portions of the heavy and light chains together form a constant region primarily responsible for effector function. Three highly divergent stretches within each of the VH domain and VL domain, referred to as complementarity determining regions (CDRs), are interposed between more conserved flanking stretches known as "framework regions", or "FRs". Thus, the term "FR" refers to amino acid sequences which are naturally found between, and adjacent to, CDRs in immunoglobulins. A VH domain typically has four FRs, referred to herein as VH framework region 1 (FR1), VH framework region 2 (FR2), VH framework region 3 (FR3), and VH framework region 4 (FR4). Similarly, a VL domain typically has four FRs, referred to herein as VL framework region 1 (FR1), VL framework region 2 (FR2), VL framework region 3 (FR3), and VL framework region 4 (FR4). In an antibody molecule, the three CDRs of a VL domain (CDR-L1, CDR-L2 and CDR-L3) and the three CDRs of a VH domain (CDR-H1, CDR-H2 and CDR-H3) are disposed relative to each other in three dimensional space to form an antigen-binding site within the antibody variable region. The surface of the antigen-binding site is complementary to a three-dimensional surface of a bound antigen. Unless specified otherwise, the convention employed herein to describe antibodies, including to number amino acid residues of a VL domain and of a VH domain, and to define CDRs and FRs therein is the INTERNATIONAL IMMUNOGENETICS INFORMATION SYSTEM (IMGT numbering system; Lefranc et al., 2003). The amino acid sequences of of VL and VH domains may alternately be numbered, and CDRs and FRs therein identified/defined, according to the Kabat numbering system (Kabat et al., 1991). One of ordinary skill in the art would possess the knowledge for numbering amino acid residues of a VL domain and of a VH domain, and identifying CDRs and FRs therein, according to a routinely employed numbering system such as the IMGT numbering system, the Kabat numbering system, and the like.

As used herein, unless otherwise specified, an antibody or a bivalent antibody fragment (e.g. F(ab')2) referred to as comprising "a" specific light chain or "a" specific heavy chain in the singular refers to an antibody or a bivalent antibody fragment in which both light chains or both heavy chains are identical, respectively.

The FZD5-binding agent may be an antibody, such as a human antibody, containing engineered variable regions (e.g. containing variable regions selected from a phage display library displaying engineered antibody variable regions, e.g. a phage-Fab library or a phage-scFv library, or a chimeric antibody comprising human constant regions and an antibody variable region of a non-human mammal. The FZD5-binding agent may be a humanized antibody, e.g. an antibody comprising human constant regions, human variable region framework regions, and FZD5-binding CDRs generated in a non-human mammal. The non-human mammal may be a rodent, such as a mouse, rat, rabbit, guinea pig or hamster. Alternately, the non-human mammal may be an ungulate, such as a camelid or a bovid. The FZD5-binding agent may be an antibody comprising heavy chain constant regions belonging to any type of class, or subclass. The FZD5-binding agent may comprise any type of light chain.

In one embodiment, the FZD5-binding agent is a human antibody, such as an IgG1 antibody, wherein the heavy chain constant domains are gamma1 heavy chain constant domains. In other embodiments, the FZD5-binding agent is a human antibody, such as an IgA1, IgA2, IgD, IgG2, IgG3, IgG4, IgE or IgM antibody, wherein the heavy chain constant domains are alpha1, alpha2, delta, gamma2, gamma3, gamma4, epsilon or mu heavy chain constant domains, respectively.

In yet a further embodiment, the FZD5-binding agent is an antibody wherein the light chains comprise human kappa light chain constant domains, or wherein the light chains are human kappa light chains. Alternately, the FZD5-binding agent is an antibody wherein the light chains comprise human lambda light chain constant domains, or wherein the light chains are human lambda light chains.

In still a further embodiment the FZD5-binding agent is an antibody comprising human gamma1 heavy chain constant regions and human kappa light chains.

Embodiments of FZD5-binding agents of the present disclosure further include, but are not limited to, fragment antigen-binding (Fab), single-chain Fv (scFv), single-chain Fab (scFab), Fab', Fv, chemically linked F(ab')$_2$, dsFv, dsFv', sc(Fv)$_2$, ds-scFv, (dsFv)2, scFv-Fc, scFv-based chimeric antigen receptors (CARs), Fab-based CARs, scFab-based CARs, single-chain immunoglobulin (e.g. scIgG), single-domain antibody (sdAb, nanobody), scFv-Fc, minibody (scFv-CH3), diabody, tribody, tetrabody, multimeric antibody (e.g. scFv dimer, bivalent diabody), multispecific antibody (e.g. bispecific antibody, trispecific antibody, di-scFv, tri-scFv, bispecific Fab$_2$, trispecific Fab$_2$, trispecific triabody, trispecific Fab$_3$), multimeric/multispecific antibody (e.g. scFv dimer, bispecific diabody, dsFv-dsFv'), heavy-chain antibody, Fab$_3$, divalent VHH, pentavalent VHH (pentabody), (scFv-SA)$_4$ and, [sc(Fv)2]$_2$.

In another embodiment, the FZD5-binding agent is a phage displaying a polypeptide comprising a FZD5-binding antibody variable region, such as a phage-Fab or phage-scFv.

Embodiments of FZD5-binding agents of the present disclosure still further include FZD5-binding nucleic acid aptamers (e.g. RNA aptamers or DNA aptamers; see, e.g. Lipi et al., 2016), peptide aptamers (see, e.g. Parashar, 2016), and chemically synthesized agents (e.g. synthetic antibody mimics; see, e.g. McEnaney et al., 2014).

In another embodiment, the FZD5-binding agent is a peptide analog. Peptide analogs are commonly used in the pharmaceutical industry as non-peptide drugs with properties analogous to those of the template peptide. These types of non-peptide compound are termed "peptide mimetics" or 'peptidomimetics" (see, e.g. Fauchere, 1986); Veber and Freidinger, 1985; and Evans et al., 1987). Such compounds are often developed with the aid of computerized molecular modeling. Peptide mimetics that are structurally similar to biologically useful peptides may be used to produce an equivalent biological effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH2NH—, —CH2S—, —CH2-CH2-, —CH=CH— (cis and trans), —COCH2-, CH(OH)CH2- and —CH2SO—, by methods well known in the art. Systematic substitution of one or more amino acids of a consensus sequence with a D-amino acid of the same type (e.g. D-lysine in place of L-lysine) may be used to generate more stable peptides. In addition, constrained peptides comprising a consensus sequence or a substantially identical consensus sequence variation may be generated by methods known in the art (see, e.g. Rizo and Gierasch, 1992), for example, by adding internal cysteine residues capable of forming intramolecular disulfide bridges which cyclize the peptide.

One of ordinary skill in the art would possess the necessary knowledge to obtain the novel FZD5-binding agents disclosed herein.

As described in Example 3 of the present disclosure, the inventors identified thirty-nine novel anti-FZD5 phage-Fab clones; i.e. phage-Fab clone IDs #2898 to #2936, having antibody variable region IDs Fv-2898 to Fv-2936, respectively.

The inventors further sequenced novel antibody variable regions Fv-2898 to Fv-2936 and determined the CDR amino acid sequences thereof, as shown in Tables 3A-C (light chain CDRs), and Tables 4A-C (heavy chain CDRs); and nucleotide sequences encoding these CDRs, as shown in Tables 5A-C (light chain CDRs) and Tables 6A-C (heavy chain CDRs). As discussed in more detail below, functional variants of the CDR sequences are also encompassed by the present disclosure.

Accordingly, exemplary FZD5-binding agents disclosed herein comprise, for example, amino acid sequences shown in Tables 3A-3C, Tables 4A-4C, Table 7 and Table 8 and are encoded, for example, by nucleic acid sequences shown in Tables 5A-5C, Tables 6A-6C, Table 7 and Table 8, as follows:

Table 3A: CDR-L1 amino acid sequence
 Table 3B: CDR-L2 amino acid sequence
 Table 3C: CDR-L3 amino acid sequence
 Table 4A: CDR-H1 amino acid sequence and amino acid residue at position 39
 Table 4B: CDR-H2 amino acid sequence and amino acid residues at positions 55 and 66
 Table 4C: CDR-H3 amino acid sequence
 Table 5A: nucleic acid sequence encoding CDR-L1
 Table 5B: nucleic acid sequence encoding CDR-L2
 Table 5C: nucleic acid sequence encoding CDR-L3
 Table 6A: nucleic acid sequences encoding CDR-H1 and amino acid residue at position 39
 Table 6B: nucleic acid sequences encoding CDR-H2 and amino acid residues at positions 55 and 66
 Table 6C: nucleic acid sequence encoding CDR-H3
 Table 7: amino acid sequences (and nucleic acid sequences encoding same) of VL domain FR1, VL domain FR2, VL domain FR3, VL domain FR4, VH domain FR1, VH domain FR2 segment spanning positions 40-54, VH domain FR3 segment spanning positions 67-104, and VH domain FR4
 Table 8: exemplary full length amino acid sequences (and nucleic acid sequences encoding same) of anti-FZD5 antibody IgG-2919 having antibody variable region Fv-2919

According to various embodiments, the FZD5-binding agent which comprises an antibody variable region disclosed herein comprises the CDRs, or conservative functional variants thereof, of an antibody variable region selected from Fv-2898 to Fv-2936, wherein the sequences of the CDRs for each of Fv-2898 to Fv-2936 are shown in Tables 3A-C and Tables 4A-C.

Thus, according to various embodiments, the FZD5-binding agent comprises the CDRs, or conservative functional variants thereof, of an antibody variable region selected from those of:

Fv-2898, as shown in SEQ ID NOs: 35, 36, 37, 76, 113 and 152;
 Fv-2899, as shown in SEQ ID NOs: 35, 36, 38, 77, 114 and 153;
 Fv-2900, as shown in SEQ ID NOs: 35, 36, 39, 78, 115, and 153;
 Fv-2901, as shown in SEQ ID NOs: 35, 36, 40, 79, 116, and 154;
 Fv-2902, as shown in SEQ ID NOs: 35, 36, 41, 80, 117, and 153;
 Fv-2903, as shown in SEQ ID NOs: 35, 36, 42, 81, 118, and 155;
 Fv-2904, as shown in SEQ ID NOs: 35, 36, 43, 82, 119, and 156;
 Fv-2905, as shown in SEQ ID NOs: 35, 36, 44, 83, 120, and 157;
 Fv-2906, as shown in SEQ ID NOs: 35, 36, 45, 84, 121, and 158;
 Fv-2907, as shown in SEQ ID NOs: 35, 36, 46, 85, 122, and 159;
 Fv-2908, as shown in SEQ ID NOs: 35, 36, 47, 86, 123, and 160;
 Fv-2909, as shown in SEQ ID NOs: 35, 36, 48, 87, 124 and 161;
 Fv-2910, as shown in SEQ ID NOs: 35, 36, 49, 88, 125, and 162;
 Fv-2911, as shown in SEQ ID NOs: 35, 36, 50, 89, 126 and 163;
 Fv-2912, as shown in SEQ ID NOs: 35, 36, 51, 90, 127, and 164;
 Fv-2913, as shown in SEQ ID NOs: 35, 36, 52, 91, 128 and 165;
 Fv-2914, as shown in SEQ ID NOs: 35, 36, 53, 92, 129 and 162;
 Fv-2915, as shown in SEQ ID NOs: 35, 36, 54, 93, 130 and 166;
 Fv-2916, as shown in SEQ ID NOs: 35, 36, 55, 94, 131 and 167;
 Fv-2917, as shown in SEQ ID NO: 35, 36, 56, 95, 132 and 168;
 Fv-2918, as shown in SEQ ID NO: 35, 36, 57, 96, 133 and 169;
 Fv-2919, as shown in SEQ ID NOs: 35, 36, 58, 97, 134, and 155;
 Fv-2920, as shown in SEQ ID NOs: 35, 36, 59, 98, 135, and 170;
 Fv-2921, as shown in SEQ ID NOs: 35, 36, 60, 98, 136, and 162;
 Fv-2922, as shown in SEQ ID NOs: 35, 36, 61, 99, 137, and 171;
 Fv-2923, as shown in SEQ ID NOs: 35, 36, 62, 100, 138, and 162;
 Fv-2924, as shown in SEQ ID NOs: 35, 36, 63, 101, 139, and 153;
 Fv-2925, as shown in SEQ ID NOs: 35, 36, 64, 102, 140 and 172;
 Fv-2926, as shown in SEQ ID NOs: 35, 36, 65, 103, 141, and 173;
 Fv-2927 as shown in SEQ ID NO: 35, 36, 66, 104, 142, and 174;
 Fv-2928, as shown in SEQ ID NOs: 35, 36, 67, 105, 143, and 175;

Fv-2929, as shown in SEQ ID NOs: 35, 36, 68, 106, 144, and 162;

Fv-2930, as shown in SEQ ID NOs: 35, 36, 69, 107, 145, and 153;

Fv-2931, as shown in SEQ ID NOs: 35, 36, 70, 102, 146, and 176;

Fv-2932, as shown in SEQ ID NOs: 35, 36, 71, 108, 147, and 153;

Fv-2933, as shown in SEQ ID NOs: 35, 36, 72, 109, 148, and 177;

Fv-2934, as shown in SEQ ID NOs: 35, 36, 73, 110, 149, and 155;

Fv-2935, as shown in SEQ ID NOs: 35, 36, 74, 111, 150, and 178; or

Fv-2936, as shown in SEQ ID NOs: 35, 36, 75, 112, 151 and 179).

According to various embodiments, the antibody variable region selected from Fv-2898 to Fv-2936 further comprises at the N-terminal position of the FR2 of the VH domain of the antibody variable region (also referred to as position 39 of the VH domain according to the IMGT numbering system; Lefranc et al., 2003); which is adjacent to the C-terminal residue of CDR-H1), the specific amino acid residue at position 39 shown in Table 4A for each of antibody variable regions Fv-2898 to Fv-2936, respectively.

According to further various embodiments, the antibody variable region selected from Fv-2898 to Fv-2936 further comprises at the C-terminal position of the FR2 of the VH domain of the antibody variable region (also referred to as position 55 of the VH domain according to the IMGT numbering system; Lefranc et al., 2003); which is adjacent to the N-terminal residue of CDR-H2), the specific amino acid residue at position 55 shown in Table 4B for each of antibody variable regions Fv-2898 to Fv-2936, respectively.

According to still further various embodiments, the antibody variable region selected from Fv-2898 to Fv-2936 further comprises at the N-terminal position of the FR3 of the VH domain of the antibody variable region (also referred to as position 66 of the VH domain according to the IMGT numbering system; Lefranc et al., 2003); which is adjacent to the C-terminal residue of CDR-H2), the specific amino acid residue at position 66 shown in Table 4B for each of antibody variable regions Fv-2898 to Fv-2936, respectively.

In one embodiment, the antibody variable region selected from Fv-2898 to Fv-2936 further comprises the specific amino acid residue at each of positions 39, 55 and 66 shown in Table 4A and Table 4B for each of antibody variable regions Fv-2898 to Fv-2936, respectively.

In one embodiment, the antibody variable region is selected from Fv-2898, Fv-2899, Fv-2900, Fv-2901, Fv-2902, Fv-2903, Fv-2904, Fv-2905, Fv-2906, Fv-2907, Fv-2908, Fv-2909, Fv-2910, Fv-2911, Fv-2912, Fv-2913, Fv-2914, Fv-2915, Fv-2916, Fv-2917, Fv-2918, Fv-2919, Fv-2920, Fv-2921, Fv-2922, Fv-2923, Fv-2924, Fv-2925, Fv-2926, Fv-2927, Fv-2928, Fv-2929, Fv-2930, Fv-2931, Fv-2932, Fv-2933, Fv-2934, Fv-2935 and Fv-2936.

Any of the FZD5-binding agents of the present disclosure may be obtained and suitably prepared for use using well-known techniques.

Polypeptidic FZD5-binding agents of the disclosure can be synthesized by recombinant techniques which are well known and routinely practiced in the art. A polypeptide FZD5-binding agent of the disclosure may be produced in recombinant sources, such as recombinant cell lines or transgenic animals. Techniques can be adapted for the production of single-chain antibodies, such as a scFv, specific to FZD5 (see, e.g. U.S. Pat. No. 4,946,778).

Alternatively, a polypeptidic FZD5-binding agent of the disclosure, such as a FZD5-binding antibody of the disclosure may be obtained by immunizing an animal with FZD5, or with a polypeptide comprising a suitable FZD5epitope, so as to generate the antibody in the animal's serum.

A FZD5-binding IgG antibody of the disclosure can be purified from a biological sample, such as serum, via techniques such as affinity chromatography using protein A or protein G (see, e.g. Wilkinson, 2000). Additionally or alternatively, FZD5, or a polypeptide comprising an epitope thereof, which is specifically bound by the FZD5-binding agent may be immobilized on a column to purify the FZD5-binding agent from a sample by immunoaffinity chromatography.

A FZD5-binding antibody fragment of the disclosure may be obtained from an antibody using conventional techniques. For example, F(ab')2 fragments can be generated by treating an antibody with pepsin. The resulting F(ab')2 fragment can be treated to reduce disulfide bridges to produce Fab' fragments.

Methods of producing polypeptidic FZD5-binding agents of the disclosure are described in further detail below.

As set forth above, in an embodiment, the FZD5-binding agent may be a bispecific antibody.

As used herein, bispecific antibodies are binding agents comprising two different antibody variable regions which confer binding specificities for at least two different antigens or two different epitopes of the same antigen.

The presently disclosed bispecific antibodies specifically bind FZD5 and another antigen or specifically bind different epitopes of FZD5. Optionally, the bispecific antibody binds FZD5 and a cell-surface protein, receptor or receptor subunit.

In another embodiment, the FZD5-binding agent is a bispecific antibody that targets, binds and/or engages immune cells such as T cells, macrophages or NK cells. According to this embodiment, the FZD5-binding agent is a bispecific antibody where one of the binding specificities is for FZD5 and the other binding specificity is for an antigen expressed on the surface of T cells, macrophages or NK cells. For example, the bispecific antibody may bind FZD5 and an immune cell receptor, such a receptor of a T cell, which when bound activates or inhibits activity of the immune cell.

Various techniques for making and isolating bispecific antibodies directly from recombinant cell culture have been described. For example, bispecific antibodies have been produced using leucine zippers (see, e.g. Kostelny et al., 1992), using "diabody" technology (see, e.g. Hollinger et al., 1993), and using single-chain Fv (scFv) dimers (see, e.g. Gruber et al., 1994).

A bispecific antibody that engages T cells may be referred to as a bispecific T-cell engager (BiTE). In one embodiment of the present disclosure, the bispecific antibody/BiTE specifically binds both FZD5 and the T cell co-receptor CD3 (also referred to herein as FZD5-binding/CD3-binding bispecific antibody). Accordingly, provided herein is a bispecific antibody/BiTE which comprises a FZD5-binding antibody variable region of the disclosure and a CD3-binding antibody variable region. Such bispecific antibodies/BiTEs allow targeting of a T cell to a cell, such as a cancer cell, expressing FZD5.

In a further embodiment, the bispecific antibody binds FZD5 and the NK cell surface receptor CD16.

As described above, the FZD5-binding agent may have any number of valencies and/or specificities. For example, a trispecific and/or trivalent FZD5-binding agent can be prepared (see, e.g. Tutt et al., 1991).

As further described above, embodiments of the FZD5-binding agents also include FZD5-binding chimeric antigen receptors (CARs).

Accordingly, provided herein is a chimeric antigen receptor comprising (i) a FZD5-binding agent of the disclosure and (i) one or more immune cell receptor signaling domains. In one embodiment, the CAR is a monomeric polypeptide which comprises a FZD5-binding scFv and a CAR intracellular signaling domain comprising a CD3-zeta intracellular signaling domain, and optionally further comprising one or more T cell costimulatory receptor intracellular signaling domains. In an additional embodiment, the FZD5-binding agent is a phage-Fab or phage-scFv, where the Fab or scFv specifically binds FZD5.

It can be desirable to modify a binding agent disclosed herein with respect to effector function, so as to enhance its effectiveness in binding/targeting FZD5-expressing cells and/or reducing levels of FZD5 in FZD5-expressing cells. For example, where the binding agent comprises an antibody Fc region, such as an antibody, cysteine residue(s) can be introduced into the COOH terminal of the Fc region, thereby allowing interchain disulfide bond formation between antibody monomers in this region. The homodimeric antibody thus generated can have improved internalization capability and/or increased complement-mediated cell killing and antibody-dependent cellular cytotoxicity (ADCC) (see, e.g. Caron et al., 1992; and Shopes, 1992). Alternatively, an antibody can be engineered that has dual Fc regions and can thereby have enhanced complement lysis and ADCC capabilities (see, e.g. Stevenson et al., 1989). Functional variants of the FZD5-binding agents described herein are also encompassed by the present disclosure. The term "functional variant" as used herein includes modifications or chemical equivalents of the amino acid and nucleic acid sequences disclosed herein that perform substantially the same function as the polypeptides or nucleic acid molecules disclosed herein in substantially the same way. For example, functional variants of polypeptides disclosed herein include, without limitation, conservative amino acid substitutions.

A "conservative amino acid substitution" as used herein, is one in which one amino acid residue is replaced with another amino acid residue are substitutions that change an amino acid to a different amino acid with similar biochemical properties (e.g. charge, hydrophobicity and size). Variants of polypeptides also include additions and deletions to the polypeptide sequences disclosed herein. In addition, variant nucleotide sequences include analogs and derivatives thereof. A variant of the binding agents disclosed herein include agents that bind to the same antigen or epitope as the binding agents.

In one embodiment, the present disclosure includes functional variants to the amino acid sequences disclosed herein. For example, functional variants of the amino acid sequences corresponding to the CDRs of antibody variable regions Fv-2898 to Fv-2936 (SEQ ID NOs: 35-179), functional variants of the framework regions and segments shown in Table 7 (SEQ ID NOs: 352-355 and 360-363) and functional variants of the light and heavy chain amino acid sequences of antibody IgG-2919 (SEQ ID NOs: 338 and 340) are provided.

In another embodiment, the present disclosure includes functional variants to the nucleic acid sequences that encode the FZD5-binding agents disclosed herein. In particular, functional variants of the nucleotide sequences encoding the CDRs of antibody variable regions Fv-2898 to Fv-2936 (SEQ ID NOs: 180-337), functional variants of the nucleotide sequences encoding the framework regions and segments shown in Table 7 (SEQ ID NOs: 356-359 and 364-367) and functional variants of the nucleotide sequences encoding the light and heavy chains of antibody IgG-2919 (SEQ ID NOs: 339 and 341) are provided. In addition, the functional variants include nucleotide sequences that hybridize to the nucleic acid sequences set out above, under at least moderately stringent hybridization conditions.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature ($Tm=81.5° C.-16.6$ (Log10 [Na+])$+0.41$ (% (G+C)$-$600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In some embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2× SSC/0.1% SDS at 60° C. Moderately stringent hybridization conditions include a washing step in 3× SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

In another embodiment, the variant amino acid sequences of the FZD5-binding agents comprise sequences having at least 50%, or at least 60%, or at least 70%, or at least 80%, or at least 90%, or at least 95% sequence identity to the framework regions and/or framework segments of SEQ ID NOS: 352-355 and/or SEQ ID NOS: 360-363. As used herein, the term "framework region" refers to amino acid sequences which are found between, and adjacent to, the CDRs.

In another embodiment, the variant nucleotide sequences encoding the FZD5-binding agents comprise sequences having at least 50%, or at least 60%, or at least 70%, or at least 80%, or at least 90%, or at least 95% sequence identity to the framework regions of SEQ ID NOs: 356-359 and/or SEQ ID NOs: 364-367. As used herein, reference to "framework regions" of a nucleotide sequence refers to the nucleotide sequence encoding the framework region of the corresponding heavy or light chain.

The term "sequence identity" as used herein refers to the percentage of sequence identity between two amino acid sequences or two nucleic acid sequences. To determine the percent identity of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. One non-limiting example of a mathematical algorithm utilized for the comparison of two sequences is the algorithm of Karlin and Altschul, 1990, modified as in Karlin and Altschul, 1993. Such an algorithm is incorporated into the NBLAST and XBLAST programs of Altschul et al., 1990. BLAST nucleotide searches can be performed with the NBLAST nucleotide program parameters set, e.g. for score=100, word-length=12 to obtain nucleotide sequences homologous to a nucleic acid molecules of the present disclosure. BLAST protein searches can be performed with the XBLAST program parameters set, e.g. to score-50, wordlength=3 to obtain amino acid sequences homologous to a protein molecule of the present invention. To obtain gapped alignments for comparison purposes, Gapped BLAST can be utilized as described in Altschul et al., 1997. Alternatively, PSI-BLAST can be used to perform an iterated search which detects distant relationships between molecules. When utilizing BLAST, Gapped BLAST, and PSI-Blast programs, the default parameters of the respective programs (e.g. of XBLAST and NBLAST) can be used (see, e.g. the NCBI website). Another non-limiting example of a mathematical algorithm utilized for the comparison of sequences is the algorithm of Myers and Miller, 1988. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

Nucleic Acids and Vectors

Also provided are nucleic acids encoding the antibody variable regions described herein and nucleic acids encoding polypeptides comprising these antibody variable regions. As used herein, the term "nucleic acids" includes isolated nucleic acids.

In particular, nucleic acids encoding the CDR regions of antibody variable regions Fv-2898 to Fv-2936 as set out in SEQ ID NOs: 180-337 are provided, nucleic acids encoding the framework regions and segments shown in Table 7 (SEQ ID NOs: 356-359 and 364-367) and nucleic acids encoding the light and heavy chains of antibody IgG-2919 (SEQ ID NOs: 339 and 341) are provided.

Polypeptidic binding agents disclosed herein can be expressed by a vector containing a nucleic acid encoding the polypeptide of interest using methods which are well known and routinely practiced in the art. Accordingly, the present disclosure also provides a vector expressing any of the nucleic acids described herein.

The polypeptidic binding agents can be prepared by constructing a nucleic acid encoding a polypeptidic binding agent, inserting the construct into an expression vector, and then expressing it in appropriate host cells. Vectors useful for expressing the polypeptidic binding agents disclosed herein are well known in the art. In one embodiment, the vector includes suitable translation initiation and termination signals in operable reading phase with a functional promoter and can comprise one or more phenotypic selectable markers and an origin of replication to ensure maintenance of the vector and, if desirable, to provide amplification within the host. In addition to vectors, the nucleic acids of the present disclosure can be delivered to a cell or a subject via any other method known in the art including, but not limited to, liposomes, naked DNA, adjuvant-assisted DNA, gene gun, catheters, etc.

Monoclonal Polypeptides/Monoclonal Antibodies

As described above, the FZD5-binding agent can be a polypeptide comprising a FZD5-binding antibody variable region, such as an antibody specifically comprising antibody variable region Fv-2898 to Fv-2936. Accordingly, the disclosure further provides a monoclonal polypeptidic FZD5-binding agent of the disclosure, such as a monoclonal FZD5-binding antibody of the disclosure.

As used herein, a "monoclonal" polypeptidic FZD5-binding agent of the disclosure refers to a population of identical polypeptidic FZD5-binding agent molecules. For example, in the case of a monoclonal polypeptidic FZD5-binding agent of the disclosure comprising a FZD5-binding antibody variable region, such as a monoclonal FZD5-binding antibody of the disclosure, the CDRs are identical in all the molecules of the population. Various procedures known within the art may be used for the production of monoclonal polypeptides, such as monoclonal antibodies of the disclosure (see, for example, Greenfield, 2013). Monoclonal antibodies are commonly alternatively referred to using the abbreviations "mAb" or "MAb".

Monoclonal antibodies can be made by recombinant DNA methods, such as those described in U.S. Pat. No. 4,816,567. DNA encoding the monoclonal antibodies and antigen-binding fragments thereof can be readily isolated and sequenced using conventional procedures (e.g. by using oligonucleotide probes that are capable of binding specifically to genes encoding the heavy and light chains of murine antibodies). The hybridoma cells serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

Monoclonal antibodies may also be generated, e.g. by immunizing an animal with FZD5, such as, for example, murine, rat or human FZD5 or an immunogenic fragment, derivative or variant thereof. Alternatively, the animal is immunized with cells transfected with a vector containing a nucleic acid molecule encoding FZD5 that is expressed and associated with the surface of the transfected cells. Alternatively, the antibodies are obtained by screening a library that contains antibody or antigen binding domain sequences for binding to FZD5. This library is prepared, e.g. in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to FZD5.

Monoclonal antibodies may be prepared, for example, using hybridoma methods (see, for example, Kohler and Milstein, 1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Affinity

Non-covalent interactions occur between an immunoglobulin molecule and an antigen for which the immunoglobulin is specific. The strength, or affinity of immunological binding interactions can be expressed in terms of the dissociation constant ($K_D$) of the interaction, wherein a smaller $K_D$ represents a greater affinity. The terms "dissociation constant" and "affinity" are used interchangeably herein to refer to $K_D$. Immunological binding properties of specific polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" (Kon) and the "off rate constant" (Koff) can be determined by calculation of the concentrations and the actual rates of association and dissociation (see, e.g. Malmqvist, 1993). The ratio of Koff/Kon enables the cancellation of all parameters not related to affinity, and is equal to the dissociation constant $K_D$ (see, e.g. Davies et al., 1990).

A bivalent FZD5-binding agent disclosed herein is said to bind to a Frizzled protein when the $K_D$ is ≤1 micromolar to about 1 pM, ≤100 nM to about 1 pM, ≤10 nM to about 1 pM, 1 nM to about 1 pM, 100 pM to about 1 pM, or ≤10 pM to about 1 pM, as measured by assays such as surface plasmon resonance (SPR) analysis, radioligand binding assays or similar assays known to those skilled in the art. As described above, in a particular embodiment, the FZD5-binding agent binds FZD5 with an affinity ($K_D$)≤200 pM.

In other embodiments, a bivalent FZD5-binding agent disclosed herein binds FZD5 with an affinity ($K_D$) less than or equal to 1 nM, less than or equal to 200 pM, less than or equal to 110 pM, less than or equal to 88 pM or less than or equal to 10 pM.

In various embodiments, a bivalent FZD5-binding agent further has one or more Frizzled protein-binding affinities selected from: a FZD8-binding affinity ($K_D$) selected from an affinity less than or equal to 60 pM, an affinity less than or equal to 50 pM, an affinity less than or equal to 45 pM, an affinity less than or equal to 42 pM, and an affinity less than or equal to 25 pM.

In another embodiment, a bivalent FZD5-binding agent disclosed herein further has a FZD1-binding affinity ($K_D$) less than or equal to 1.5 pM.

In a further embodiment, a bivalent FZD5-binding agent disclosed herein further has a FZD2-binding affinity ($K_D$) less than or equal to 910 pM.

In an additional embodiment, a bivalent FZD5-binding agent disclosed herein further has a FZD7-binding affinity ($K_D$) less than or equal to 500 pM.

A monovalent FZD5-binding agent disclosed herein (i.e. which has single FZD5-binding site, such as a single FZD5-binding antibody variable region, e.g. a scFv or a Fab) is said to specifically bind FZD5 when the affinity ($K_D$) of the binding of the FZD5-binding agent in bivalent form is 1 micromolar. Methods for joining monovalent binding agents of the disclosure for generating suitable bivalent forms thereof are well known in the art (e.g. where the monovalent agent comprises a single antibody variable region, production of bivalent antibodies/F(ab')2 comprising two copies of the antibody variable region; or e.g. using suitable linkers, such as polypeptide linkers, nucleic acid linkers or chemically synthesized linkers).

The disclosure also provides a FZD5-binding agent which binds to the same epitope as any one of the FZD5-binding agents disclosed herein comprising an antibody variable region.

As used herein, the term "epitope" refers to the specific site or specific combination of sites/amino acids on an antigen that are bound by the antibody variable regions disclosed herein, for example, unmodified or modified (e.g. post-translationally modified, e.g. glycosylated) amino acid residues of human FZD5, the minimal polypeptide segment of human FZD5 encompassing these amino acid residues, or any combination of polypeptide segments of human FZD5 encompassing these amino acid residues. Epitopic determinants usually consist of molecules such as amino acids or sugar side chains and usually have specific three dimensional structural characteristics, as well as specific charge characteristics.

In various embodiments, the FZD5-binding agent binds any one of various portions or epitopes of FZD5. In one embodiment, the FZD5-binding agent binds the Ala27-Pro167 segment of FZD5 (SEQ ID NO: 368) and the epitope is located in the Ala27-Pro167 segment of FZD5.

In a further embodiment, the FZD5-binding agent binds the cysteine-rich domain (CRD) of FZD5 and the epitope is located in the CRD of FZD5.

Any one of various methods known in the art can be used to identify a FZD-binding agent which specifically binds a FZD5 epitope bound by the FZD5-binding agents described herein comprising an antibody variable region. A person skilled in the art will appreciate that binding assays such as a competition binding assay can be used for this purpose. Those skilled in the art will recognize that it is possible to determine, without undue experimentation, if a binding agent specifically binds a FZD5 epitope bound by a FZD5-binding agent disclosed herein comprising an antibody variable region by ascertaining whether the binding agent being tested prevents the FZD5-binding agent from binding to human FZD5. If the binding agent being tested competes with the FZD5-binding agent, as shown by a decrease in binding to human FZD5 by the FZD5-binding agent, then the binding agent binds to the same epitope as the FZD5-binding agent. Methods for the testing the specificity of binding agents include, but are not limited to, enzyme linked immunosorbent assay (ELISA) and other immunologically mediated techniques known within the art.

Detection Agents

In one embodiment, the FZD5-binding agent is labeled with a detection agent. As used herein, the term "detection agent" refers to any agent that allows the presence of the FZD5-binding agent to be detected and/or quantified. Examples of detection agents include, but are not limited to, peptide tags, enzymes (for example, HRP or alkaline phosphatase), proteins (for example phycoerythrin or biotin/streptavidin), magnetic particles, chromophores, fluorescent molecules, chemiluminescent molecules, radioactive labels and dyes. The FZD5-binding agent may be labeled directly or indirectly with the detection agent.

Conjugates

The present disclosure also provides a conjugate comprising (1) the FZD5-binding agent attached to (2) an effector agent.

In one embodiment, the conjugate is an immunoconjugate wherein the FZD5-binding agent comprises an antibody variable region.

In one embodiment, the effector agent is a label, which can generate a detectable signal, directly or indirect. Examples of labels include radioactive isotopes (i.e., a radioconjugate).

In another embodiment, the effector agent is a therapeutic agent. Therapeutic agents include, but are not limited to, cancer therapeutic agents/antineoplastic agents. In yet another embodiment, the therapeutic agent is a toxin.

The term "cancer therapeutic agent" or "antineoplastic agent" is used herein to refer to agents that have the functional property of inhibiting growth of, of killing, of halting or reversing the cancer-specific differentiation of, and/or of ameliorating a pathogenic effect of FZD5-expressing cancer cells.

The toxin may be an enzymatically active toxin of bacterial, fungal, plant, or animal origin, or a fragment thereof. Toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

Radioconjugated FZD5-binding agents of the disclosure, such as antibodies of the disclosure, may be employed to bind radionuclides to FZD5-expressing cells, for example to visualize the cells or as a cytotoxic treatment of the cells. A variety of radionuclides are available for the production of radioconjugated antibodies. Examples include 212Bi, 1311, 1311n, 90Y, and 186Re.

Those of ordinary skill in the art will recognize that a large variety of possible moieties can be coupled to the polypeptidic FZD5-binding agents of the disclosure, such as those comprising an antibody variable region (e.g. antibodies or antibody fragments comprising a FZD5-binding antibody variable region) (see, for example, Cruse and Lewis, 1989, the entire contents of which are incorporated herein by reference). Coupling may be accomplished by any chemical reaction that will bind a moiety and a FZD5-binding agent of the disclosure, so long as these retain their respective activities/characteristics for the intended use thereof. This linkage can include many chemical mechanisms, for instance covalent binding, affinity binding, intercalation, coordinate binding and complexation.

For example, conjugates of a polypeptidic FZD5-binding agent of the disclosure, such as an antibody and an effector agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987).

Carbon-14-labeled 1-isothiocyanatobenzyl-3-methyldi-ethylene triaminepentaacetic acid (MX-DTPA) is an exemplary chelating agent for conjugation of radionucleotide to the antibody (see, e.g. WO94/11026).

Pharmaceutical Compositions

The disclosure also provides pharmaceutical compositions comprising a FZD5-binding agent or conjugate described herein as an active ingredient and a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin.

A pharmaceutical composition is formulated to be compatible with its intended route of administration. Examples of routes of administration include parenteral, e.g. intravenous, intradermal, subcutaneous, oral (e.g. inhalation), transdermal (i.e., topical), transmucosal, and rectal administration.

In one embodiment, the active ingredient is prepared with a carrier that will protect it against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

In one embodiment, oral or parenteral compositions are formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with the required pharmaceutical carrier. The specification for the dosage unit forms are dictated by and directly dependent on the unique characteristics of the active ingredient and the particular therapeutic effect to be achieved, and the limitations inherent in the art of preparing such an active ingredient for the treatment of individuals.

The formulation can also contain more than one active ingredient as necessary for the particular indication being treated, optionally those with complementary activities that do not adversely affect each other. Alternatively, or in addition, the pharmaceutical composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Methods and Uses

The inventors have shown that both human FZD5 (Gen-Bank Protein Accession NP_003459.2) and human Wnt7B are required for the growth of RNF43-mutant pancreatic cancer cell lines (Example 3). Further, anti-FZD5 antibodies IgG-2910, IgG-2916, IgG-2919, IgG-2920, IgG-2921 and IgG-2929 suppress growth of multiple RNF43-mutant pancreatic cancer cell lines.

Accordingly, the present disclosure provides methods for treating cancer comprising administering an effective amount of a FZD5-binding agent or pharmaceutical composition disclosed herein to an animal or cell in need thereof, wherein the cancer is associated with one or more of: a loss of function of a negative regulator of Wnt signaling, elevated levels of FZD5 signaling and elevated levels of cell surface-expressed FZD5. The disclosure also provides a use of an effective amount of a FZD5-binding agent or pharmaceutical composition disclosed herein for treating or preventing cancer, wherein the cancer is associated with one or more of: a loss of function of a negative regulator of Wnt signaling, elevated levels of FZD5 signaling and elevated levels of cell surface-expressed FZD5. Further disclosed is a use of a FZD5-binding agent or pharmaceutical composition disclosed herein in the preparation of a medicament for treating or preventing cancer, wherein the cancer is associated with one or more of: a loss of function of a negative regulator of Wnt signaling, elevated levels of FZD5 signaling and elevated levels of cell surface-expressed FZD5. The disclosure further provides an effective amount of an a FZD5-binding agent or pharmaceutical composition disclosed herein for use in treating or preventing cancer, wherein the cancer is associated with one or more of: a loss of function of a negative regulator of Wnt signaling, elevated levels of FZD5 signaling and elevated levels of cell surface-expressed FZD5 In one embodiment, the negative regulator of Wnt signaling is RNF43.

As used herein, the term "associated with a loss of function of a negative regulator of Wnt signaling" means that the activity or presence of the negative regulator of Wnt signaling in the cancer cell or cell line is decreased compared to a cancer cell or cell line that is not associated with a loss of function of a negative regulator of Wnt signaling. In some embodiments, the cancer cell or cell line has a loss of function mutation or other deleterious mutation in RNF43. In other embodiments, the cancer cell or cell line is a RNF43 null mutant.

RNF43 mutations in various cancers are known, including, without limitation, in colorectal adenocarcinomas and endometrial carcinomas; in endometrioid carcinoma of the uterus, mucinous ovarian tumors, liver fluke-associated cholangiocarcinoma, pancreatic cancers, stomach cancers, liver cancers, renal cancers and lung cancers (Waddell, et al., 2015; Ryland et al., 2015; Wang et al., 2014; Giannakis et al., 2014; Ivanov et al., 2007; Koo et al., 2012; Hao et al., 2012).

In various embodiments, the cancer is colorectal cancer, endometrial cancer, ovarian cancer, cholangiocarcinoma, pancreatic cancer, stomach cancer, liver cancer, breast cancer, renal cancer or lung cancer.

Examples of pancreatic cell lines associated with a loss of function of a negative regulator of Wnt signaling include, but are not limited to, HPAFII, ASPC1, PATU8988S, CAPAN2, IMIMPC2 and GP2A.

The disclosure further provides a method for treating a disease or disorder associated with FZD5 binding, activation and/or activity, comprising administering an effective amount of a FZD5-binding agent or pharmaceutical composition disclosed herein to an animal or cell in need thereof. The disclosure also provides a use of an effective amount of a FZD5-binding agent or pharmaceutical composition disclosed herein for treating or preventing a disease or disorder associated with FZD5 binding, activation and/or activity.

Further disclosed is a use of a FZD5-binding agent or pharmaceutical composition disclosed herein in the preparation of a medicament for treating or preventing a disease or disorder associated with FZD5 binding, activation and/or activity. The disclosure further provides an effective amount of a FZD5-binding agent or pharmaceutical composition disclosed herein for use in treating or preventing a disease or disorder associated with FZD5 binding, activation and/or activity. Examples of diseases or disorders associated with FZD5 binding, activation and/or activity include cancer (for example RNF43-mutant pancreatic cancer) as disclosed herein.

The disclosure also provides a use of an effective amount of a conjugate disclosed herein for treating or preventing cancer, wherein the cancer is associated with one or more of: a loss of function of a negative regulator of Wnt signaling, elevated levels of FZD5 signaling and elevated levels of cell surface-expressed FZD5. The disclosure also provides a use of the conjugate in the preparation of a medicament for treating or preventing cancer, wherein the cancer is associated with one or more of: a loss of function of a negative regulator of Wnt signaling, elevated levels of FZD5 signaling and elevated levels of cell surface-expressed FZD5. The disclosure further provides a method of treating or preventing cancer comprising administering an effective amount of the conjugate to an animal or cell in need thereof, wherein the cancer is associated with one or more of: a loss of function of a negative regulator of Wnt signaling, elevated levels of FZD5 signaling and elevated levels of cell surface-expressed FZD5. Also provided is an effective amount of a conjugate disclosed herein for use in treating or preventing cancer, wherein the cancer is associated with one or more of: a loss of function of a negative regulator of Wnt signaling, elevated levels of FZD5 signaling and elevated levels of cell surface-expressed FZD5.

Still further provided is a method of treating or preventing a cancer comprising administering an effective amount of an inhibitor of binding between FZD5 and Wnt7B to a subject in need thereof, wherein the cancer is associated with one or more of: a loss of function of a negative regulator of Wnt signaling, elevated levels of FZD5 signaling and elevated levels of cell surface-expressed FZD5. Also provided is use of an effective amount of an inhibitor of binding between FZD5 and Wnt7B for treating or preventing cancer in a subject in need thereof, wherein the cancer is associated with one or more of: a loss of function of a negative regulator of Wnt signaling, elevated levels of FZD5 signaling and elevated levels of cell surface-expressed FZD5. Even further provided is use of an effective amount of an inhibitor of binding between FZD5 and Wnt7B in the manufacture of a medicament for treating or preventing cancer in a subject in need thereof, wherein the cancer is associated with one or more of: a loss of function of a negative regulator of Wnt signaling, elevated levels of FZD5 signaling and elevated levels of cell surface-expressed FZD5. Yet further provided is an effective amount of an inhibitor of binding between FZD5 and Wnt7B for use in treating or preventing cancer in a subject in need thereof, wherein the cancer is associated with one or more of: a loss of function of a negative regulator of Wnt signaling, elevated levels of FZD5 signaling and elevated levels of cell surface-expressed FZD5.

In one embodiment, the inhibitor inhibits cellular production of FZD5 or Wnt7B, optionally by CRISPR/Cas-mediated knockout of the gene that encodes it.

As used herein, a "cancer associated with cell surface expression of FZD5" refers to a cancer cell, or a plurality of cancer cells, that express FZD5 on the cell surface. The phrase "elevated levels" as used herein refers to an increase of at least 10%, 20%, 30%, 40%, 50% or more of expression or signaling of FZD5 on the cell surface compared to levels of surface expression of FZD5 in non-cancerous cells of the cell type from which the cancer cells originated, such as those derived from the subject, or those of a population of subjects from which a reference level is established.

As used herein, the terms "subject" and "animal" include all members of the animal kingdom, preferably a mammal, more preferably a human being. In one embodiment, the subject is a patient.

The term "a cell" includes a single cell as well as a plurality or population of cells.

Administration of an "effective amount" of a FZD5-binding agent, conjugate and/or pharmaceutical composition disclosed herein is defined as an amount effective, at dosages and for periods of time necessary to achieve the desired result. For example, an effective amount of a substance may vary according to factors such as the disease state, age, sex, and weight of the individual, and the ability of the antibody or composition to elicit a desired response in the individual. The dosage regime may be adjusted to provide the optimum therapeutic response. For example, several divided doses may be administered daily or the dose may be proportionally reduced as indicated by the exigencies of the therapeutic situation.

An effective amount of an antibody of the disclosure relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the disclosure may be, by way of non-limiting example, from about 0.1 mg kg body weight to about 50 mg/kg body weight. Common dosing frequencies may range, for example, from twice daily to once a week.

As used herein, "treating or preventing" includes, but is not limited to, reversing, alleviating or inhibiting the progression of a disease or disorder or symptoms or conditions associated with a disease or disorder. Preventing includes preventing occurrence of a disease or disorder or symptoms or conditions associated with a disease or disorder or preventing worsening of the severity of a disease or disorder or symptoms or conditions associated with a disease or disorder. Accordingly, "treating or preventing" optionally includes the prophylactic treatment of a subject in order to prevent or reduce the incidence or recurrence of a disease or disorder or symptoms or conditions associated with a disease or disorder.

In one embodiment, the FZD5-binding agents, conjugates and pharmaceutical compositions disclosed herein are used in combination with other therapies. Accordingly, the disclosure provides a method of preventing or treating a disease or disorder using the FZD5-binding agents, conjugates or pharmaceutical compositions disclosed herein in combination with at least one additional therapy. The other therapy may be administered prior to, overlapping with, concurrently, and/or after administration of the FZD5-binding agents, conjugates or pharmaceutical compositions disclosed herein. When administered concurrently, the FZD5-binding agents, conjugates or pharmaceutical compositions disclosed herein and the other therapeutic may be administered in a single formulation or in separate formulations, and if separately, then optionally, by different modes of administration. The combination of one or more FZD5-binding agents, conjugates or pharmaceutical compositions disclosed herein and one or more other therapies may synergistically act to combat a disease or disorder.

For example, the combination therapy can include one or more FZD5-binding agents, conjugates and pharmaceutical compositions coformulated with, and/or coadministered with, one or more additional therapeutic agents, e.g., one or more cytokine and growth factor inhibitors, immunosuppressants, anti-inflammatory agents, metabolic inhibitors, enzyme inhibitors, anti-neoplastic agents, and/or cytotoxic or cytostatic agents. Such combination therapies may advantageously utilize lower dosages of the administered therapeutic agents, thus avoiding possible toxicities or complications associated with the various monotherapies.

Detecting FZD5-Expressing Cells

The FZD5-binding agents, conjugates and pharmaceutical compositions of the present disclosure are useful for detecting cells that express FZD5. Accordingly, the disclosure provides a use of the FZD5-binding agents described herein for targeting, binding and/or detecting FZD5-expressing cells. Optionally, the cells are cancer cells, including, but not limited to, colorectal cancer cells, endometrial cancer cells, ovarian cancer cells, cholangiocarcinoma cells, pancreatic cancer cells, stomach cancer cells, liver cancer cells, breast cancer cells, renal cancer cells or lung cancer cells. In another embodiment, the cells are associated with a loss of function of a negative regulator of Wnt signaling. In further embodiments, the cells having a loss of function mutation or other deleterious mutation in RNF43. In other embodiments, the cells are RNF43 null mutants.

As used herein, the term "associated with a loss of function of a negative regulator of Wnt signaling" means that the activity or presence of the negative regulator of Wnt signaling in the cancer cell or cell line is decreased compared to a cancer cell or cell line that is not associated with a loss of function of a negative regulator of Wnt signaling. In some embodiments, the cancer cell or cell line has a loss of function mutation or other deleterious mutation in RNF43. In other embodiments, the cancer cell or cell line is a RNF43 null mutant.

In one embodiment, the FDZ5-binding agents, conjugates, and pharmaceutical compositions described herein are useful for targeting, binding and/or detecting cell surface expression of FDZ5-expressing cells.

In another embodiment, the FDZ5-binding agents, conjugates and pharmaceutical compositions described herein are useful for targeting, binding, detecting and/or localizing FDZ5.

In another embodiment, the FDZ5-binding agents, conjugates and pharmaceutical compositions described herein are useful for targeting, binding and/or detecting FDZ5 in cell lysates.

In yet another embodiment, the FDZ5-binding agents, conjugates and pharmaceutical compositions described herein are useful for detecting and/or quantitating levels of expression of FDZ5 in a sample, optionally in a FDZ5 expressing cell. In another embodiment, the FDZ5-binding agents, conjugates and pharmaceutical compositions are useful for detecting and/or quantitating cell surface FDZ5 levels.

In general, the use of binding agents for detection of analytes, such as FDZ5 protein, is well known in the art and may be achieved through the application of numerous approaches. These methods are generally based upon the detection of a label or marker, such as radioactive, fluorescent, biological and enzymatic tags. Examples of methods include, but are not limited to, Western blotting, enzyme linked immunosorbent assay (ELISA), immunofluorescence, immunohistochemistry and flow cytometry.

Targeting FDZ5-Expressing Cells to Immune Cells

Further, the FDZ5-binding agents, conjugates and pharmaceutical compositions of the present disclosure are useful for engaging, targeting and/or binding cells of the immune system.

In various embodiments, the FZD5-binding agent is an antibody or a Fab.

In further various embodiments the FZD5-binding agent is Fab-2919 or IgG-2919.

In one embodiment, as described above, the FDZ5-binding agent is a bispecific antibody where one of the binding specificities is for FDZ5 and the other binding specificity is for an antigen expressed on an immune cell such as a T cell, macrophage or NK cell. As described above, one example of a bispecific antibody that targets T cells is a bispecific T-cell engager (BiTE).

In another embodiment described above, the FDZ5-binding agent is a FDZ5-binding chimeric antigen receptor (CAR) which includes an FDZ5-binding agent of the disclosure, such as an FDZ5-binding scFv as its antigen-binding/targeting domain.

Accordingly, the antibodies, Fabs, bispecific antibodies and chimeric antigen receptors described herein are useful for targeting immune effector cells to FDZ5-expressing cells.

Also provided are methods for targeting FDZ5-expressing cells comprising exposing the FDZ5-expressing cells to an immune effector cell expressing a CAR of the disclosure, or to a combination of a bispecific antibody of the disclosure and an immune effector cell specifically bound by the bispecific antibody.

Targeting immune effector cells to FDZ5-expressing cells through these methods may be useful for eliminating, and/or shifting the phenotype of, FDZ5-expressing cells from a cancerous phenotype towards a less cancerous or non-cancerous phenotype. In addition, targeting immune effector cells to FDZ5-expressing cells may be useful for treating diseases where FDZ5 is expressed or overexpressed such as cancer.

Diagnostic Methods

The FDZ5-binding agents disclosed herein are useful in the detection/quantitation of FDZ5 in patient samples or in control samples of healthy individuals and accordingly may be useful diagnostics. For example, the binding agents of the disclosure can be used to detect/quantitate total cellular expression of FDZ5 and/or cell-surface expressed FDZ5. As used herein, the term "diagnostics" encompasses screening, stratification, monitoring and the like.

In one embodiment, the FDZ5-binding agents are used to detect FDZ5-expressing cells, optionally cancer cells such as colorectal cancer cells, endometrial cancer cells, ovarian cancer cells, cholangiocarcinoma cells, pancreatic cancer cells, stomach cancer cells, liver cancer cells, breast cancer cells, renal cancer cells or lung cancer cells.

In another embodiment, the FDZ5-binding agents are used for detecting/quantitating expression of FDZ5. In another embodiment, the FDZ5-binding agents described herein can be used to detect/quantitate expression of FDZ5 in a sample.

For example, FDZ5-binding agents of the disclosure, such as the antibodies and antibody fragments of the disclosure, may be used for practicing any one of various assays, e.g.

immunofluorescence, flow cytometry or ELISAs, to detect/quantitate FDZ5 levels in a sample.

In one embodiment, the sample is a patient sample, such as a cancer sample from a cancer patient. Alternately, the sample may be a control sample from a healthy individual. Embodiments of the sample include but are not limited to, a sample of cultured cells, cultured cell supernatant, cell lysate, serum, blood plasma, biological fluid or biological tissue. In other embodiments, the sample is obtained from a cancer. In certain embodiments, the sample is a biopsy sample.

Screening Assays

The disclosure also provides methods (also referred to herein as "screening assays") for identifying modulators, i.e., test agents (e.g. peptides, peptidomimetics, small molecules or other drugs) that modulate or otherwise interfere with the binding of a protein disclosed herein with FZD5.

Accordingly, the disclosure also provides a method of screening for compound that inhibit binding between FZD5 and Wnt7B, comprising:

(i) measuring binding between FZD5 and Wnt7B;

(ii) exposing FZD5 and WNT7B to a test agent; and (iii) determining if the test agent inhibits binding between FZD5 and Wnt7B.

The test agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection (see, e.g. Lam, 1997).

In one embodiment, the test agent inhibits binding between FZD5 and Wnt7B by at least 5%, 10%, 25%, 75% or 100%. Methods of determining protein-protein binding are well known in the art.

The following non-limiting examples are illustrative of the present disclosure:

EXAMPLES

Example 1: Materials and Methods

Plasmids: pLCKO lentiviral vector used for knockout (TKO) library construction and expression of individual gRNAs was constructed as described previously (Hart et al., 2015). Briefly, single guide RNA (sgRNA) scaffold was amplified from px330 (Addgene 42230) and cloned into pLKO.TRC005 lentiviral vector (Broad Institute, Cambridge, MA) using AgeI/EcoRI restriction sites. BfuAI sites were added at the 5' end of the sgRNA scaffold for cloning the TKO library or individual gRNA target sequences. Lenti Cas9-2A-BsdR vector used to generate Cas9 stable expression cell lines was constructed as described previously (Hart et al., 2015). Briefly, lentiCRISPR pXPR_001 (Addgene 49535) was modified through removal of the sgRNA scaffold region through NdeI/EcoRI digest and blunt ends generation using Large Klenow Fragment (NEB). 2A-puro was replaced with 2A-BsdR by PCR using the NheI/MluI sites. Each of the 10 human Frizzled cysteine rich domains (CRDs) were cloned into the lentiviral expression plasmid pLenti-puro in the following cassette: FZD_CRD-MYC-GPI.

Cell Culture: HPAFII, PaTU-8988s, PANC-1, HEK293T and mouse L-cell cell lines were maintained in DMEM containing 4.5 g/L D-glucose, L-glutamine (ThermoFisher #11965) and supplemented with 10% FBS (ThermoFisher) and Penicillin/Streptomycin (ThermoFisher #15140-163).

AsPC-1 and BxPC-3 cell lines were maintained in RPMI 1640 with L-glutamine (ThermoFisher #11875) supplemented with 10% FBS and Penicillin/Streptomycin. CHO cells were maintained in DMEM/F12 (ThermoFisher #11320-033), supplemented with 10% FBS and penicillin/streptomycin. All cell lines were maintained at 37 degrees centigrade and 5% $CO_2$. For puromycin selection cells were selected in medium containing 2 micrograms/ml puromycin dihydrochloride (BioShop Canada #PUR333). For blasticidin selection cells were selected in medium containing 10 micrograms/ml (HPAFII), 8 micrograms/ml (PaTu-8988s), 5 micrograms/ml (PANC-1), 2 micrograms/ml (BxPC-3) or 1 micrograms/ml (AsPC-1) of blasticidin hydrochloride (BioShop Canada #BLA477)

gRNA Library Design and Construction: gRNA library design and construction were described previously (Hart et al., 2015). Briefly, ~90k gRNA candidate sequences were chosen based on minimal off-target sites and optimized cleavage efficiency. The library was designed to target as many protein-coding exons as possible, with a maximum of 6 gRNA/gene. This yielded a library targeting 17232 genes. The library was synthesized in a pooled oligo array of 58-mers (CustomArray), with each gRNA target flanked by BfuAl restriction sites (oligo sequence below). The oligo pool was PCR amplified (primers listed below), purified (Qiaquick nucleotide removal kit, Qiagen #28304) and ligated into pLCKO in a one-step digestion/ligation reaction with BfuAl and T4 ligase (NEB). Ligation products were purified with Qiaquick nucleotide removal kit (Qiagen #28304), transformed in Electromax Stbl4 competent cells (ThermoFisher #11635-018) and grown on LB-Carbenicillin (100 micrograms/ml, ThermoFisher #10177-012) plates. >5.8E7 colonies were harvested, for ~650-fold library coverage. Plasmid DNA was extracted from colonies with QIAfilter Plasmid Giga Kit (Qiagen #12291). Oligo array template:

```
                                    (SEQ ID NO: 1)
5'-AGAGAACCTGCAGAGACCGnnnnnnnnnnnnnnnnnnnnnGTTTAGAG

GCAGGTAGAGA-3'
```

Primers for Amplifying CRISPR Library:
Forward:

```
                                    (SEQ ID NO: 2)
5'-TGTCAGTTGTCATTCGCGAAAAAGAGAACCTGCAGAGACC-3'
```

Reverse:

```
                                    (SEQ ID NO: 3)
5'-GTCACTGACGCGGTTTTGTAGATCTCTACCTGCCTCTAAA-3'
```

Lentiviral Production: Lentivirus production of the gRNA library was completed as described previously (Hart et al., 2015). Briefly, 9 million HEK293T cells were seeded per 15 cm plate. 24-hours post seeding, cells were transfected with a mixture of 14 micrograms pLCKO gRNA library plasmid pool, 16 micrograms packaging vector psPAX2 (Addgene 12260), 1.56 micrograms envelope vector pMD2.G (Addgene 12259), 93.6 microliters X-treme Gene transfection reagent (Roche #06366236001) and 1.4 ml Opti-MEM medium (ThermoFisher #31985-070), per plate. 24 hours post transfection medium was replaced with DMEM, 1.1 g/100 ml BSA, Penicillin/Streptomycin. Viral media was harvested at 48 and 72 hours post transfection by centrifugation at 1500 RPM for 5 minutes at 4 degrees centigrade, aliquoted and filtered before freezing at −80 degrees centigrade. For routine lentiviral production, 3.5 million HEK293T cells were seeded in 10 cm plates 24 hours before transfection. Five micrograms of lentiviral delivery vector (pLCKO or LentiCas9), 4.5 micrograms psPAX2 and 0.5 micrograms pMD2.G were transfected per plate with Lipofectamine 2000 (ThermoFisher #11668-019), following manufacturers protocol. Twenty-four hours post transfection medium was changed. Viral media was harvested 48 hours post transfection by centrifugation at 2000 rcf for 5 minutes followed by filtering through a 0.2 micron syringe filter.

Lentiviral Transduction and MOI Determination: Cells were seeded at low density (for three days growth) in medium containing between 0.125% and 8% viral medium and 8 micrograms/ml Polybrene (Sigma #H9268-5G). 24 hours post transduction, cells were placed in selective medium containing puromycin. Multiplicity of infection (MOI) determination was done by comparing cell counts in control and puromycin containing wells, transduced at various viral medium concentrations after 48 hours puromycin selection.

Lentiviral gRNA Library Essentiality Screen in HPAF-11: HPAF-II cell line was transduced with Lenti Cas9-2A-BsdR as described above and selected in 10 micrograms/ml blasticidin. A polyclonal stable cell line was established and single clones were isolated by limited dilution. Clones were expanded and screened for Cas9 expression via western blot and cleavage activity with pLCKO delivered gRNAs (data not shown).

The selected HPAFII Cas9-2A-BsdR clone was transduced with the 90k gRNA library at an MOI of 0.3 and a library fold-coverage of 300× (~27 million transduced cells). 72 hours post-infection (and 48 hours post puromycin selection) cells were split into two independent replicate populations of minimum 200-fold library coverage (18 million cells). In addition, TO reference samples were collected (18 million cells) for genomic DNA extraction. Replicate populations were passaged in parallel every four days, with 18 million cells seeded over five 15 cm plates per population. Samples were collected at T15, T27, T31 and T35, at approximately 10, 18, 21 and 23 doublings respectively.

Screen sample preparation for sequencing: Genomic DNA was extracted and prepared for PCR as described previously (Blakely et al., 2011). Briefly, genomic DNA was extracted with QiaAmp DNA Maxi Kit (Qiagen #51192), following manufacturers protocol. Following genomic DNA extraction, the DNA was ethanol precipitated and resuspended in 10 mM Tris-HCl pH8.5 at a concentration greater than 500 ng/microliter.

2-steps nested PCR amplification of gRNA target sequences for Illumina sequencing was completed as described previously (Hart et al., 2015). Briefly, 50 micrograms of genomic DNA per sample was used as template for amplification using primers listed below. This was completed with KAPA HiFi polymerase (Kapa Biosystems #KK2602) and split over ten 50 microliter reactions. After amplification, reactions were pooled and 5 microliters was used as template for amplification with primers containing Illumina TruSeq adapters. Final PCR products were gel purified with PureLink combo kit (ThermoFisher #K2200-01). Sequencing was completed with Illumina HiSeq2500, as described previously (Hart et al., 2015).

Step 1 PCR Forward:

```
                                    (SEQ ID NO: 342)
    5'-AGGGCCTATTTCCCATGATTCCTT-3'
```

Step 1 PCR Reverse:

```
                                    (SEQ ID NO: 343)
    5'-TCAAAAAAGCACCGACTCGG-3'
```

TruSeq Adapters with i5 Barcodes:
Forward:

```
                                    (SEQ ID NO: 344)
5'-AATGATACGGCGACCACCGAGATCTACACTATAGCCTACACTCTTTC

CCTACACGACGCTCTTCCGATCTgtggaaggacgaggtaccg-3'
```

```
                                    (SEQ ID NO: 345)
5'-AATGATACGGCGACCACCGAGATCTACACATAGAGGCACACTCTTTC

CCTACACGACGCTCTTCCGATCTgtggaaggacgaggtaccg-3'
```

```
                                    (SEQ ID NO: 346)
5'-AATGATACGGCGACCACCGAGATCTACACCCTATCCTACACTCTTTC

CCTACACGACGCTCTTCCGATCTgtggaaggacgaggtaccg-3'
```

```
                                    (SEQ ID NO: 347)
5'-AATGATACGGCGACCACCGAGATCTACACGGCTCTGAACACTCTTTC

CCTACACGACGCTCTTCCGATCTgtggaaggacgaggtaccg-3'
```

> Underlined: barcode
> Lowercase: constant vector region
> Not underlined/not lowercase: adapter TruSeq Adapters with i7 Barcodes:
Reverse:

```
                                    (SEQ ID NO: 348)
5'-CAAGCAGAAGACGGCATACGAGATCGAGTAATGTGACTGGAGTTCAG

ACGTGTGCTCTTCCGATCtattttaacttgctatttctagctctaaaac-

3'
```

```
                                    (SEQ ID NO: 349)
5'-CAAGCAGAAGACGGCATACGAGATTCTCCGGAGTGACTGGAGTTCAG

ACGTGTGCTCTTCCGATCtattttaacttgctatttctagctctaaaac-

3'
```

```
                                    (SEQ ID NO: 350)
5'-CAAGCAGAAGACGGCATACGAGATAATGAGCGGTGACTGGAGTTCAG

ACGTGTGCTCTTCCGATCtattttaacttgctatttctagctctaaaac-

3'
```

```
                                    (SEQ ID NO: 351)
5'-CAAGCAGAAGACGGCATACGAGATGGAATCTCGTGACTGGAGTTCAG

ACGTGTGCTCTTCCGATCtattttaacttgctatttctagctctaaaac-

3'
```

> Underlined: barcode
> Lowercase: constant vector region
> Not underlined/not lowercase: adapter Analysis of CRISPR Negative Selection Screen: Read counts for each gRNA were normalized for each replicate at each of the indicated time points (T27, T31, T35) and a log fold change relative to control (TO) was calculated. The BAGEL algorithm (Hart et al., 2015; Hart and Moffatt, 2015) was used to calculate a Bayes Factor (BF) for each gene, representing a confidence measure that the gene knockout results in a fitness defect. Bayes Factors at each time point were summed to a final BF for each gene.

Gene ontology enrichment analysis: Gene ontology enrichment was completed using GOrilla (Eden et al., 2009), using differential Z-score (FIG. 1A) for ranking. Results were filtered for a false discovery rate (FDR) <0.05, number of genes used in enrichment ≥5 and enrichment score >3.

Cloning of individual gRNA target sequences into pLCKO: pLCKO vector was digested with BfuAl (NEB) and gel purified with PureLink combo kit (ThermoFisher #K2200-01). Forward and reverse oligonucleotides coding for the gRNA targets (listed below) were phosphorylated and annealed. Oligonucleotides were first phosphorylated with PNK (ThermoFisher #AM2310) and annealed through 95 degrees centigrade incubation for 10 minutes followed by slope ramp-down to room temperature. Phosphorylated/annealed oligo pairs were ligated into BfuAl digested pLCKO in a 1:5 molar ratio with T4 ligase (NEB #M0202L) and transformed in DH5a cells. DNA was prepped with GeneElute HP plasmid midi-prep kit (Sigma #NA0200) and verified by Sanger sequencing. Note that gRNA targets were chosen from the 90k TKO library if they were shown to be functional in the screen (FZD5, WNT7B) or through CRISPR design tool (http://crispr.mit.edu/; Hsu et al., 2013; e.g., FZD7, FZD4, FZD8).

All gRNA target oligonucleotides were designed as follows:

```
                                    (SEQ ID NO: 4)
    5'-ACCGNNNNNNNNNNNNNNNNNNNNNNN-3'
```

```
                                    (SEQ ID NO: 5)
    3'-NNNNNNNNNNNNNNNNNNNNNNNCAAA-5'
```

Target Sequences:

```
    LacZ:
                                    (SEQ ID NO: 6)
    5'-CCCGAATCTCTATCGTGCGG-3'

CTNNB1:
                                    (SEQ ID NO: 7)
    5'-GAAAAGCGGCTGTTAGTCAC-3'

FZD4-1:
                                    (SEQ ID NO: 8)
    5'-AGCTCGTGCCCAACCAGGTT-3'

FZD4-2:
                                    (SEQ ID NO: 9)
    5'-ATGCCGCCGCATGGGCCAAT-3'

FZD5-1:
                                    (SEQ ID NO: 10)
    5'-AGGCCACCACAATGCTGGCG-3'

FZD5-2:
                                    (SEQ ID NO: 11)
    5'-TCCGCACCTTGTTGTAGAGC-3'

FZD7-1:
                                    (SEQ ID NO: 12)
    5'-GCCGGGGCGCAGCCGTACCA-3'

FZD7-2:
                                    (SEQ ID NO: 13)
    5'-TGGTACGGCTGCGCCCCGGC-3'
```

```
-continued
FZD8-1:
                                    (SEQ ID NO: 14)
5'-TAGCCGATGCCCTTACACAG-3'

FZD8-2:
                                    (SEQ ID NO: 15)
5'-CAACCACGACACGCAAGACG-3'

WNT7B:
                                    (SEQ ID NO: 16)
5'-GGCTGCGACCGCGAGAAGCA-3'
```

T7 endonuclease/assay to assess Cas9-gRNA cleavage: 5-7 days post pLCKO lentiviral transduction genomic DNA was extracted using PureLink genomic DNA mini kit (ThermoFisher #K2200-01). Genomic DNA was used as template to amplify targeted locus (primer pairs listed below) using Kapa HiFi polymerase (Kapa Biosystems #KK2602), following manufacturer's protocol. PCR products were purified with PureLink combo kit (ThermoFisher #K2200-01). DNA concentration in purified PCR products were quantified with NanoDrop 1000 (Thermo Scientific). 200 ng of CRISPR edited PCR product was mixed with 200 ng of wild-type PCR product with 1× NEB buffer 2.0 for a final volume of 19.5 microliters. Samples were heated to 95° for 10 minutes, followed by slow ramp-down to room temperature for heteroduplex formation. 0.5 microliters of T7 endonuclease I (NEB #M0302L) was added to each sample and incubated at 37 degrees centigrade for 20 minutes. Immediately following digest, samples were resolved on a 2% agarose gel (BioShop Canada #AGA001.500) containing ethidium bromide (BioShop Canada #ETB444.1).

```
FZD4 exon1 forward:
                                    (SEQ ID NO: 17)
5'-TGTCTCCTTCGGGCTAGGAT-3'

FZD4 exon1 reverse:
                                    (SEQ ID NO: 18)
5'-CGGGACGTCTAAAATCCCACA-3'

FZD4 exon2 forward:
                                    (SEQ ID NO: 19)
5'-CAGGTTCTGCTGCCTCTTCA-3'

FZD4 exon2 reverse:
                                    (SEQ ID NO: 20)
5'-AGTGTTGTGCAAAGAGGGCT-3'

FZD5 forward:
                                    (SEQ ID NO: 21)
5'-TTGCCCGACCAGATCCAGAC-3'

FZD5 reverse:
                                    (SEQ ID NO: 22)
5'-TCTGTCTGCCCGACTACCAC-3'

FZD7 forward:
                                    (SEQ ID NO: 23)
5'-TGAGGACTCTCATGCGTCGG-3'

FZD7 reverse:
                                    (SEQ ID NO: 24)
5'-AGCCGTCCGACGTGTTCT-3'

FZD8 forward:
                                    (SEQ ID NO: 25)
5'-TGTCTTGACGCGGTTGTAGAG-3'

FZD8 reverse:
                                    (SEQ ID NO: 26)
5'-TAGATTATCGGCAGACCCCC-3'
```

Crystal Violet Staining Proliferation Assay: HPAFII Cas9 cells were transduced with lentivirus generated with the indicated pLCKO plasmid as described above. 24 hours after infection cells were treated with puromycin. After 48 hours of selection, cells were PBS washed extensively, dissociated and counted. 2000 cells per well were re-seeded in 24-well format in media without puromycin. 24 hours post seeding, indicated wells were treated with DMSO control or 100 nM LGK974 (Cayman Chemical #14072) (note that these wells were from the LacZ gRNA population). Medium was renewed every 3-4 days and cells were fixed, 10 days post plating, using 100% ice-cold methanol. After fixation cells were stained with 0.5% crystal violet, 25% methanol solution for 20 minutes at room temperature, after which staining solution was removed and plates were washed several times in $dH_2O$.

Cell Viability Assays: For gRNA experiments, Cas9 expressing stable cell lines were transduced with indicated lentivirus as described above. 24 hours after infection cells were treated with puromycin. After 48-72 hours of puromycin selection, wells were washed with PBS extensively, dissociated and counted. Cells were re-seeded at 1000 cells per well, six wells per gRNA, in 96 well plates. Medium was changed every 3-4 days and viability was measured with Alamar Blue (ThermoFisher #DAL1025) 7-11 days post plating. Briefly, 10 microliters of Alamar Blue was added to 100 microliters medium per well and incubated 3-4 hours at 37 degrees centigrade, 5% $CO_2$. Fluorescence was measured at 560 nm excitation, 590 nm emission with Spectramax Gemini XS plate reader (Molecular Devices).

For antibody treatments, cells were seeded at 1000-2000 cells per well in 96-well plates. 24 hours after seeding, cells were treated with antibodies in quadruplicates, at the indicated concentrations. Medium was changed and antibodies renewed after 3 days. Viability was measured with Alamar Blue, 6 days after plating, using the same procedure described above.

Reverse transcription and quantitative real-time PCR: After indicated treatments, cells were lysed in Tri-reagent (BioShop Canada #TSS120) and RNA extracted using the manufacturer's protocol. RNA concentration was quantified with Nanodrop1000 (Thermo Scientific) and 2 micrograms of RNA per sample was DNase I treated (ThermoFisher #AM2222). DNase treated RNA was used to make cDNA with High-Capacity cDNA Reverse Transcription Kit (ThermoFisher #4368813). Real-time PCR was performed using Power SYBR Green Master Mix on the 7900HT Fast Real-Time PCR system. Primer pairs are listed below. Analysis was done using the comparative cycle threshold (CT) method (Bookout et al., 2006) with all samples normalized to PP/B (cyclophilin B) expression.

```
PPIB Forward:
                                    (SEQ ID NO: 27)
5'-GGAGATGGCACAGGAGGAA-3'

PPIB Reverse:
                                    (SEQ ID NO: 28)
5'-GCCCGTAGTGCTTCAGTTT-3'

AXIN2 Forward:
                                    (SEQ ID NO: 29)
5'-CTCCCCACCTTGAATGAAGA-3'

AXIN2 Reverse:
                                    (SEQ ID NO: 30)
5'-TGGCTGGTGCAAAGACATAG-3'
```

```
                    -continued
NKD1 Forward:
                                    (SEQ ID NO: 31)
    5'-TGAGAAGATGGAGAGAGTGAGCGA-3'

NKD1 Reverse:
                                    (SEQ ID NO: 32)
    5'-GGTGACCTTGCCGTTGTTGTCAAA-3'

MUC5AC Forward:
                                    (SEQ ID NO: 33)
    5'-AGCCGGGAACCTACTACTCG-3'

MUC5AC Reverse:
                                    (SEQ ID NO: 34)
    5'-AAGTGGTCATAGGCTTCGTGC-3'
```

RNAseq: RNAseq for the HPAF-II cell line was completed as described in detail previously for other cell lines (Hart et al., 2015). Briefly, total RNA was extracted using Tri-reagent (BioShop Canada #TSS120) following manufacturer's instructions. Sequencing libraries were prepared with Illumina TruSeq V2 RNA library preparation kit. Libraries were sequenced in single reads, 61 bp, on a High Output Illumina NextSeq500 flowcell (version1 chemistry). Reads were mapped using Gencode v19 gene models in TopHat v2.0.4. Gene expression values were determined using Cufflinks v2.2.1.

Figure 7A:

Isolation and characterization of anti-FZD5 Fabs: Phages displaying anti-FZD5 Fabs were isolated from a synthetic human Fab phage-display library (Library F) (FIG. 7C; Persson et al., 2013). Binding selections, phage ELISAs and Fab protein purification were performed as previously described (Colwill et al., 2011; Fellouse and Sidhu, 2007; Rajan and Sidhu, 2012). Briefly, the Fab phage-displayed library was precleared from non-specific binders with non-relevant protein (BSA), and phage particles displaying the Fabs from Library F were cycled through rounds of panning with recombinant human FZD5-Fc chimera (R&D Systems, Catalog no. 1617-FZ) immobilized on 96-well MaxiSorp Immunoplates (Fisher Scientific, Nepean, ON, Canada) as the capture target. The FZD5 portion of FZD5-Fc consists of the extracellular Ala27-Pro167 segment of FZD5 (see amino acid sequence below) which presents the Wnt-binding cysteine-rich domain (CRD) of FZD5 spanning amino acids Lys29-Thr156. The amino acid sequence of human Frizzled-5 (FZD5) can be accessed at National Center for Biotechnology Information, ACCESSION Q13467, VERSION Q13467.2. After four rounds of selection, phage were produced from individual clones grown in a 96-well format plates and phage ELISAs were performed to detect specific binding clones. Clones with positive binding were subjected to DNA sequencing. The DNAs encoding the variable heavy-chain and light-chain domains of the positive binders were cloned into vectors designed for production of Fabs, kappa light chain or IgG1 heavy chain, respectively, and Fabs were expressed from bacterial cells and IgGs from 293F cells (InvivoGen, San Diego, CA, USA). The Fabs and IgGs produced were affinity-purified on Protein A affinity columns (GE Healthcare, Mississauga, ON, Canada).

```
Amino acid sequence of Ala27-Pro167 segment of
FZD5:
                                    (SEQ ID NO: 368)
ASKAPVCQEITVPMCRGIGYNLTHMPNQFNHDTQDEAGLEVHQFWPLVEI

QCSPDLRFFLCSMYTPICLPDYHKPLPPCRSVCERAKAGCSPLMRQYGFA

WPERMSCDRLPVLGRDAEVLCMDYNRSEATTAPPRPFPAKP
```

Flow cytometry: Primary staining of cells was performed by treatment with 200 nM Frizzled profiler Fab. Alexa Fluor 488 AffiniPure F(ab')$_2$ was used as the secondary antibody (Jackson ImmunoResearch #109-546-097). c-Myc (9E10) IgG1 (primary antibody, Santa Cruz, lot #D0306) and Alexa Fluor 488 IgG (secondary antibody, Life technologies, lot #1458649) were used as controls. Dead cells were excluded by staining with Fixable Viability Dye eFluor 660 (eBioscience, catalogue number 65-0864). All reagents were used as per manufacturer's instructions. Flow cytometry was performed on a BD FACSCanto II flow cytometer (BD Biosciences), and data were analyzed with FlowJo software (FlowJo, LLC).

Mouse xenograft studies: CB-17 Fox Chase SCID mice (6 weeks old, female) were purchased from Charles River Laboratories (St. Constant, QC, Canada). The mice were housed in a pathogen-free environment at the animal facility at the University of Toronto. The study was conducted according to the guidelines of the Canadian Council on Animal Care (CCAC) and the animal use protocols approved by the University Animal Care Committee (UACC) at the University of Toronto. The recombinant antibody, IgG-2919, was developed and purified as described above. Human γ globulin was purchased from Jackson ImmunoResearch Laboratories, Inc. (West Grove, PA, USA), and Dulbecco's phosphate-buffered saline (DPBS, no calcium, no magnesium) was obtained from Thermo Fisher Scientific Inc. (Burlington, ON, Canada). Human γ globulin and D-PBS were used as the experimental controls in this study. HPAF-II cells were inoculated subcutaneously into the flank of the CB-17 SCID mice with $3 \times 10^6$ cells in D-PBS per mouse. Tumor volumes were measured using vernier calipers and the mice were weighed twice weekly. Tumor volume was calculated using the formula: $\frac{1}{2}(\text{Length} \times \text{Width}^2)$. When tumors reached approximately 200 mm$^3$, the mice were randomized into four groups of nine or ten mice each. Each group received one of the following treatments: Human γ globulin (10 mg/kg), D-PBS (15 mL/kg), IgG-2919 (2 mg/kg), or IgG-2919 (1 mg/kg), twice weekly via intraperitoneal injection for four and a half weeks. For calculation of percentage of tumor growth inhibition (TGI), groups treated with antibody (Ab test) were compared with group treated with human γ globulin (control). TGI (%) was calculated using the formula: TGI $(\%) = \{(\text{mean TVG}_{control} - \text{mean TVG}_{Ab\ test})/\text{mean TVG}_{control}\} \times 100$, where the mean TVG (tumor volume growth) = mean tumor volume at a defined study day − mean tumor volume the day of the first dosing. Statistical significance was examined by Student's t-test (two-tailed). P-values less than 0.05 were considered statistically significant.

Histological staining: Tumor staining was carried out at the immuno-histopathology and tissue processing lab at the University Health Network. Briefly, three representative tumors from each treatment group (human gamma-globulin at 10 mg/kg, IgG-2919 at 1 mg/kg and IgG-2919 at 2 mg/kg) were embedded into a wax block and paraffin embedded tumors were cut into thin sections and mounted onto a microscope slide for routine staining with hematoxylin and eosin, periodic acid-Schiff or PAS (Abcam—ab150680), Alcian Blue pH 1.0 (Abcam—ab150661), and Alcian Blue pH 2.5 (Abcam—ab150662). An Axio Scan slide scanner system was used to generate high resolution digital images of the whole tumor sections at 40× in brightfield mode, and the images were exported as .png files using ZEN software.

Results

Figure 1A:
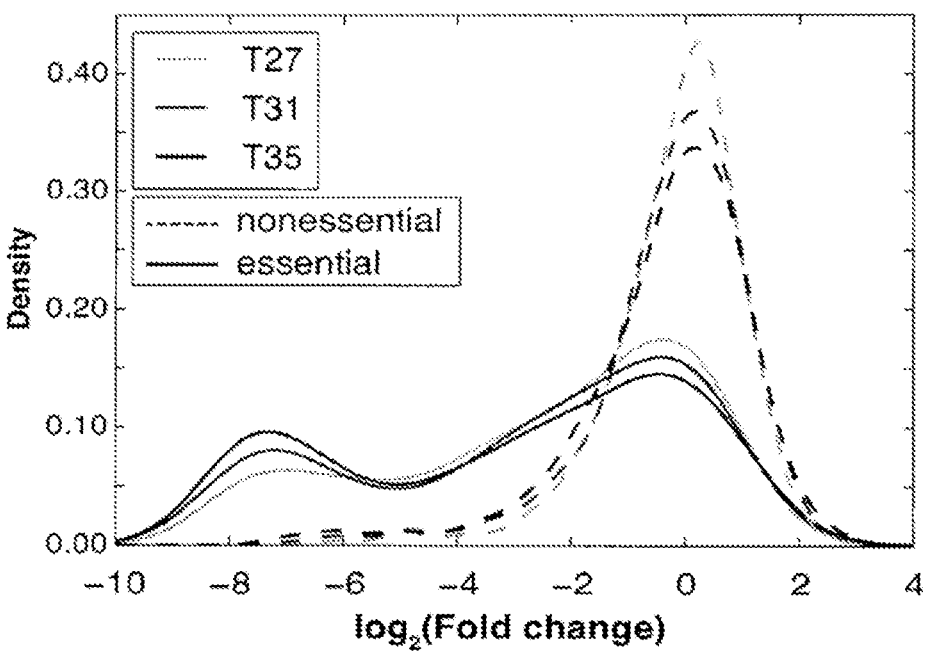
Figure 2:
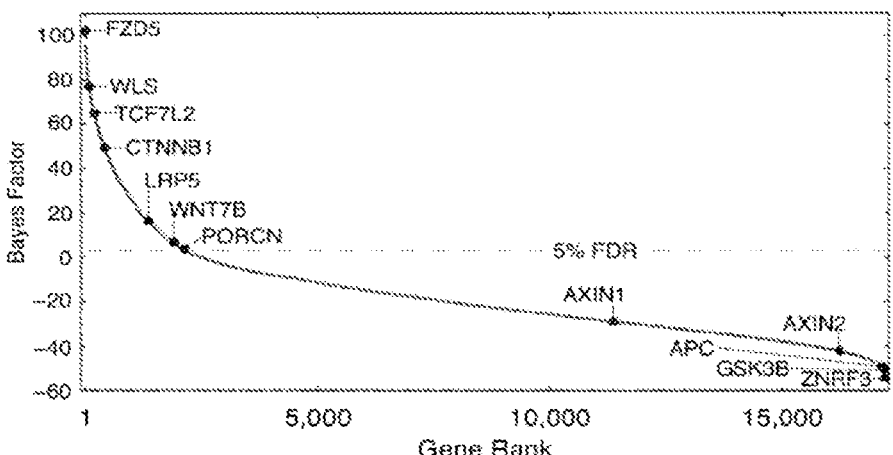

Example 2: Fitness Analysis Identifies the Wnt Receptor FZD5 as Essential for Proliferation of RNF43-Mutant Pancreatic Cancer Cell Lines To identify context-dependent fitness genes in RNF43-mutant pancreatic cancer cells, the HPAF-II PDAC cell line that was previously shown to be exquisitely sensitive to PORCN inhibition (Jiang et al., 2013) was used. A genetic screen was carried out using the TKO gRNA library and evolving cell populations were monitored over ~20 doublings by deep sequencing of gRNAs (Hart et al., 2015). Abundance of gRNAs over multiple time points was assessed using gold-standard sets of essential and nonessential genes (Hart et al., 2014). The fold-change distribution of gRNAs targeting essential genes was significantly shifted relative to those targeting nonessential genes, and this shift increased with time indicating that the screen functioned as designed (FIG. 1A). The BAGEL algorithm was then used to calculate a log Bayes Factor (BF) for each gene, which is a measure of the confidence that knockout of a specific gene causes a decrease in fitness (high BF indicates increased confidence that the knockout of the gene results in a decrease in fitness) (FIG. 2). Comparing the HPAF-II screen to TKO fitness screens carried out in five diverse human cell lines (Hart et al., 2015) indicated the fitness gene profile of HPAF-II cells was most similar to DLD-1 and HCT116 colorectal cancer cells, which may reflect the common endodermal origin of these cell lines. A total of 2,174 fitness genes were identified in HPAF-II cells (false discovery rate<5%), including 1,315 of 1,580 (83%) previously identified fitness genes (Hart et al., 2015).

Figure 1B:
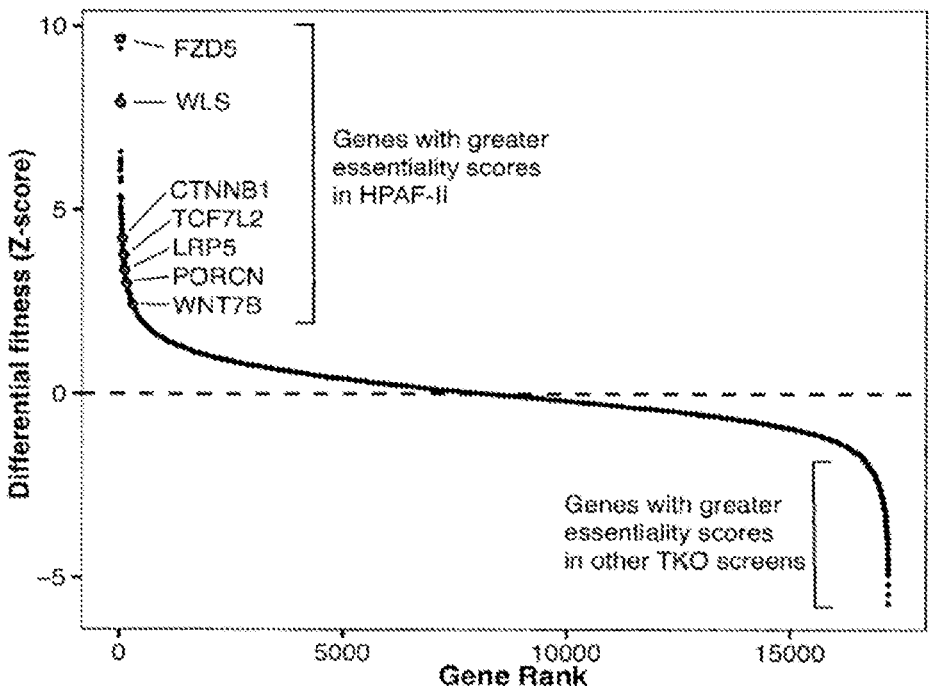
Figure 1C:
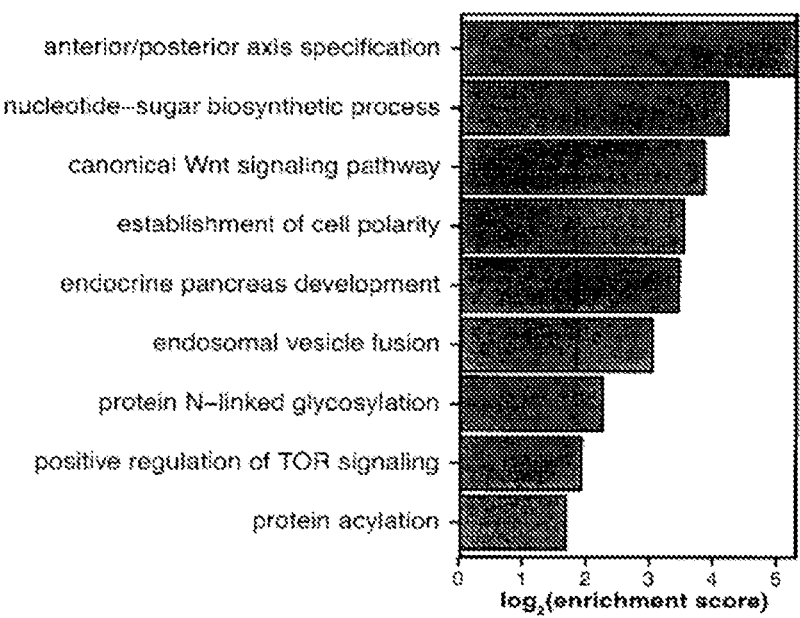
Figure 3:
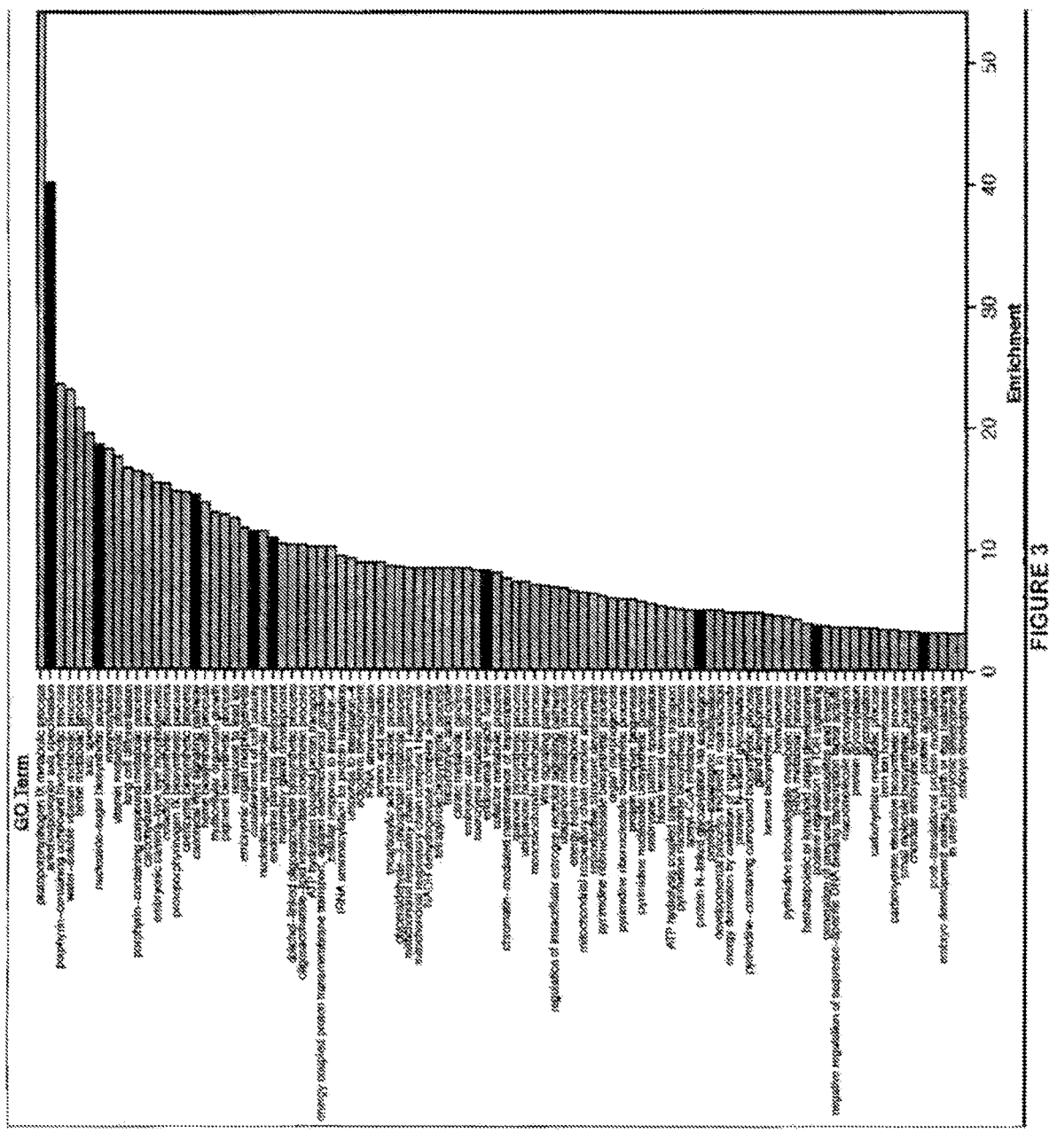

The context-dependent fitness genes that were specific to HPAF-II cells were then compared to other cell lines screened with the TKO library. For each gene, the difference between Bayes Factor (BF) scores in HPAF-II cells and the average BF scores across the 5 previously reported screens was calculated, and that difference was converted to a Z-score. Examination of the top differential fitness genes readily highlighted the known addiction of HPAF-II cells to Wnt-beta-catenin signaling, since several genes previously described as positive regulators of this pathway having Z-scores of >2 (FZD5, WLS, CTNNB1 (beta-catenin), TCF7L2, LRP5, PORCN, WNT7B) were observed (FIG. 1B). The ranked list of differential essentiality scores for gene ontology (GO) term enrichment were then analyzed and multiple biological process terms for HPAF-II context-specific essential genes were found that were related to Wnt biology including "anterior-posterior axis specification", "canonical Wnt signaling pathway", and "establishment of cell polarity" (FIG. 1C and FIG. 3). Moreover, HPAF-II context essentials are enriched for the biological processes involved in the biogenesis and activity of Wnt signaling components. These processes include protein N-linked glycosylation, nucleotide-sugar biosynthesis (which produces substrates for glycosyltransferases), protein acylation, and endosomal vesicle fusion.

Core negative regulators of the Wnt-beta-catenin pathway were found amongst the lowest BFs including APC, GSK3B, and ZNRF3, suggesting that knockout of these genes may provide a proliferation advantage to HPAF-II cells (FIG. 2). Topping the list in the context-dependent fitness analysis was the Wnt receptor FZD5 (Z-score >10), which was the only one of ten Frizzled homologs essential for growth of these cells.

Figure 4A:
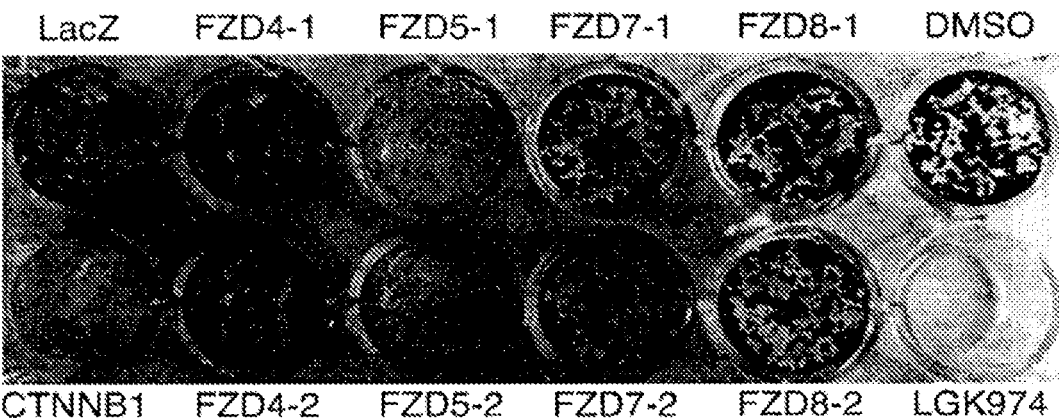
Figure 4B:
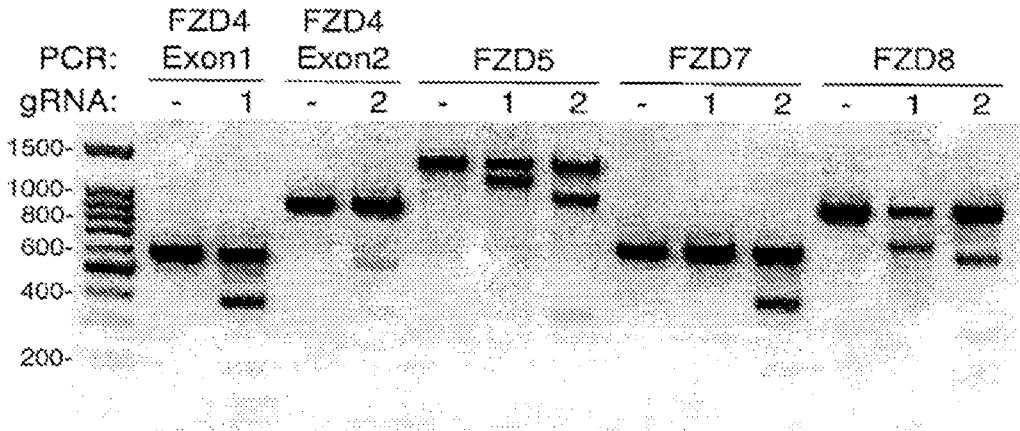
Figure 4C:
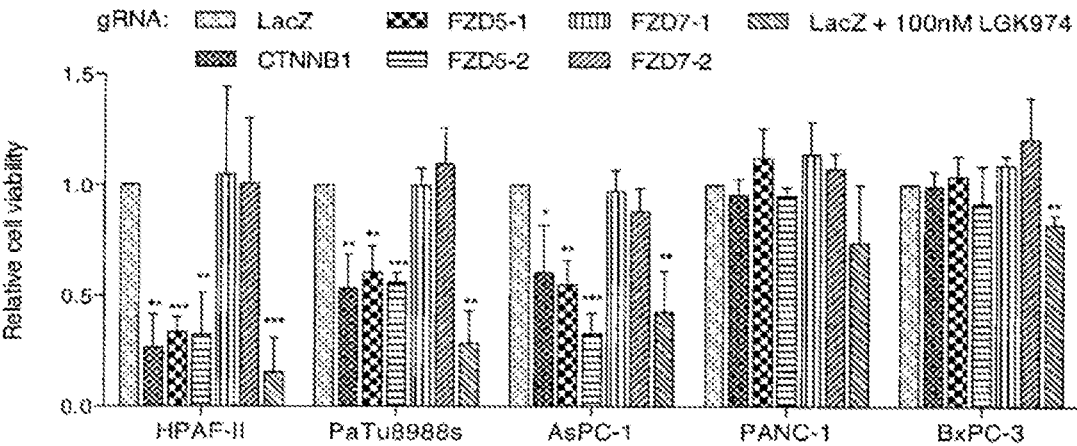
Figure 4D:
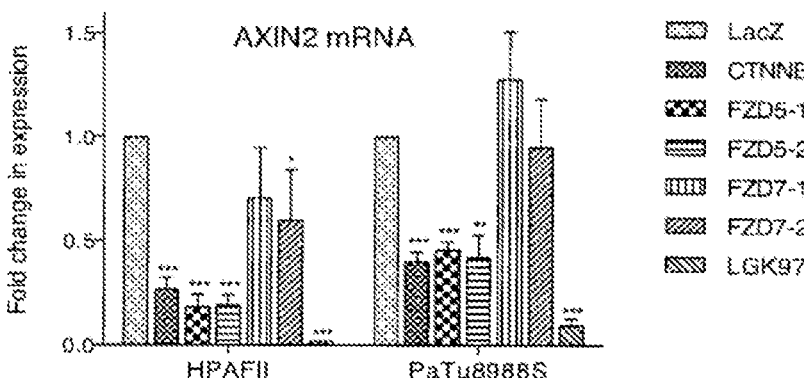
Figure 4E:
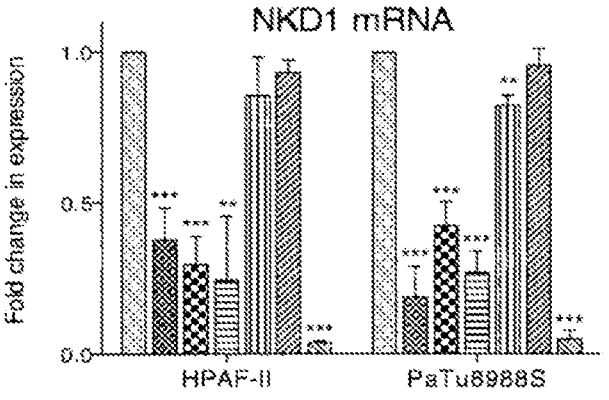
Figure 4E:
Figure 4F:
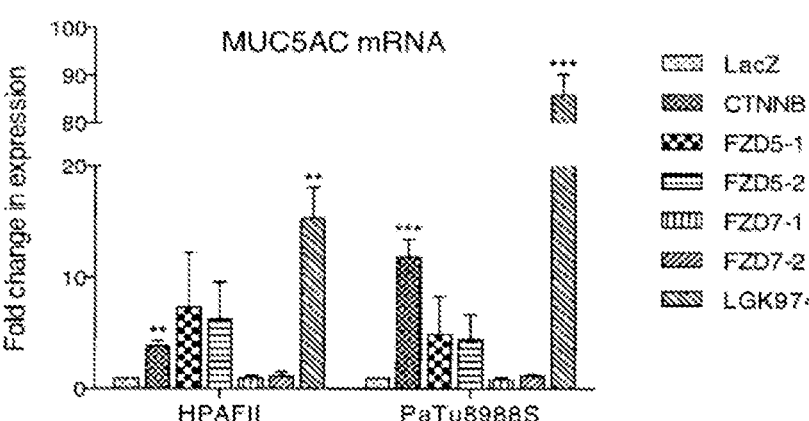
Figure 4G:
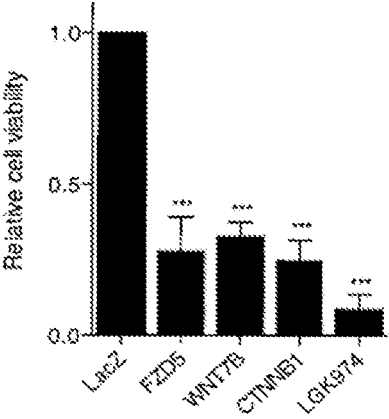
Figure 5:
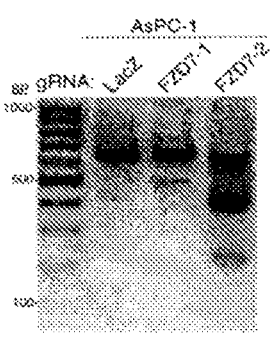
Figure 5:
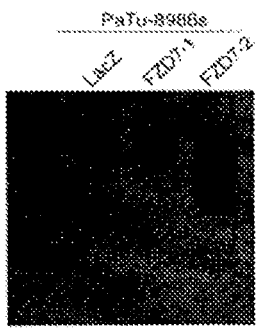
Figure 5:
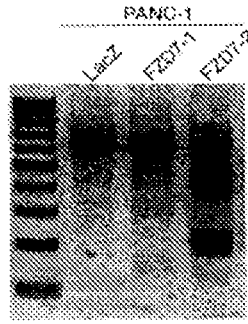
Figure 5:
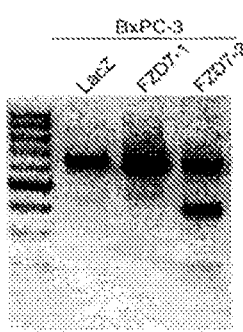

Example 3: Gene-Knockout of FZD5 or WNT7B Inhibits Growth of RNF43-Mutant Pancreatic Cancer Cell Lines, with Gene-Knockout of FZD5 Further Inducing Phenotypic Differentiation of RNF43-Mutant Pancreatic Cancer Cell Lines To validate the screen results HPAF-II cells were first infected with lentivirus coding for various gRNAs, transduced cells were selected for 48 hours and plated in clonogenic growth assays. Knockout of FZD5 using two independent gRNAs led to robust growth inhibition, comparable to treatment with a CTNNB1 gRNA or the PORCN inhibitor LGK974 (FIG. 4A). In contrast, cells transduced with a control LACZ gRNA or two validated and unique gRNAs for each of FZD4, FZD7 or FZD8 exhibited normal growth (FIG. 4A, FIG. 4B and Table 1). Whether FZD5 was also required specifically for the growth of other RNF43-mutant PDAC cell lines was next tested and it was found that FZD5 gRNAs, but not FZD7 gRNAs, inhibited the growth of PaTu-8988S and AsPC-1 cells to levels similar to cells treated with LGK974 or transduced with the CTNNB1 gRNA (FIG. 4C and FIG. 5). In contrast, the growth of PANC-1 and BxPC-3 cell lines, which are wild-type for RNF43, was not inhibited by gRNAs targeting FZD5, FZD7 or CTNNB1 (FIG. 4C and FIG. 5). Consistent with these results and supporting a key role for FZD5 in transducing autocrine Wnt-beta-catenin signaling in RNF43-mutant cells, knockout of FZD5 led to marked inhibition of the Wnt target genes AXIN2 and NKD1 whereas minimal or no change was observed in cells transduced with FZD7 gRNAs (FIG. 4D and FIG. 4E). Furthermore, knocking out FZD5 or CTNNB1, or treatment of cells with LGK974, led to increased expression of the differentiation marker MUC5AC (Jiang et al., 2013), whereas no change was observed in RNF43-mutant PDAC cells knocked out for FZD7 (FIG. 4F). Notably, WNT7B was the only Wnt gene out of 19 with a differential fitness Z-score >2 in the genome-wide CRISPR screen (FIG. 1B). Taken together, these results indicate that autocrine WNT7B-FZD5 signaling is responsible for the bulk of beta-catenin signaling in RNF43-mutant PDAC cells. Consistent with this prediction, transduction of a WNT7B gRNA strongly inhibited proliferation of HPAF-II cells (FIG. 4G). These results indicate that a WNT7B-FZD5 signaling circuit is specifically required for Wnt-beta-catenin signaling and that blocking FZD5 or WNT7B is sufficient to inhibit proliferation of RNF43-mutant PDAC cells.

TABLE 1

| | T7E1 expected cleavage products | | |
| Primer pair | Amplicon length (bp) | gRNA-1 Expected cleavage product lengths (bp) | gRNA-2 Expected cleavage product lengths (bp) |
| --- | --- | --- | --- |
| FZD4 exon1 | 577 | 196, 381 | NA |
| FZD4 exon2 | 880 | NA | 351, 529 |
| FZD5 | 1297 | 192, 1105 | 341, 956 |
| FZD7 | 614 | 143, 471 | 213, 401 |
| FZD8 | 913 | 277, 636 | 338, 575 |

Given the large combinatorial possibilities of the Wnt pathway (i.e., 19 Wnt ligand family members and 10 Frizzled receptor family members), it was unexpected that a single specific Wnt-Frizzled ligand-receptor pair is responsible for driving cellular proliferation in RNF43-mutant pancreatic cancer (HPAF-II) cells. RNA-seq analysis revealed that several of the Wnt family genes (WNT2B, WNT3, WNT7A, WNT7B, WNT9A, WNT10A, WNT10B, WNT16) and several of the Frizzled family genes (FZD1, FZD2, FZD3, FZD4, FZD5, FZD6, FZD7) are expressed in HPAF-II cells, suggesting that the FZD5-WNT7B circuit is not driven simply by expression (Table 2).

TABLE 2

RNA-seq analysis of all Frizzled, Wnt and LRP5/6 genes in HPAF-II cells.

| Gene | Bayes Factor | mRNA expression [log$_2$(fpkm + 0.01)] |
|---|---|---|
| FZD1 | −27.68 | 1.794 |
| FZD2 | 0.737 | −0.141 |
| FZD3 | −15.349 | 2.015 |
| FZD4 | −13.417 | −0.073 |
| FZD5 | 102.33 | 3.762 |
| FZD6 | −28.921 | 2.979 |
| FZD7 | −28.487 | 2.235 |
| FZD8 | −30.927 | −2.681 |
| FZD9 | −17.449 | −6.644 |
| FZD10 | −35.687 | −6.644 |
| WNT1 | −21.84 | −6.644 |
| WNT2 | −46.514 | −3.889 |
| WNT2B | −38.503 | −0.753 |
| WNT3 | −19.681 | −0.145 |
| WNT3A | −33.865 | −6.567 |
| WNT4 | −40.586 | −2.331 |
| WNT5A | −45.141 | −3.85 |
| WNT5B | −34.797 | −5.463 |
| WNT6 | −26.526 | −2.068 |
| WNT7A | −34.094 | −0.153 |
| WNT7B | 6.745 | 4.913 |
| WNT8A | −26.12 | −6.388 |
| WNT8B | −44.29 | −1.267 |
| WNT9A | −42.009 | 3.076 |
| WNT9B | −20.708 | −6.487 |
| WNT10A | 4.626 | 4.683 |
| WNT10B | −32.366 | 2.352 |
| WNT11 | −22.607 | −6.021 |
| WNT16 | −45.369 | 0.084 |
| LRP5 | 16.618 | 5.422 |
| LRP6 | −10.69 | 2.765 |

Example 4: Generation of Anti-FZD5 Fab Panel

Recombinant FZD5-Fc was used as binding target for selection of phage-Fabs that bind to the Wnt-binding cysteine-rich domain (CRD) of FZD5, as described above. Thirty-nine anti-FZD5 phage-Fab clones (clone IDS #2898 to #2936 having antibody variable region IDs Fv-2898 to Fv-2936, respectively) with unique antibody variable regions were identified. In all 39 Fv-2898 to Fv-2936 antibody variable regions identified (and hence in any Frizzled protein-binding agent, such as a Fab or IgG, having one of these antibody variable regions), the following FRs or FR segments have identical amino acid sequences: VL domain FR1, VL domain FR2, VL domain FR3, VL domain FR4, VH domain FR1, VH domain FR2 segment spanning positions 40-54, VH domain FR3 segment spanning positions 67-104, and VH domain FR4.

Figure 6:
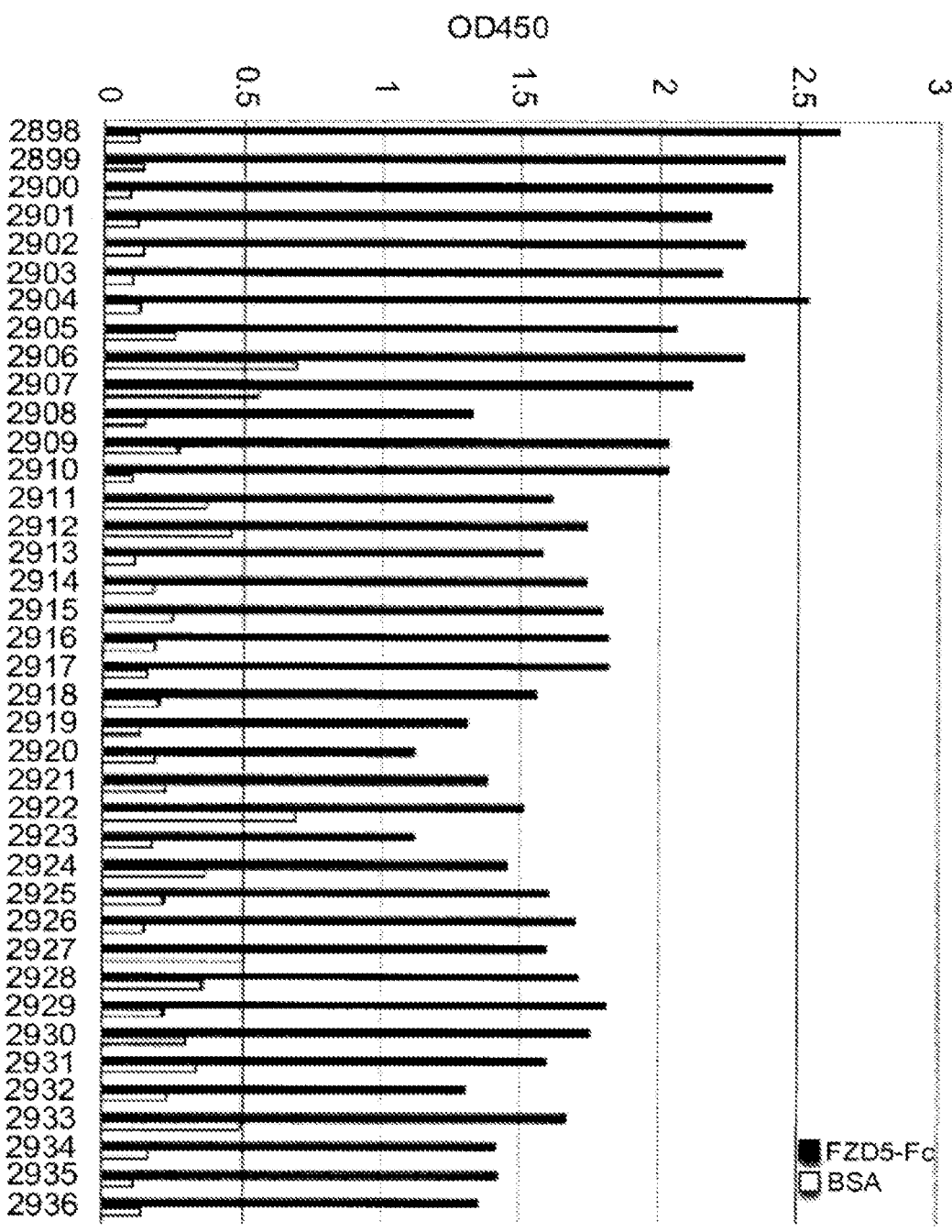

Purified anti-FZD5 Fabs (Fab IDs Fab-2898 to Fab-2936, having as antibody variable regions Fv-2898 to Fv-2936, respectively) were tested in an ELISA assay to confirm their binding to recombinant FZD5-Fc antigen. All Fabs were found to specifically bind to FZD5-Fc (FIG. 6).

Refer to the tables below for the amino acid sequences (and nucleic acid sequences encoding same) of the components of anti-FZD5 antibody variable regions Fv-2898 to Fv-2936, and of the exemplary complete heavy chain and light chain of antibody IgG-2919 having antibody variable region Fv-2919:

Table 3A: CDR-L1 amino acid sequence
Table 3B: CDR-L2 amino acid sequence
Table CDR-L3 amino acid sequence 3C:
Table 4A: CDR-H1 amino acid sequence and amino acid residue at position 39
Table 4B: CDR-H2 amino acid sequence and amino acid residues at positions 55 and 66
Table CDR-H3 amino acid sequence 4C:
Table 5A: nucleic acid sequence encoding CDR-L1
Table 5B: nucleic acid sequence encoding CDR-L2
Table nucleic acid sequence encoding CDR-L3 5C:
Table 6A: nucleic acid sequences encoding CDR-H1 and amino acid residue at position 39
Table 6B: nucleic acid sequences encoding CDR-H2 and amino acid residues at positions 55 and 66
Table nucleic acid sequence encoding CDR-H3 6C:
Table 7: amino acid sequences (and nucleic acid sequences encoding same) of VL domain FR1, VL domain FR2, VL domain FR3, VL domain FR4, VH domain FR1, VH domain FR2 segment spanning positions 40-54, VH domain FR3 segment spanning positions 67-104, and VH domain FR4
Table 8: exemplary full length amino acid sequences (and nucleic acid sequences encoding same) of anti-FZD5 antibody IgG-2919 having antibody variable region Fv-2919

TABLE 3A

Amino acid sequence of CDR-L1 of anti-FZD5 variable regions identified.

| Antibody variable region IDs | CDR-L1 amino acid sequence | SEQ ID NO. |
|---|---|---|
| Fv-2898 to Fv-2936 | QSVSSA | SEQ ID NO: 35 |

TABLE 3B

Amino acid sequence of CDR-L2 of anti-FZD5 variable regions identified.

| Antibody variable region IDs | CDR-L2 amino acid sequence | SEQ ID NO. |
|---|---|---|
| Fv-2898 to Fv-2936 | SAS | SEQ ID NO: 36 |

TABLE 3C

Amino acid sequences of CDR-L3 of anti-FZD5 antibody variable regions identified.

| Variable region ID | CDR-L3 amino acid sequence | SEQ ID NO. |
|---|---|---|
| Fv-2898 | QQWWGYYSLIT | SEQ ID NO: 37 |
| Fv-2899 | QQWYSSYGLIT | SEQ ID NO: 38 |
| Fv-2900 | QQWYSGSSLFT | SEQ ID NO: 39 |
| Fv-2901 | QQGGFLIT | SEQ ID NO: 40 |
| Fv-2902 | QQWYAFGALIT | SEQ ID NO: 41 |
| Fv-2903 | QQWGGGSSLFT | SEQ ID NO: 42 |
| Fv-2904 | QQSSYSLIT | SEQ ID NO: 43 |
| Fv-2905 | QQSSWYYGYPFT | SEQ ID NO: 44 |

TABLE 3C-continued

Amino acid sequences of CDR-L3 of anti-FZD5
antibody variable regions identified.

| Variable region ID | CDR-L3 amino acid sequence | SEQ ID NO. |
|---|---|---|
| Fv-2906 | QQWSWGFLIT | SEQ ID NO: 45 |
| Fv-2907 | QQVGYWWGLIT | SEQ ID NO: 46 |
| Fv-2908 | QQSSYSLIT | SEQ ID NO: 47 |
| Fv-2909 | QQSWSYHYLIT | SEQ ID NO: 48 |
| Fv-2910 | QQWYGSHLIT | SEQ ID NO: 49 |
| Fv-2911 | QQGPWYPFT | SEQ ID NO: 50 |
| Fv-2912 | QQFYFPPYLIT | SEQ ID NO: 51 |
| Fv-2913 | QQWGVSHYLFT | SEQ ID NO: 52 |
| Fv-2914 | QQWYYGSLIT | SEQ ID NO: 53 |
| Fv-2915 | QQAYYHSLIT | SEQ ID NO: 54 |
| Fv-2916 | QQWYHYPYLIT | SEQ ID NO: 55 |
| Fv-2917 | QQSSYSLIT | SEQ ID NO: 56 |
| Fv-2918 | QQAFGASLFT | SEQ ID NO: 57 |
| Fv-2919 | QQWYSSGHVLIT | SEQ ID NO: 58 |
| Fv-2920 | QQWFAGALIT | SEQ ID NO: 59 |
| Fv-2921 | QQWYAGSLIT | SEQ ID NO: 60 |
| Fv-2922 | QQSFVYPYLIT | SEQ ID NO: 61 |
| Fv-2923 | QQWYGYSALIT | SEQ ID NO: 62 |
| Fv-2924 | QQWYSGHSLIT | SEQ ID NO: 63 |
| Fv-2925 | QQAWVYASLFT | SEQ ID NO: 64 |
| Fv-2926 | QQWYHGGSLFT | SEQ ID NO: 65 |
| Fv-2927 | QQWGSHGYLIT | SEQ ID NO: 66 |
| Fv-2928 | QQAFYYPIT | SEQ ID NO: 67 |
| Fv-2929 | QQWYSSYGLIT | SEQ ID NO: 68 |
| Fv-2930 | QQWYGPYLIT | SEQ ID NO: 69 |
| Fv-2931 | QQSSYSLIT | SEQ ID NO: 70 |
| Fv-2932 | QQWYGSFALIT | SEQ ID NO: 71 |
| Fv-2933 | QQFWWYASWLFT | SEQ ID NO: 72 |
| Fv-2934 | QQWYHYGLIT | SEQ ID NO: 73 |
| Fv-2935 | QQWYGGYALIT | SEQ ID NO: 74 |
| Fv-2936 | QQWYAASLIT | SEQ ID NO: 75 |

TABLE 4A

Amino acid sequences of CDR-H1 and of the
amino acid residue at position 39 of anti-FZD5
antibody variable regions identified.

| Antibody variable region ID | CDR-H1 amino acid sequence | SEQ ID NO. of CDR-H1 | Amino acid residue at position 39 |
|---|---|---|---|
| Fv-2898 | GFNIYSYS | SEQ ID NO: 76 | Met (M) |
| Fv-2899 | GFNLYYYY | SEQ ID NO: 77 | Met (M) |
| Fv-2900 | GFNLSSYY | SEQ ID NO: 78 | Ile (I) |
| Fv-2901 | GFNISYSY | SEQ ID NO: 79 | Met (M) |
| Fv-2902 | GFNISYYY | SEQ ID NO: 80 | Ile (I) |
| Fv-2903 | GFNLSYYY | SEQ ID NO: 81 | Ile (I) |
| Fv-2904 | GFNIYSYS | SEQ ID NO: 82 | Met (M) |
| Fv-2905 | GFNLSYYY | SEQ ID NO: 83 | Met (M) |
| Fv-2906 | GFNFSSSS | SEQ ID NO: 84 | Ile (I) |
| Fv-2907 | GFNIYSSY | SEQ ID NO: 85 | Met (M) |
| Fv-2908 | GFNFSSSS | SEQ ID NO: 86 | Ile (I) |
| Fv-2909 | GFNISSSY | SEQ ID NO: 87 | Met (M) |
| Fv-2910 | GFNISYSY | SEQ ID NO: 88 | Met (M) |
| Fv-2911 | GFNIYSS | SEQ ID NO: 89 | Met (M) |
| Fv-2912 | GFNISYSY | SEQ ID NO: 90 | Ile (I) |
| Fv-2913 | GFNISYSS | SEQ ID NO: 91 | Ile (I) |
| Fv-2914 | GFNIYYSY | SEQ ID NO: 92 | Met (M) |
| Fv-2915 | GFNIYYYS | SEQ ID NO: 93 | Met (M) |
| Fv-2916 | GFNISYSS | SEQ ID NO: 94 | Ile (I) |
| Fv-2917 | GFNFSSSS | SEQ ID NO: 95 | Ile (I) |
| Fv-2918 | GFNLSYSS | SEQ ID NO: 96 | Ile (I) |
| Fv-2919 | GFNISYSY | SEQ ID NO: 97 | Ile (I) |
| Fv-2920 | GFNISYYY | SEQ ID NO: 98 | Ile (I) |
| Fv-2921 | GFNISYYY | SEQ ID NO: 98 | Ile (I) |
| Fv-2922 | GFNIYSSY | SEQ ID NO: 99 | Met (M) |
| Fv-2923 | GFNLYYYY | SEQ ID NO: 100 | Met (M) |
| Fv-2924 | GFNISYSY | SEQ ID NO: 101 | Ile (I) |
| Fv-2925 | GFNLSYSS | SEQ ID NO: 102 | Met (M) |
| Fv-2926 | GFNIYSSY | SEQ ID NO: 103 | Met (M) |
| Fv-2927 | GFNIYYSS | SEQ ID NO: 104 | Met (M) |
| Fv-2928 | GFNISYSS | SEQ ID NO: 105 | Ile (I) |
| Fv-2929 | GFNISYYY | SEQ ID NO: 106 | Ile (I) |
| Fv-2930 | GFNLSYYY | SEQ ID NO: 107 | Ile (I) |
| Fv-2931 | GFNLSYSS | SEQ ID NO: 102 | Met (M) |
| Fv-2932 | GFNISYSY | SEQ ID NO: 108 | Met (M) |
| Fv-2933 | GFNLYSSY | SEQ ID NO: 109 | Met (M) |

TABLE 4A-continued

Amino acid sequences of CDR-H1 and of the amino acid residue at position 39 of anti-FZD5 antibody variable regions identified.

| Antibody variable region ID | CDR-H1 amino acid sequence | SEQ ID NO. of CDR-H1 | Amino acid residue at position 39 |
|---|---|---|---|
| Fv-2934 | GFNISYSY | SEQ ID NO: 110 | Met (M) |
| Fv-2935 | GFNIYYYY | SEQ ID NO: 111 | Ile (I) |
| Fv-2936 | GFNISYYY | SEQ ID NO: 112 | Met (M) |

TABLE 4B

Amino acid sequences of CDR-H2 and of the amino acid residues at positions 55 and 66 of anti-FZD5 antibody variable regions identified.

| Antibody variable region ID | CDR-H2 amino acid sequence | SEQ ID NO. of CDR H2 amino acid sequence | Amino acid residue at position 55 | Amino acid residue at position 66 |
|---|---|---|---|---|
| Fv-2898 | IYSSSGST | SEQ ID NO: 113 | Ser (S) | Ser (S) |
| Fv-2899 | IYPSSGST | SEQ ID NO: 114 | Ser (S) | Ser (S) |
| Fv-2900 | ISSSSSST | SEQ ID NO: 115 | Ser (S) | Ser (S) |
| Fv-2901 | IYSYSSYT | SEQ ID NO: 116 | Ser (S) | Tyr (Y) |
| Fv-2902 | ISSSSSST | SEQ ID NO: 117 | Ser (S) | Ser (S) |
| Fv-2903 | IYPYSSYT | SEQ ID NO: 118 | Ser (S) | Ser (S) |
| Fv-2904 | ISSSYGYT | SEQ ID NO: 119 | Tyr (Y) | Ser (S) |
| Fv-2905 | IYSSYSYT | SEQ ID NO: 120 | Ser (S) | Ser (S) |
| Fv-2906 | ISSSYGYT | SEQ ID NO: 121 | Tyr (Y) | Tyr (Y) |
| Fv-2907 | ISSYSGST | SEQ ID NO: 122 | Ser (S) | Tyr (Y) |
| Fv-2908 | IYPSYSYT | SEQ ID NO: 123 | Tyr (Y) | Tyr (Y) |
| Fv-2909 | ISSSSGYT | SEQ ID NO: 124 | Ser (S) | Ser (S) |
| Fv-2910 | IYSSSSST | SEQ ID NO: 125 | Ser (S) | Ser (S) |
| Fv-2911 | IYPYSGYT | SEQ ID NO: 126 | Tyr (Y) | Ser (S) |
| Fv-2912 | ISSSSGYT | SEQ ID NO: 127 | Ser (S) | Ser (S) |
| Fv-2913 | IYPYSSST | SEQ ID NO: 128 | Ser (S) | Ser (S) |
| Fv-2914 | IYPSSSST | SEQ ID NO: 129 | Ser (S) | Ser (S) |
| Fv-2915 | IYSSYGYT | SEQ ID NO: 130 | Ser (S) | Ser (S) |
| Fv-2916 | IYPSYSYT | SEQ ID NO: 131 | Ser (S) | Tyr (Y) |
| Fv-2917 | ISSSYGYT | SEQ ID NO: 132 | Ser (S) | Tyr (Y) |
| Fv-2918 | IYSSYSST | SEQ ID NO: 133 | Ser (S) | Ser (S) |
| Fv-2919 | IYSSSGST | SEQ ID NO: 134 | Ser (S) | Ser (S) |
| Fv-2920 | IYPSSGST | SEQ ID NO: 135 | Ser (S) | Ser (S) |
| Fv-2921 | IYPSSGST | SEQ ID NO: 136 | Ser (S) | Ser (S) |
| Fv-2922 | ISPYSGYT | SEQ ID NO: 137 | Ser (S) | Ser (S) |

TABLE 4B-continued

Amino acid sequences of CDR-H2 and of the amino acid residues at positions 55 and 66 of anti-FZD5 antibody variable regions identified.

| Antibody variable region ID | CDR-H2 amino acid sequence | SEQ ID NO. of CDR H2 amino acid sequence | Amino acid residue at position 55 | Amino acid residue at position 66 |
|---|---|---|---|---|
| Fv-2923 | IYSSSGST | SEQ ID NO: 138 | Ser (S) | Ser (S) |
| Fv-2924 | IYSYYSST | SEQ ID NO: 139 | Ser (S) | Ser (S) |
| Fv-2925 | IYPSYGST | SEQ ID NO: 140 | Ser (S) | Tyr (Y) |
| Fv-2926 | IYPSSSST | SEQ ID NO: 141 | Ser (S) | Ser (S) |
| Fv-2927 | IYPSYGYT | SEQ ID NO: 142 | Ser (S) | Ser (S) |
| Fv-2928 | IYPSYSST | SEQ ID NO: 143 | Ser (S) | Tyr (Y) |
| Fv-2929 | IYPSSSST | SEQ ID NO: 144 | Ser (S) | Ser (S) |
| Fv-2930 | IYPYSGST | SEQ ID NO: 145 | Ser (S) | Ser (S) |
| Fv-2931 | ISPYSGST | SEQ ID NO: 146 | Tyr (Y) | Tyr (Y) |
| Fv-2932 | IYSSYSST | SEQ ID NO: 147 | Ser (S) | Ser (S) |
| Fv-2933 | IYSSYGYT | SEQ ID NO: 148 | Ser (S) | Ser (S) |
| Fv-2934 | IYSSSGST | SEQ ID NO: 149 | Ser (S) | Ser (S) |
| Fv-2935 | IYPSSGST | SEQ ID NO: 150 | Ser (S) | Ser (S) |
| Fv-2936 | IYSSSGST | SEQ ID NO: 151 | Ser (S) | Ser (S) |

TABLE 4C

Amino acid sequences of CDR-H3 of anti-FZD5 antibody variable regions identified.

| Antibody variable region ID | CDR-H3 amino acid sequence | SEQ ID NO. |
|---|---|---|
| Fv-2898 | ARAVWGL DY | SEQ ID NO: 152 |
| Fv-2899 | ARGALDY | SEQ ID NO: 153 |
| Fv-2900 | ARGALDY | SEQ ID NO: 153 |
| Fv-2901 | ARSWYYWSPSSGMDY | SEQ ID NO: 154 |
| Fv-2902 | ARGALDY | SEQ ID NO: 153 |
| Fv-2903 | ARGAIDY | SEQ ID NO: 155 |
| Fv-2904 | ARSWYAWAMDY | SEQ ID NO: 156 |
| Fv-2905 | ARSGYALDY | SEQ ID NO: 157 |
| Fv-2906 | ARTVRGSKKPYFSGWAMDY | SEQ ID NO: 158 |
| Fv-2907 | ARSSWGAYIVSYGFDY | SEQ ID NO: 159 |
| Fv-2908 | ARAYYGHFHAMDY | SEQ ID NO: 160 |
| Fv-2909 | ARTVRGSKKPYFSGWAMDY | SEQ ID NO: 161 |
| Fv-2910 | ARGAMDY | SEQ ID NO: 162 |
| Fv-2911 | ARYFWWYGFDY | SEQ ID NO: 163 |
| Fv-2912 | ARTVRGSKKPYFSGWAMDY | SEQ ID NO: 164 |

TABLE 4C-continued

Amino acid sequences of CDR-H3 of anti-FZD5
antibody variable regions identified.

| Antibody variable region ID | CDR-H3 amino acid sequence | SEQ ID NO. |
|---|---|---|
| Fv-2913 | ARYGYYGLDY | SEQ ID NO: 165 |
| Fv-2914 | ARGAMDY | SEQ ID NO: 162 |
| Fv-2915 | ARGYHYYPYYSGLDY | SEQ ID NO: 166 |
| Fv-2916 | ARYGYYGMDY | SEQ ID NO: 167 |
| Fv-2917 | ARAVWYYWWVWGGFDY | SEQ ID NO: 168 |
| Fv-2918 | ARFGYWAIDY | SEQ ID NO: 169 |
| Fv-2919 | ARGAIDY | SEQ ID NO: 155 |
| Fv-2920 | ARGGMDY | SEQ ID NO: 170 |
| Fv-2921 | ARGAMDY | SEQ ID NO: 162 |
| Fv-2922 | ARTVRGSKKPYFSGWAMDY | SEQ ID NO: 171 |
| Fv-2923 | ARGAMDY | SEQ ID NO: 162 |
| Fv-2924 | ARGALDY | SEQ ID NO: 153 |
| Fv-2925 | ARYGYFGLDY | SEQ ID NO: 172 |
| Fv-2926 | ARGGLDY | SEQ ID NO: 173 |
| Fv-2927 | ARYGYYGFDY | SEQ ID NO: 174 |
| Fv-2928 | ARYYAMDY | SEQ ID NO: 175 |
| Fv-2929 | ARGAMDY | SEQ ID NO: 162 |
| Fv-2930 | ARGALDY | SEQ ID NO: 153 |
| Fv-2931 | ARGSYWYVGGGWWVSGHGGMDY | SEQ ID NO: 176 |

TABLE 4C-continued

Amino acid sequences of CDR-H3 of anti-FZD5
antibody variable regions identified.

| Antibody variable region ID | CDR-H3 amino acid sequence | SEQ ID NO. |
|---|---|---|
| Fv-2932 | ARGALDY | SEQ ID NO: 153 |
| Fv-2933 | ARTVRGSKKPYFSGWAMDY | SEQ ID NO: 177 |
| Fv-2934 | ARGAIDY | SEQ ID NO: 155 |
| Fv-2935 | ARAAFDY | SEQ ID NO: 178 |
| Fv-2936 | ARAAMDY | SEQ ID NO: 179 |

TABLE 5A

Nucleic acid sequence encoding CDR-L1 of anti-FZD5
antibody variable regions identified.

| Antibody variable region IDs | Nucleic acid sequence encoding CDR-L1 | SEQ ID NO. |
|---|---|---|
| Fv-2898 to Fv-2936 | 5'-CAGTCCGTGTCCAGCGCT-3' | SEQ ID NO: 180 |

TABLE 5B

Nucleic acid sequence encoding CDR-L2 of anti-FZD5
antibody variable regions identified.

| Variable region IDs | Nucleic acid sequence encoding CDR-L2 | SEQ ID NO. |
|---|---|---|
| Fv-2898 to Fv-2936 | 5'-TCGGCATCC-3' | SEQ ID NO: 181 |

TABLE 5C

Nucleic acid sequences encoding CDR-L3 of anti-FZD5
antibody variable regions identified.

| Antibody variable region ID | Nucleic acid sequence encoding CDR-L3 | SEQ ID NO. |
|---|---|---|
| Fv-2898 | 5'-CAGCAATGGTGGGGTTACTACTCTCTGATCACG-3' | SEQ ID NO: 182 |
| Fv-2899 | 5'-CAGCAATGGTACTCTTCTTACGGTCTGATCACG-3' | SEQ ID NO: 183 |
| Fv-2900 | 5'-CAGCAATGGTACTCTGGTTCTTCTCTGTTCACG-3' | SEQ ID NO: 184 |
| Fv-2901 | 5'-CAGCAAGGTGGTTTCCTGATCACG-3' | SEQ ID NO: 185 |
| Fv-2902 | 5'-CAGCAATGGTACGCTTTCGGTGCTCTGATCACG-3' | SEQ ID NO: 186 |
| Fv-2903 | 5'-CAGCAATGGGGTGGTGGTTCTTCTCTGTTCACG-3' | SEQ ID NO: 187 |
| Fv-2904 | 5'-CAGCAATCTTCTTATTCTCTGATCACG-3' | SEQ ID NO: 188 |
| Fv-2905 | 5'-CAGCAATCTTCTTGGTACTACGGTTACCCGTTCACG-3' | SEQ ID NO: 189 |
| Fv-2906 | 5'-CAGCAATGGTCTTGGGGTTTCCTGATCACG-3' | SEQ ID NO: 190 |
| Fv-2907 | 5'-CAGCAAGTTGGTTACTGGTGGGGTCTGATCACG-3' | SEQ ID NO: 191 |
| Fv-2908 | 5'-CAGCAATCTTCTTATTCTCTGATCACG-3' | SEQ ID NO: 192 |

TABLE 5C-continued

Nucleic acid sequences encoding CDR-L3 of anti-FZD5
antibody variable regions identified.

| Antibody variable region ID | Nucleic acid sequence encoding CDR-L3 | SEQ ID NO. |
|---|---|---|
| Fv-2909 | 5'-CAGCAATCTTGGTCTTACCATTACCTGATCACG-3' | SEQ ID NO: 193 |
| Fv-2910 | 5'-CAGCAATGGTACGGTTCTCATCTGATCACG-3' | SEQ ID NO: 194 |
| Fv-2911 | 5'-CAGCAAGGTCCGTGGTACCCGTTCACG-3' | SEQ ID NO: 195 |
| Fv-2912 | 5'-CAGCAATTCTACTTCCCGTACCTGATCACG-3' | SEQ ID NO: 196 |
| Fv-2913 | 5'-CAGCAATGGGGTGTTTCTCATTACCTGTTCACG-3' | SEQ ID NO: 197 |
| Fv-2914 | 5'-CAGCAATGGTACTACGGTTCTCTGATCACG-3' | SEQ ID NO: 198 |
| Fv-2915 | 5'-CAGCAAGCTTACTACCATTCTCTGATCACG-3' | SEQ ID NO: 199 |
| Fv-2916 | 5'-CAGCAATGGTACCATTACCCGTACCTGATCACG-3' | SEQ ID NO: 200 |
| Fv-2917 | 5'-CAGCAATCTTCTTATTCTCTGATCACG-3' | SEQ ID NO: 201 |
| Fv-2918 | 5'-CAGCAAGCTTTCGGTGCTTCTCTGTTCACG-3' | SEQ ID NO: 202 |
| Fv-2919 | 5'-CAGCAATGGTACTCTTCTGGTCATGTTCTGATCACG-3' | SEQ ID NO: 203 |
| Fv-2920 | 5'-CAGCAATGGTTCGCTGGTGCTCTGATCACG-3' | SEQ ID NO: 204 |
| Fv-2921 | 5'-CAGCAATGGTACGCTGGTTCTCTGATCACG-3' | SEQ ID NO: 205 |
| Fv-2922 | 5'-CAGCAATCTTTCGTTTACCCGTACCTGATCACG-3' | SEQ ID NO: 206 |
| Fv-2923 | 5'-CAGCAATGGTACGGTTACTCTGCTCTGATCACG-3' | SEQ ID NO: 207 |
| Fv-2924 | 5'-CAGCAATGGTACTCTGGTCATTCTCTGATCACG-3' | SEQ ID NO: 208 |
| Fv-2925 | 5'-CAGCAAGCTTGGGTTTACGCTTCTCTGTTCACG-3' | SEQ ID NO: 209 |
| Fv-2926 | 5'-CAGCAATGGTACCATGGTGGTTCTCTGTTCACG-3' | SEQ ID NO: 210 |
| Fv-2927 | 5'-CAGCAATGGGGTTCTCATGGTTACCTGATCACG-3' | SEQ ID NO: 211 |
| Fv-2928 | 5'-CAGCAAGCTTTCTACTACCCGATCACG-3' | SEQ ID NO: 212 |
| Fv-2929 | 5'-CAGCAATGGTACTCTTCTTACGGTCTGATCACG-3' | SEQ ID NO: 213 |
| Fv-2930 | 5'-CAGCAATGGTACGGTCCGTACCTGATCACG-3' | SEQ ID NO: 214 |
| Fv-2931 | 5'-CAGCAATCTTCTTATTCTCTGATCACG-3' | SEQ ID NO: 215 |
| Fv-2932 | 5'-CAGCAATGGTACGGTTCTTTCGCTCTGATCACG-3' | SEQ ID NO: 216 |
| Fv-2933 | 5'-CAGCAATTCTGGTGGTACGCTTCTTGGCTGTTCACG-3' | SEQ ID NO: 217 |
| Fv-2934 | 5'-CAGCAATGGTACCATTACGGTCTGATCACG-3' | SEQ ID NO: 218 |
| Fv-2935 | 5'-CAGCAATGGTACGGTGGTTACGCTCTGATCACG-3' | SEQ ID NO: 219 |
| Fv-2936 | 5'-CAGCAATGGTACGCTGCTTCTCTGATCACG-3' | SEQ ID NO: 220 |

TABLE 6A

Nucleic acid sequences encoding CDR-H1 and the amino
acid residue at position 39 of anti-FZD5 antibody variable
regions identified.

| Antibody variable region ID | Nucleic acid sequence encoding CDR-H1 | SEQ ID NO. of nucleic acid sequence encoding CDR-H1 | Nucleic acid sequence encoding amino acid residue at position 39 |
|---|---|---|---|
| Fv-2898 | 5'-GGCTTCAACATCTATTCTTATTCT-3' | SEQ ID NO: 221 | ATG |
| Fv-2899 | 5'-GGCTTCAACCTCTATTATTATTAT-3' | SEQ ID NO: 222 | ATG |
| Fv-2900 | 5'-GGCTTCAACCTCTCTTCTTATTAT-3' | SEQ ID NO: 223 | ATC |
| Fv-2901 | 5'-GGCTTCAACATCTCTTATTCTTAT-3' | SEQ ID NO: 224 | ATG |
| Fv-2902 | 5'-GGCTTCAACATCTCTTATTATTAT-3' | SEQ ID NO: 225 | ATC |
| Fv-2903 | 5'-GGCTTCAACCTCTCTTATTATTAT-3' | SEQ ID NO: 226 | ATC |
| Fv-2904 | 5'-GGCTTCAACATCTATTCTTATTCT-3' | SEQ ID NO: 227 | ATG |
| Fv-2905 | 5'-GGCTTCAACCTCTCTTATTATTAT-3' | SEQ ID NO: 228 | ATG |
| Fv-2906 | 5'-GGCTTCAACTTTTCTTCTTCTTCT-3' | SEQ ID NO: 229 | ATA |
| Fv-2907 | 5'-GGCTTCAACATCTATTCTTCTTAT-3' | SEQ ID NO: 230 | ATG |
| Fv-2908 | 5'-GGCTTCAACTTTTCTTCTTCTTCT-3' | SEQ ID NO: 231 | ATA |
| Fv-2909 | 5'-GGCTTCAACATCTCTTCTTCTTAT-3' | SEQ ID NO: 232 | ATG |
| Fv-2910 | 5'-GGCTTCAACATCTCTTATTCTTAT-3' | SEQ ID NO: 233 | ATG |
| Fv-2911 | 5'-GGCTTCAACATCTATTATTCTTCT-3' | SEQ ID NO: 234 | ATG |
| Fv-2912 | 5'-GGCTTCAACATCTCTTATTCTTAT-3' | SEQ ID NO: 235 | ATC |
| Fv-2913 | 5'-GGCTTCAACATCTCTTATTCTTCT-3' | SEQ ID NO: 236 | ATC |
| Fv-2914 | 5'-GGCTTCAACATCTATTATTCTTAT-3' | SEQ ID NO: 237 | ATG |
| Fv-2915 | 5'-GGCTTCAACATCTATTATTATTCT-3' | SEQ ID NO: 238 | ATG |
| Fv-2916 | 5'-GGCTTCAACATCTCTTATTCTTCT-3' | SEQ ID NO: 239 | ATC |
| Fv-2917 | 5'-GGCTTCAACTTTTCTTCTTCTTCT-3' | SEQ ID NO: 240 | ATA |
| Fv-2918 | 5'-GGCTTCAACCTCTCTTATTCTTCT-3' | SEQ ID NO: 241 | ATC |
| Fv-2919 | 5'-GGCTTCAACATCTCTTATTCTTAT-3' | SEQ ID NO: 242 | ATC |
| Fv-2920 | 5'-GGCTTCAACATCTCTTATTATTAT-3' | SEQ ID NO: 243 | ATC |
| Fv-2921 | 5'-GGCTTCAACATCTCTTATTATTAT-3' | SEQ ID NO: 244 | ATC |
| Fv-2922 | 5'-GGCTTCAACATCTATTCTTCTTAT-3' | SEQ ID NO: 245 | ATG |
| Fv-2923 | 5'-GGCTTCAACCTCTATTATTATTAT-3' | SEQ ID NO: 246 | ATG |
| Fv-2924 | 5'-GGCTTCAACATCTCTTATTCTTAT-3' | SEQ ID NO: 247 | ATC |
| Fv-2925 | 5'-GGCTTCAACCTCTCTTATTCTTCT-3' | SEQ ID NO: 248 | ATG |
| Fv-2926 | 5'-GGCTTCAACATCTATTCTTCTTAT-3' | SEQ ID NO: 249 | ATG |
| Fv-2927 | 5'-GGCTTCAACATCTATTATTCTTCT-3' | SEQ ID NO: 250 | ATG |
| Fv-2928 | 5'-GGCTTCAACATCTCTTATTCTTCT-3' | SEQ ID NO: 251 | ATC |
| Fv-2929 | 5'-GGCTTCAACATCTCTTATTATTAT-3' | SEQ ID NO: 252 | ATC |
| Fv-2930 | 5'-GGCTTCAACCTCTCTTATTATTAT-3' | SEQ ID NO: 253 | ATC |
| Fv-2931 | 5'-GGCTTCAACCTCTCTTATTCTTCT-3' | SEQ ID NO: 254 | ATG |
| Fv-2932 | 5'-GGCTTCAACATCTCTTATTCTTAT-3' | SEQ ID NO: 255 | ATG |

TABLE 6A-continued

Nucleic acid sequences encoding CDR-H1 and the amino
acid residue at position 39 of anti-FZD5 antibody variable
regions identified.

| Antibody variable region ID | Nucleic acid sequence encoding CDR-H1 | SEQ ID NO. of nucleic acid sequence encoding CDR-H1 | Nucleic acid sequence encoding amino acid residue at position 39 |
|---|---|---|---|
| Fv-2933 | 5'-GGCTTCAACCTCTATTCTTCTTAT-3' | SEQ ID NO: 256 | ATG |
| Fv-2934 | 5'-GGCTTCAACATCTCTTATTCTTAT-3' | SEQ ID NO: 257 | ATG |
| Fv-2935 | 5'-GGCTTCAACATCTATTATTATTAT-3' | SEQ ID NO: 258 | ATC |
| Fv-2936 | 5'-GGCTTCAACATCTCTTATTATTAT-3' | SEQ ID NO: 259 | ATG |

TABLE 6B

Nucleic acid sequences encoding CDR H2 and the
amino acid residues at positions 55 and 66 of anti-FZD5
antibody variable regions identified.

| Antibody variable region ID | Nucleic acid sequence encoding CDR-H2 | SEQ ID NO. of nucleic acid encoding CDR-H2 | Nucleic acid sequence encoding amino acid residue at position 55 | Nucleic acid sequence encoding amino acid residue at position 66 |
|---|---|---|---|---|
| Fv-2898 | 5'-ATTTATTCTTCTTCTGGCTCTACT-3' | SEQ ID NO: 260 | TCT | TCT |
| Fv-2899 | 5'-ATTTATCCTTCTTCTGGCTCTACT-3' | SEQ ID NO: 261 | TCT | TCT |
| Fv-2900 | 5'-ATTTCTTCTTCTTCTAGCTCTACT-3' | SEQ ID NO: 262 | TCT | TCT |
| Fv-2901 | 5'-ATTTATTCTTATTCTAGCTATACT-3' | SEQ ID NO: 263 | TCT | TAT |
| Fv-2902 | 5'-ATTTCTTCTTCTTCTAGCTCTACT-3' | SEQ ID NO: 264 | TCT | TCT |
| Fv-2903 | 5'-ATTTATCCTTATTCTAGCTATACT-3' | SEQ ID NO: 265 | TCT | TCT |
| Fv-2904 | 5'-ATTTCTTCTTCTTATGGCTATACT-3' | SEQ ID NO: 266 | TAT | TCT |
| Fv-2905 | 5'-ATTTATTCTTCTTATAGCTATACT-3' | SEQ ID NO: 267 | TCT | TCT |
| Fv-2906 | 5'-ATTTCTTCTTCTTATGGCTATACT-3' | SEQ ID NO: 268 | TAT | TAT |
| Fv-2907 | 5'-ATTTCTTCTTATTCTGGCTCTACT-3' | SEQ ID NO: 269 | TCT | TAT |
| Fv-2908 | 5'-ATTTATCCTTCTTATAGCTATACT-3' | SEQ ID NO: 270 | TAT | TAT |
| Fv-2909 | 5'-ATTTCTTCTTCTTCTGGCTATACT-3' | SEQ ID NO: 271 | TCT | TCC |
| Fv-2910 | 5'-ATTTATTCTTCTTCTAGCTCTACT-3' | SEQ ID NO: 272 | TCT | TCT |
| Fv-2911 | 5'-ATTTATCCTTATTCTGGCTATACT-3' | SEQ ID NO: 273 | TAT | TCT |
| Fv-2912 | 5'-ATTTCTTCTTCTTCTGGCTATACT-3' | SEQ ID NO: 274 | TCT | TCT |
| Fv-2913 | 5'-ATTTATCCTTATTCTAGCTCTACT-3' | SEQ ID NO: 275 | TCT | TCT |
| Fv-2914 | 5'-ATTTATCCTTCTTCTAGCTCTACT-3' | SEQ ID NO: 276 | TCT | TCT |
| Fv-2915 | 5'-ATTTATTCTTCTTATGGCTATACT-3' | SEQ ID NO: 277 | TCT | TCT |
| Fv-2916 | 5'-ATTTATCCTTCTTATAGCTATACT-3' | SEQ ID NO: 278 | TCT | TAT |
| Fv-2917 | 5'-ATTTCTTCTTCTTATGGCTATACT-3' | SEQ ID NO: 279 | TCT | TAT |
| Fv-2918 | 5'-ATTTATTCTTCTTATAGCTCTACT-3' | SEQ ID NO: 280 | TCT | TCT |
| Fv-2919 | 5'-ATTTATTCTTCTTCTGGCTCTACT-3' | SEQ ID NO: 281 | TCT | TCT |
| Fv-2920 | 5'-ATTTATCCTTCTTCTGGCTCTACT-3' | SEQ ID NO: 282 | TCT | TCT |
| Fv-2921 | 5'-ATTTATCCTTCTTCTGGCTCTACT-3' | SEQ ID NO: 283 | TCT | TCT |

TABLE 6B-continued

Nucleic acid sequences encoding CDR H2 and the
amino acid residues at positions 55 and 66 of anti-FZD5
antibody variable regions identified.

| Antibody variable region ID | Nucleic acid sequence encoding CDR-H2 | SEQ ID NO. of nucleic acid encoding CDR-H2 | Nucleic acid sequence encoding amino acid residue at position 55 | Nucleic acid sequence encoding amino acid residue at position 66 |
|---|---|---|---|---|
| Fv-2922 | 5'-ATTTCTCCTTATTCTGGCTATACT-3' | SEQ ID NO: 284 | TCT | TCT |
| Fv-2923 | 5'-ATTTATTCTTCTTCTGGCTCTACT-3' | SEQ ID NO: 285 | TCT | TCT |
| Fv-2924 | 5'-ATTTATTCTTATTATAGCTCTACT-3' | SEQ ID NO: 286 | TCT | TCT |
| Fv-2925 | 5'-ATTTATCCTTCTTATGGCTCTACT-3' | SEQ ID NO: 287 | TCT | TAT |
| Fv-2926 | 5'-ATTTATCCTTCTTCTAGCTCTACT-3' | SEQ ID NO: 288 | TCT | TCT |
| Fv-2927 | 5'-ATTTATCCTTCTTATGGCTATACT-3' | SEQ ID NO: 289 | TCT | TCT |
| Fv-2928 | 5'-ATTTATCCTTCTTATAGCTCTACT-3' | SEQ ID NO: 290 | TCT | TAT |
| Fv-2929 | 5'-ATTTATCCTTCTTCTAGCTCTACT-3' | SEQ ID NO: 291 | TCT | TCT |
| Fv-2930 | 5'-ATTTATCCTTATTCTGGCTCTACT-3' | SEQ ID NO: 292 | TCT | TCT |
| Fv-2931 | 5'-ATTTCTCCTTATTCTGGCTCTACT-3' | SEQ ID NO: 293 | TAT | TAT |
| Fv-2932 | 5'-ATTTATTCTTCTTATAGCTCTACT-3' | SEQ ID NO: 294 | TCT | TCT |
| Fv-2933 | 5'-ATTTATTCTTCTTATGGCTATACT-3' | SEQ ID NO: 295 | TCT | TCT |
| Fv-2934 | 5'-ATTTATTCTTCTTCTGGCTCTACT-3' | SEQ ID NO: 296 | TCT | TCT |
| Fv-2935 | 5'-ATTTATCCTTCTTCTGGCTCTACT-3' | SEQ ID NO: 297 | TCT | TCT |
| Fv-2936 | 5'-ATTTATTCTTCTTCTGGCTCTACT-3' | SEQ ID NO: 298 | TCT | TCT |

TABLE 6C

Nucleic acid sequences encoding CDR-H3 of anti-FZD5
antibody variable regions identified.

| Antibody variable region ID | Nucleic acid sequence encoding CDR-H3 | SEQ ID NO. |
|---|---|---|
| Fv-2898 | 5'-GCTCGCGCTGTTTGGGGTTTGGACTAC-3' | SEQ ID NO: 299 |
| Fv-2899 | 5'-GCTCGCGGTGCTTTGGACTAC-3' | SEQ ID NO: 300 |
| Fv-2900 | 5'-GCTCGCGGTGCTTTGGACTAC-3' | SEQ ID NO: 301 |
| Fv-2901 | 5'-GCTCGCTCTTGGTACTACTGGTCTCCGTCTTCTGGTATGGACTAC-3' | SEQ ID NO: 302 |
| Fv-2902 | 5'-GCTCGCGGTGCTTTGGACTAC-3' | SEQ ID NO: 303 |
| Fv-2903 | 5'-GCTCGCGGTGCTATTGACTAC-3' | SEQ ID NO: 304 |
| Fv-2904 | 5'-GCTCGCTCTTGGTACGCTTGGGCTATGGACTAC-3' | SEQ ID NO: 305 |
| Fv-2905 | 5'-GCTCGCTCTGGTTACGCTTTGGACTAC-3' | SEQ ID NO: 306 |
| Fv-2906 | 5'-GCTCGCACTGTTCGTGGATCCAAAAAACCGTACTTCTCTGGTTGGGCTATGGACTAC-3' | SEQ ID NO: 307 |
| Fv-2907 | 5'-GCTCGCTCTTCTTGGGGTGCTTACATTGTTTCTTACGGTTTTGACTAC-3' | SEQ ID NO: 308 |
| Fv-2908 | 5'-GCTCGCGCTTACTACGGTCATTTCCATGCTATGGACTAC-3' | SEQ ID NO: 309 |
| Fv-2909 | 5'-GCTCGCACTGTTCGTGGATCCAAAAAACCGTACTTCTCTGGTTGGGCTATGGACTAC-3' | SEQ ID NO: 310 |

TABLE 6C-continued

Nucleic acid sequences encoding CDR-H3 of anti-FZD5
antibody variable regions identified.

| Antibody variable region ID | Nucleic acid sequence encoding CDR-H3 | SEQ ID NO. |
|---|---|---|
| Fv-2910 | 5'-GCTCGCGGTGCTATGGACTAC-3' | SEQ ID NO: 311 |
| Fv-2911 | 5'-GCTCGCTACTTCTGGTGGTACGGTTTTGACTAC-3' | SEQ ID NO: 312 |
| Fv-2912 | 5'-GCTCGCACTGTTCGTGGATCCAAAAAACCGTACTTCTCTGGTT GGGCTATGGACTAC-3' | SEQ ID NO: 313 |
| Fv-2913 | 5'-GCTCGCTACGGTTACTACGGTTTGGACTAC-3' | SEQ ID NO: 314 |
| Fv-2914 | 5'-GCTCGCGGTGCTATGGACTAC-3' | SEQ ID NO: 315 |
| Fv-2915 | 5'-GCTCGCGGTTACCATTACTACCCGTACTACTCTGGTTTGGACT AC-3' | SEQ ID NO: 316 |
| Fv-2916 | 5'-GCTCGCTACGGTTACTACGGTATGGACTAC-3' | SEQ ID NO: 317 |
| Fv-2917 | 5'-GCTCGCGCTGTTTGGTACTACTGGTGGGTTTGGGGTGGTTTTG ACTAC-3' | SEQ ID NO: 318 |
| Fv-2918 | 5'-GCTCGCTTCGGTTACTGGGCTATTGACTAC-3' | SEQ ID NO: 319 |
| Fv-2919 | 5'-GCTCGCGGTGCTATTGACTAC-3' | SEQ ID NO: 320 |
| Fv-2920 | 5'-GCTCGCGGTGGTATGGACTAC-3' | SEQ ID NO: 321 |
| Fv-2921 | 5'-GCTCGCGGTGCTATGGACTAC-3' | SEQ ID NO: 322 |
| Fv-2922 | 5'-GCTCGCACTGTTCGTGGATCCAAAAAACCGTACTTCTCTGGTT GGGCTATGGACTAC-3' | SEQ ID NO: 323 |
| Fv-2923 | 5'-GCTCGCGGTGCTATGGACTAC-3' | SEQ ID NO: 324 |
| Fv-2924 | 5'-GCTCGCGGTGCTTTGGACTAC-3' | SEQ ID NO: 325 |
| Fv-2925 | 5'-GCTCGCTACGGTTACTTCGGTTTGGACTAC-3' | SEQ ID NO: 326 |
| Fv-2926 | 5'-GCTCGCGGTGGTTTGGACTAC-3' | SEQ ID NO: 327 |
| Fv-2927 | 5'-GCTCGCTACGGTTACTACGGTTTTGACTAC-3' | SEQ ID NO: 328 |
| Fv-2928 | 5'-GCTCGCTACTACGCTATGGACTAC-3' | SEQ ID NO: 329 |
| Fv-2929 | 5'-GCTCGCGGTGCTATGGACTAC-3' | SEQ ID NO: 330 |
| Fv-2930 | 5'-GCTCGCGGTGCTTTGGACTAC-3' | SEQ ID NO: 331 |
| Fv-2931 | 5'-GCTCGCGGTTCTTACTGGTACGTTGGTGGTGGTTGGTGGGTTT CTGGTCATGGTGGTATGGACTAC-3' | SEQ ID NO: 332 |
| Fv-2932 | 5'-GCTCGCGGTGCTTTGGACTAC-3' | SEQ ID NO: 333 |
| Fv-2933 | 5'-GCTCGCACTGTTCGTGGATCCAAAAAACCGTACTTCTCTGGTT GGGCTATGGACTAC-3' | SEQ ID NO: 334 |
| Fv-2934 | 5'-GCTCGCGGTGCTATTGACTAC-3' | SEQ ID NO: 335 |
| Fv-2935 | 5'-GCTCGCGCTGCTTTTGACTAC-3' | SEQ ID NO: 336 |
| Fv-2936 | 5'-GCTCGCGCTGCTATGGACTAC-3' | SEQ ID NO: 337 |

TABLE 7

Amino acid sequences (and nucleic acid sequences encoding same)
of FRs and FR segments which are identical in all 39 of antibody variable
regions Fv-2898 to Fv-2936 (and hence in any Frizzled protein-binding
agent, such as a Fab or antibody, having one of these antibody variable
regions).

| Domain | FR/FR segment (or nucleic acid sequence encoding same) | Sequence | SEQ ID NO. |
|---|---|---|---|
| VL | FR1 amino acid sequence | DIQMTQSPSSLSASVGDRVTITCRAS | SEQ ID NO: 352 |
| | FR2 amino acid sequence | VAWYQQKPGKAPKLLIY | SEQ ID NO: 353 |
| | FR3 amino acid sequence | SLYSGVPSRFSGSRSGTDFTLTISSLQPEDF ATYYC | SEQ ID NO: 354 |
| | FR4 amino acid sequence | FGQGTKVEIK | SEQ ID NO: 355 |
| | FR1 nucleic acid sequence | 5'-GATATCCAGATGACCCAGTCCCCGAGCT CCCTGTCCGCCTCTGTGGGCGATAGGGTCAC CATCACCTGCCGTGCCAGT-3' | SEQ ID NO: 356 |
| | FR2 nucleic acid sequence | 5'-GTAGCCTGGTATCAACAGAAACCAGGAA AAGCTCCGAAGCTTCTGATTTAC-3' | SEQ ID NO: 357 |
| | FR3 nucleic acid sequence | 5'-AGCCTCTACTCTACTCTGGAGTCCCTTC TCGCTTCTCTGGTAGCCGTTCCGGGACGGAT TTCACTCTGACCATCAGCAGTCTGCAGCCGG AAGACTTCGCAACTTATTACTGTCAG-3' | SEQ ID NO: 358 |
| | FR4 nucleic acid sequence | 5'-TTCGGACAGGGTACCAAGGTGGAGATCA AA-3' | SEQ ID NO: 359 |
| VH | FR1 amino acid sequence | EVQLVESGGGLVQPGGSLRLSCAAS | SEQ ID NO: 360 |
| | FR2 segment spanning amino acid residue positions 40-54 amino acid sequence | HWVRQAPGKGLEWVA | SEQ ID NO: 361 |
| | FR3 segment spanning amino acid residue positions 67-104 amino acid sequence | YADSVKGRFTISADTSKNTAYLQMNSLRAED TAVYYC | SEQ ID NO: 362 |
| | FR4 amino acid sequence | WGQGTLVTVSS | SEQ ID NO: 363 |
| | FR1 nucleic acid sequence | 5'-GAGGTTCAGCTGGTGGAGTCTGGCGGTG GCCTGGTGCAGCCAGGGGGCTCACTCCGTTT GTCCTGTGCAGCTTCTGGCTTCAAC-3' | SEQ ID NO: 364 |
| | FR2 segment spanning amino acid residue positions 40-54 nucleic acid sequence | 5'-TGGGTGCGTCAGGCCCCGGGTAAGGGCC TGGAATGGGTT-3' | SEQ ID NO: 365 |
| | FR3 segment spanning amino acid residue positions 67-104 nucleic acid sequence | 5'-GCCGATAGCGTCAAGGGCCGTTTCACTA TAAGCGCAGACACATCCAAAAACACAGCCTA CCTACAAATGAACAGCTTAAGAGCTGAGGAC ACTGCCGTCTATTATTGTGCTCGC-3' | SEQ ID NO: 366 |
| | FR4 nucleic acid sequence | 5'-GACTACTGGGGTCAAGGAACCCTGGTCA CCGTCTCCTCG-3' | SEQ ID NO: 367 |

TABLE 8

Amino acid sequences (and nucleic acid sequences encoding same) of
light chain and heavy chain of exemplary anti-FZD5 antibody IgG-2919
having antibody variable region Fv-2919. This Table of shared framework
regions/framework segments enables definition of full-length antibody
sequences for each antibody variable region disclosed (Fv-2998 to Fv-
2936).

Light chain (hK) amino acid sequence:
DIQMTQSPSSLSASVGDRVTITCRASQSVSSAVAWYQQKPGKAPKLLIYSASSLYSGVPSRFSGSRSGTDF
TLTISSLQPEDFATYYCQQWYSSGHVLITFGQGTKVEIKRTVAAPSVFIFPPSDEQLKSGTASVVCLLNNF
YPREAKVQWKVDNALQSGNSQESVTEQDSKDSTYSLSSTLTLSKADYEKHKVYACEVTHQGLSSPVTKSFN
RGEC (SEQ ID NO: 338)

Light chain (hK) nucleic acid sequence:
5'-GATATCCAGATGACCCAGTCCCCGAGCTCCCTGTCCGCCTCTGTGGGCGATAGGGTCACCATCACCTG
CCGTGCCAGTCAGTCCGTGTCCAGCGCTGTAGCCTGGTATCAACAGAAACCAGGAAAAGCTCCGAAGCTTC
TGATTTACTCGGCATCCAGCCTCTACTCTACTCTGGAGTCCCTTCTCGCTTCTCTGGTAGCCGTTCCGGGA
CGGATTTCACTCTGACCATCAGCAGTCTGCAGCCGGAAGACTTCGCAACTTATTACTGTCAGCAGCAATGG
TACTCTTCTGGTCATGTTCTGATCACGTTCGGACAGGGTACCAAGGTGGAGATCAAACGTACGGTGGCTGC TABLE 8-continued Amino acid sequences (and nucleic acid sequences encoding same) of
light chain and heavy chain of exemplary anti-FZD5 antibody IgG-2919
having antibody variable region Fv-2919. This Table of shared framework
regions/framework segments enables definition of full-length antibody
sequences for each antibody variable region disclosed (Fv-2998 to Fv-
2936).

*ACCATCTGTCTTCATCTTCCCGCCATCTGATGAGCAGTTGAAATCTGGAACTGCCTCTGTTGTGTGCCTGC
TGAATAACTTCTATCCCAGAGAGGCCAAAGTACAGTGGAAGGTGGATAACGCCCTCCAATCGGGTAACTCC
CAGGAGAGTGTCACAGAGCAGGACAGCAAGGACAGCACCTACAGCCTCAGCAGCACCCTGACGCTGAGCAA
AGCAGACTACGAGAAACACAAAGTCTACGCCTGCGAAGTCACCCATCAGGGCCTGAGCTCGCCCGTCACAA
AGAGCTTCAACAGGGGAGAGTGT-3' (SEQ ID NO: 339)*

Heavy chain (hG1) amino acid sequence:
EVQLVESGGGLVQPGGSLRLSCAASGFNISYSYIHWVRQAPGKGLEWVASIYSSSGSTSYADSVKGRFTI
SADTSKNTAYLQMNSLRAEDTAVYYCARGAIDYWGQGTLVTVS*SASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVVDVSHEDPEVKFNWYVDGVEVHN
AKTKPREEQYNSTYRVVSVLTVLHQDWLNGKYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRWQQGNVFSCSVM
HEALHNHYTQKSLSLSPGK* (SEQ ID NO: 340)

Heavy chain (hG1) nucleic acid sequence:
5'-GAGGTTCAGCTGGTGGAGTCTGGCGGTGGCCTGGTGCAGCCAGGGGGCTCACTCCGTTTGTCCTGTGC
AGCTTCTGGCTTCAACGGCTTCAACATCTCTTATTCTTATATCTGGGTGCGTCAGGCCCCGGGTAAGGGC
CTGGAATGGGTTTCTATTTATTCTTCTTCTGGCTCTACTCTGCCGATAGCGTCAAGGGCCGTTTCACTA
TAAGCGCAGACACATCCAAAAACACAGCCTACCTACAAATGAACAGCTTAAGAGCTGAGGACACTGCCGTC
TATTATTGTGCTCGCGCTCGCGGTGCTATTGACTACGACTACTGGGGTCAAGGAACCCTGGTCACCGTCTC
CTCGGCTAGCACCAAGGGCCCATCGGTCTTCCCCCTGGCACCCTCCTCCAAGAGCACCTCTGGGGGCACAG
CGGCCCTGGGCTGCCTGGTCAAGGACTACTTCCCCGAACCGGTGACGGTGTCGTGGAACTCAGGCGCCCTG
ACCAGCGGCGTGCACACCTTCCCGGCTGTCCTACAGTCCTCAGGACTCTACTCCCTCAGCAGCGTGGTGAC
CGTGCCCTCCAGCAGCTTGGGCACCCAGACCTACATCTGCAACGTGAATCACAAGCCCAGCAACACCAAGG
TGGACAAGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGACCCCTGA
GGTCACATGCGTGGTGGTGGACGTGAGCCACGAAGACCCTGAGGTCAAGTTCAACTGGTACGTGGACGGCG
TGGAGGTGCATAATGCCAAGACAAAGCCGCGGGAGGAGCAGTACAACAGCACGTACCGTGTGGTCAGCGTC
CTCACCGTCCTGCACCAGGACTGGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAACCACAGGTGTACACCCTGCCCC
CATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTC
CGACGGCTCCTTCTTCCTCTACAGCAAGCTCACCGTGGACAAGAGCAGGTGGCAGCAGGGGAACGTCTTCT
CATGCTCCGTGATGCATGAGGCTCTGCACAACCACTACACGCAGAAGAGCCTCTCCCTGTCTCCGGGTAAA-
3' (SEQ ID NO: 341)

1. Underlined identifies CDR residues (or nucleic acid sequence encoding same).
2. Bold/larger font identifies FR residues at positions 39, 55 and 66 (or nucleic acid
sequences encoding same), which similarly to certain CDR positions are designed to be
variable/degenerate in phage-Fab display Library F (described in Persson et al., 2013).
3. Italics identifies constant region residues (or nucleic acid sequence encoding same)

Example 5: Anti-FZD5 Cysteine-Rich Domain (CRD) Fab Panel Capable of Binding and Discriminating FZD1, FZD2, FZD4, FZD5, FZD6, FZD7, FZD8, FZD9 and FZD10

Figure 7B:
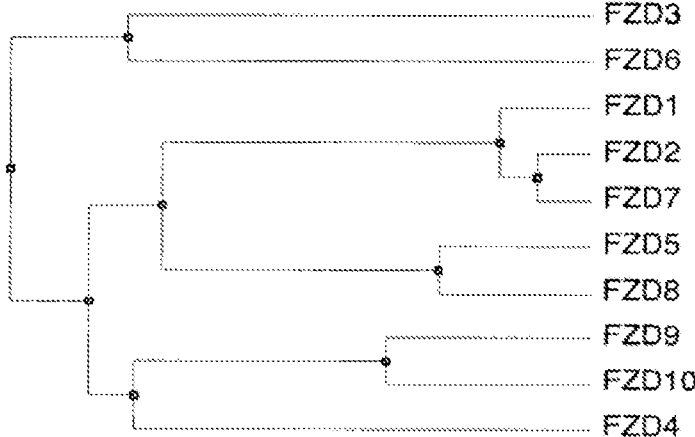
Figure 7C:
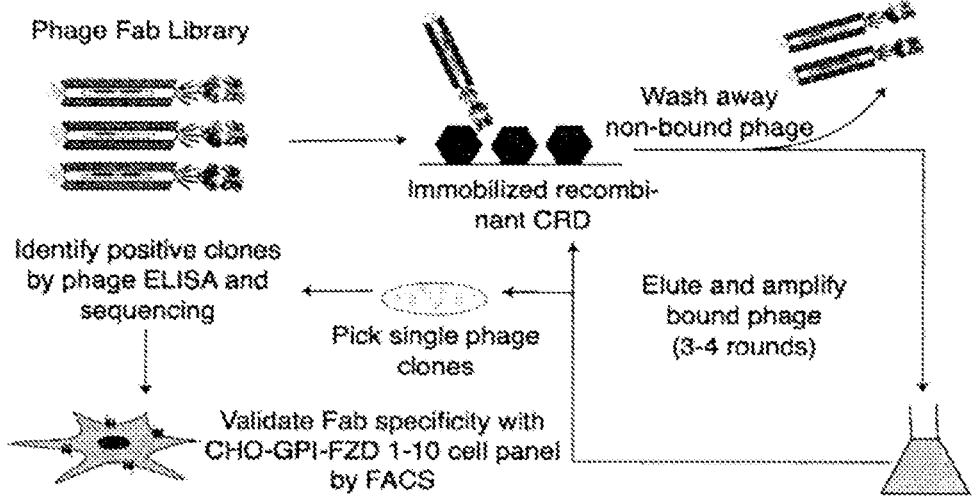
Figure 7D:
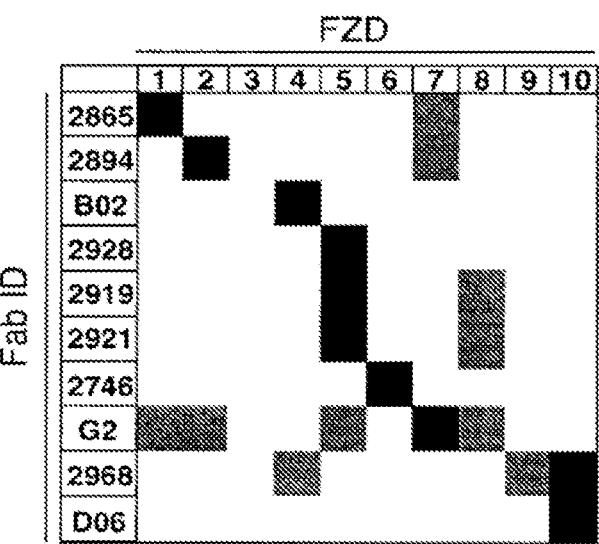
Figure 7E:
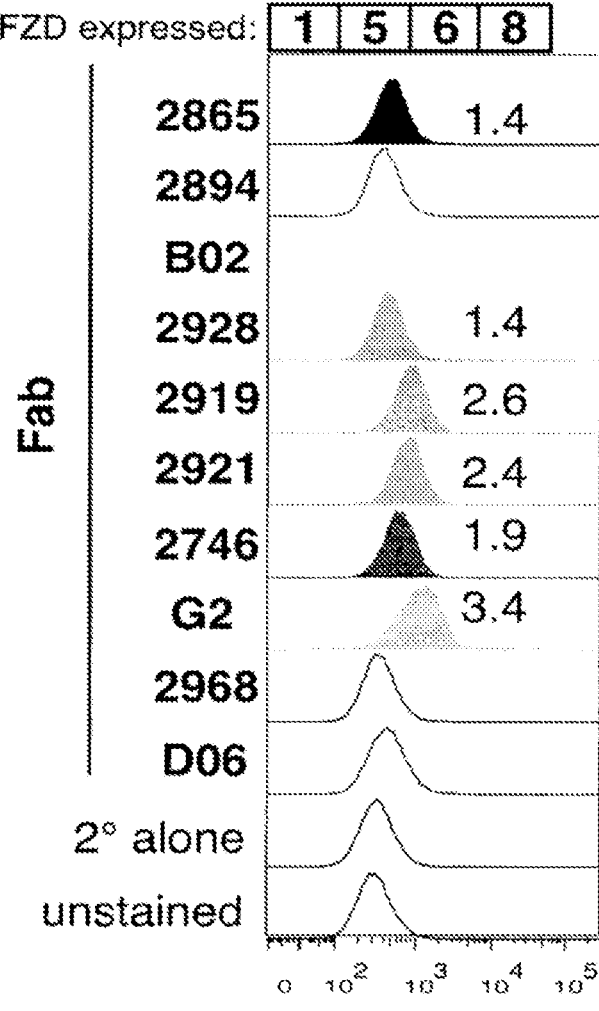
Figure 8:
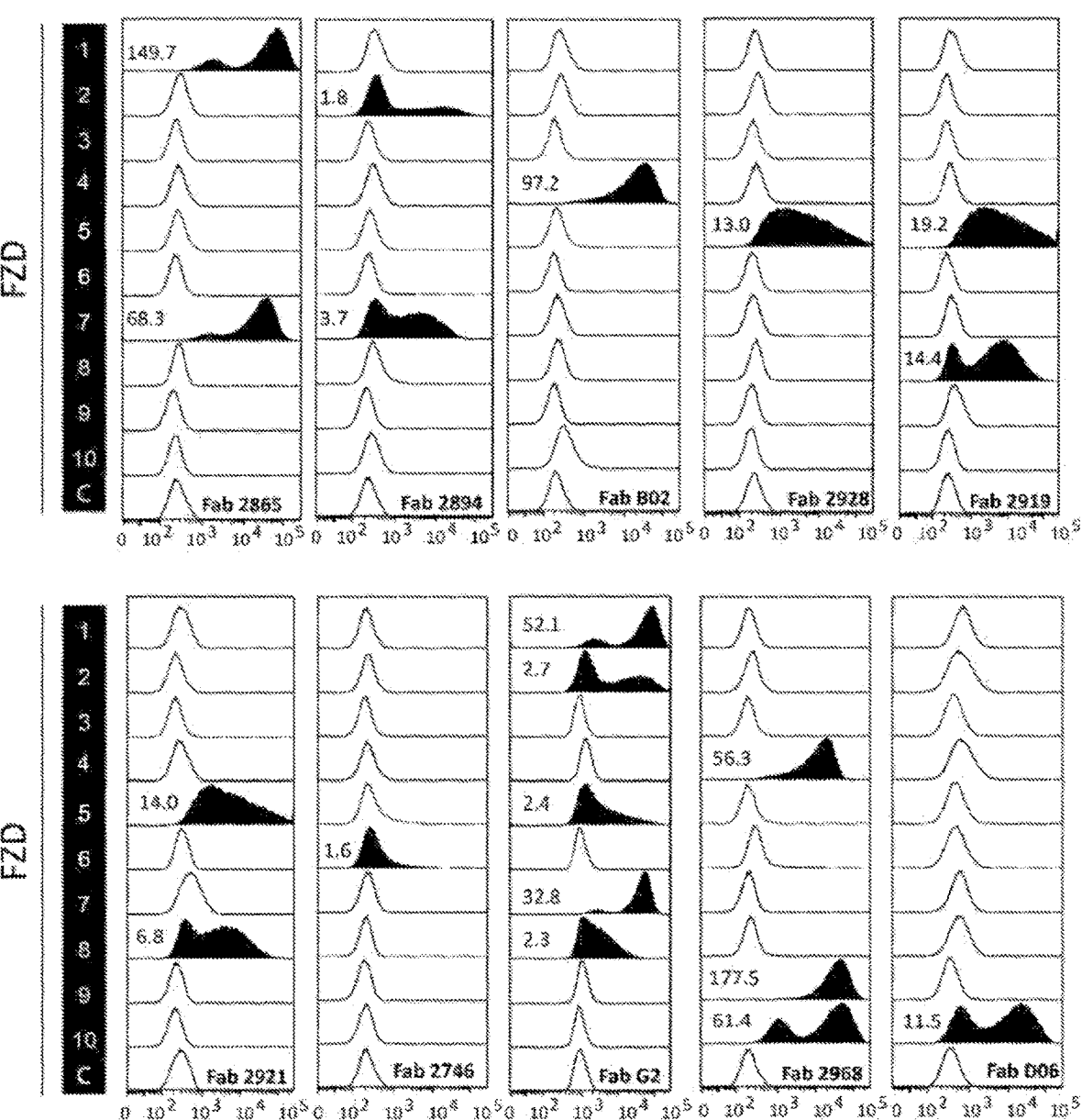

To confirm that the FZD5-WNT7B circuit is not driven simply by expression and rule out the possibility of a disconnect between RNA and protein levels for the Wnt receptors in HPAF-II cells, a panel of recombinant Fabs were generated, alternatively referred to herein as 'Frizzled profiler', that can detect and discriminate all but one of the ten Frizzled receptors. Briefly, a phage-displayed fragment antigen-binding (Fab) library (Persson et al., 2013) was used and binding selections were performed on the purified cysteine-rich domains (CRDs) of FZD1, FZD2, FZD4, FZD5, FZD6, FZD7, FZD8, FZD9 and FZD10 (Table 9, FIG. 7A, FIG. 7B and FIG. 7C). The most selective Fab-phages were chosen for each of the Frizzled CRDs based on Fab-phage ELISAs and these were produced as purified Fabs. To characterize the binding specificity of these Fabs on cells, a panel of 10 CHO cell lines was generated, each expressing the CRD domain of a different myc-tagged Frizzled family member anchored at the plasma membrane through a GPI anchor (CHO-myc-FZDGPI). Despite the high sequence identity between Frizzled family members (FIG. 7A, FIG. 7B), selective Fabs were identified for FZD4, FZD5, FZD6 and FZD10 as assessed by immunofluorescence and flow cytometry (FIG. 7D and FIG. 8). Moreover, Fabs were found that bound to the following combinations of Frizzled family members: FZD1/FZD7; FZD2/FZD7; FZD5/FZD8; FZD1/FZD2/FZD5/FZD7/FZD8; and FZD4/FZD9/FZD10. The FZD8 CRD is most homologous to that of FZD5 (FIG. 7B). These Fabs can be used to discriminate expression of FZD1, FZD2, FZD4, FZD5, FZD6, FZD7, FZD8, FZD9 and FZD10 (FIG. 7D and FIG. 8). The 'Frizzled profiler' therefore consists of 10 different Fabs that can be used to discriminate expression of 9 different Frizzled family members. The Frizzled profiler was then used to confirm that HPAF-II cells express FZD1, FZD5, FZD6 and possibly FZD8 (FIG. 7E).

TABLE 9

| Frizzled protein and CRD | NCBI RefSeq Accession and segment | Amino acid sequence of CRD | SEQ ID NO. |
|---|---|---|---|
| FZD1 | Accession Q9UP38.2, D112-P238 | DHGYCQPISIPLCTDIAYNQTIMPNLLGHTNQEDAGLEVH QFYPLVKVQCSAELKFFLCSMYAPVCTVLEQALPPCRSLC ERARQGCEALMNKFGFQWPDTLKCEKFPVHGAGELCVGQN TSDKGTP | SEQ ID NO: 369 |
| FZD2 | Accession Q14332.1, D35-P161 | DHGFCQPISIPLCTDIAYNQTIMPNLLGHTNQEDAGLEVH QFYPLVKVQCSPELRFFLCSMYAPVCTVLE QAIPPCRSICERARQGCEALMNKFGFQWPERLRCEHFPRH GAEQICVGQNHSEDGAP | SEQ ID NO: 370 |
| FZD4 | Accession Q9ULV1.2, E42-V167 | ERRCDPIRISMCQNLGYNVTKMPNLVGHELQTDAELQLTT FTPLIQYGCSSQLQFFLCSVYVPMCTEKINIPIGPCGGMC LSVKRRCEPVLKEFGFAWPESLNCSKFPPQNDHNHMCMEG PGDEEV | SEQ ID NO: 371 |
| FZD5 | Accession Q13467.2, K29-T156 | KAPVCQEITVPMCRGIGYNLTHMPNQFNHDTQDEAGLEVH QFWPLVEIQCSPDLRFFLCSMYTPICLPDYHKPLPPCRSV CERAKAGCSPLMRQYGFAWPERMSCDRLPVLGRDAEVLCM DYNRSEAT | SEQ ID NO: 372 |
| FZD6 | Accession O60353.2, S20-P146 | SLFTCEPITVPRCMKMAYNMTFFPNLMGHYDQSIAAVEME HFLPLANLECSPNIETFLCKAFVPTCIEQIHVVPPCRKLC EKVYSDCKKLIDTFGIRWPEELECDRLQYCDETVPVTFDP HTEFLGP | SEQ ID NO: 373 |
| FZD7 | Accession O75084.2, D45-S169 | DHGFCQPISIPLCTDIAYNQTILPNLLGHTNQEDAGLEVH QFYPLVKVQCSPELRFFLCSMYAPVCTVLDQAIPPCRSLC ERARQGCEALMNKFGFQWPERLRCENFPVHGAGEICVGQN TSDGS | SEQ ID NO: 374 |
| FZD8 | Accession Q9H461.1, K31-D155 | KELACQEITVPLCKGIGYNYTYMPNQFNHDTQDEAGLEVH QFWPLVEIQCSPDLKFFLCSMYTPICLEDYKKPLPPCRSV CERAKAGCAPLMRQYGFAWPDRMRCDRLPEQGNPDTLCMD YNRTD | SEQ ID NO: 375 |
| FZD9 | Accession O00144.1, G35-A161 | GAAPCQAVEIPMCRGIGYNLTRMPNLLGHTSQGEAAAELA EFAPLVQYGCHSHLRFFLCSLYAPMCTDQVSTPIPACRPM CEQARLRCAPIMEQFNFGWPDSLDCARLPTRNDPHALCME APENATA | SEQ ID NO: 376 |
| FZD10 | Accession Q9ULW2.1, 30-156 | GDGKCQPIEIPMCKDIGYNMTRMPNLMGHENQREAAIQLH EFAPLVEYGCHGHLRFFLCSLYAPMCTEQVSTPIPACRVM CEQARLKCSPIMEQFNFKWPDSLDCRKLPNKNDPNYLCME APNNGSD | SEQ ID NO: 377 |

The binding of anti-FZD5 Fabs to cell surface-expressed Frizzled protein was further determined for each member of the Frizzled family via flow cytometry and immunofluorescence analysis of a panel of 10 CHO cell lines, each ectopically over-expressing the extracellular cysteine-rich domain (CRD) of a different Frizzled protein family member. As shown in Table 10 and Table 11, respectively, flow cytometry and immunofluorescence analyses indicated that each of the Fabs binds to FZD5 CRD and, variously, further binds to ORD of at least one of FZD1, FZD2, FZD4, FZD7, FZD8, FZD9 and FZD10.

TABLE 10

Flow cytometry analysis of binding of anti-FZD5 Fabs to cell-surface expressed Frizzled family member CRDs.

| | Frizzled CRD overexpressed on CHO cells | | | | | | | | | |
|---|---|---|---|---|---|---|---|---|---|---|
| Fab ID | None | FZD1 | FZD2 | FZD3 | FZD4 | FZD5 | FZD6 | FZD7 | FZD8 | FZD9 | FZD10 |
| — (2nd Ab-only control) | 3.08 | 3.08 | 3.75 | 3.37 | 3.49 | 3.85 | 2.81 | 2.44 | 2.84 | 3.16 | 2.81 |
| Fab-2898 | 5.38 | 14.86 | 13.46 | 5.05 | 6.26 | 32.05 | 4.49 | 36.85 | 12.69 | 4.57 | 4.26 |
| Fab-2899 | 4.91 | 19.46 | 20.72 | 7.91 | 11.86 | 33.68 | 4.37 | 54.25 | 12.75 | 4.70 | 5.00 |
| Fab-2900 | 3.4 | 31.06 | 6.15 | 4.26 | 5.62 | 38.20 | 3.37 | 8.98 | 23.29 | 3.01 | 3.25 |

TABLE 10-continued

Flow cytometry analysis of binding of anti-FZD5 Fabs to cell-surface expressed Frizzled family member CRDs.

| | | | | | Frizzled CRD overexpressed on CHO cells | | | | | | |
|---|---|---|---|---|---|---|---|---|---|---|---|
| Fab ID | None | FZD1 | FZD2 | FZD3 | FZD4 | FZD5 | FZD6 | FZD7 | FZD8 | FZD9 | FZD10 |
| Fab-2901 | 3.75 | 17.08 | 13.95 | 4.1 | 5.09 | 32.78 | 3.62 | 46.98 | 10.94 | 3.25 | 3.85 |
| Fab-2902 | 4.66 | 6.1 | 8.98 | 6.44 | 10.27 | 36.85 | 4.00 | 15.96 | 13.94 | 3.96 | 4.10 |
| Fab-2903 | 4.07 | 8.66 | 10.84 | 4.18 | 5.52 | 34.91 | 3.52 | 8.58 | 13.70 | 3.11 | 3.05 |
| Fab-2904 | 4.57 | 15.54 | 11.97 | 4.14 | 55.23 | 29.69 | 3.59 | 42.94 | 10.09 | 3.37 | 3.43 |
| Fab-2905 | 3.62 | 3.75 | 5.09 | 4.1 | 4.57 | 24.80 | 3.22 | 3.43 | 8.17 | 3.25 | 3.31 |
| Fab-2906 | 3.89 | 5.23 | 5.09 | 4.03 | 12.3 | 30.23 | 3.55 | 2.92 | 10.09 | 5.05 | 19.81 |
| Fab-2907 | 3.43 | 3.28 | 4.07 | 3.79 | 3.96 | 32.78 | 3.06 | 2.62 | 11.76 | 2.86 | 2.76 |
| Fab-2908 | 3.46 | 8.13 | 9.31 | 3.22 | 4.57 | 25.48 | 2.89 | 35.87 | 5.52 | 3.13 | 3.08 |
| Fab-2909 | 3.4 | 4.61 | 5.38 | 3.43 | 4.1 | 31.34 | 2.89 | 4.57 | 7.43 | 2.57 | 2.71 |
| Fab-2910 | 2.92 | 6.67 | 4.47 | 3.28 | 5 | 30.51 | 2.79 | 10.18 | 7.91 | 2.74 | 2.81 |
| Fab-2911 | 4.53 | 38.2 | 22.67 | 4.96 | 6.21 | 20.54 | 3.68 | 43.32 | 7.43 | 4.10 | 3.96 |
| Fab-2912 | 4.49 | 41.05 | 19.81 | 4.61 | 46.98 | 32.20 | 4.10 | 56.74 | 7.57 | 4.45 | 3.82 |
| Fab-2913 | 3.85 | 17.47 | 14.07 | 4.61 | 5.57 | 27.14 | 3.62 | 34.91 | 8.98 | 3.79 | 3.75 |
| Fab-2914 | 4.37 | 40.32 | 18.94 | 4.61 | 5.52 | 31.91 | 3.59 | 18.43 | 8.90 | 3.82 | 3.72 |
| Fab-2915 | 4.49 | 36.85 | 22.07 | 5.05 | 5.99 | 27.63 | 3.37 | 40.68 | 10.00 | 3.92 | 3.92 |
| Fab-2916 | 4.22 | 34.29 | 18.94 | 4.53 | 6.1 | 24.14 | 3.49 | 36.19 | 7.37 | 3.52 | 2.94 |
| Fab-2917 | 3.43 | 13.46 | 5.57 | 3.46 | 4.14 | 30.23 | 2.89 | 20.54 | 8.58 | 3.49 | 2.76 |
| Fab-2918 | 3.13 | 11.97 | 4.41 | 3.55 | 4.07 | 29.16 | 2.69 | 7.50 | 7.57 | 3.11 | 2.81 |
| Fab-2919 | 3.08 | 3.52 | 4.26 | 3.96 | 3.79 | 43.71 | 2.64 | 2.41 | 20.54 | 2.79 | 2.48 |
| Fab-2920 | 3.37 | 5.73 | 4.57 | 3.75 | 4.22 | 28.64 | 3.02 | 4.91 | 7.50 | 2.89 | 2.94 |
| Fab-2921 | 3.22 | 4.53 | 4.37 | 3.59 | 4.1 | 29.43 | 2.67 | 4.37 | 6.98 | 2.94 | 2.48 |
| Fab-2922 | 3.89 | 4.83 | 4.78 | 4.1 | 12.75 | 56.23 | 3.68 | 2.62 | 9.14 | 2.89 | 2.74 |
| Fab-2923 | 4.22 | 6.04 | 7.91 | 6.67 | 10.55 | 36.85 | 4.33 | 6.04 | 11.86 | 4.83 | 4.22 |
| Fab-2924 | 4.1 | 6.26 | 6.73 | 4.7 | 6.38 | 39.24 | 4.49 | 6.49 | 12.08 | 4.49 | 4.78 |
| Fab-2925 | 3.55 | 19.46 | 10.65 | 3.92 | 4.53 | 37.52 | 3.05 | 24.14 | 7.70 | 3.31 | 4.53 |
| Fab-2926 | 3.65 | 7.17 | 6.21 | 4.61 | 6.73 | 34.60 | 3.05 | 2.71 | 12.86 | 3.65 | 2.92 |
| Fab-2927 | 3.79 | 18.68 | 17.94 | 4.45 | 5.94 | 28.26 | 3.05 | 16.70 | 10.27 | 3.85 | 3.31 |
| Fab-2928 | 3.68 | 18.43 | 14.59 | 4.37 | 5.19 | 42.94 | 3.08 | 5.94 | 7.57 | 4.49 | 3.96 |
| Fab-2929 | 3.19 | 7.64 | 4.29 | 3.55 | 3.72 | 27.14 | 2.84 | 12.98 | 7.91 | 3.08 | 2.64 |
| Fab-2930 | 4.66 | 30.1 | 11.44 | 6.26 | 9.31 | 33.08 | 3.79 | 22.17 | 13.82 | 4.87 | 4.37 |
| Fab-2931 | 3.11 | 10.27 | 4.7 | 3.49 | 3.65 | 28.13 | 2.89 | 9.14 | 7.43 | 2.76 | 2.59 |
| Fab-2932 | 3.59 | 16.55 | 9.39 | 3.85 | 4.26 | 29.43 | 3.11 | 34.29 | 28.90 | 3.62 | 3.82 |
| Fab-2933 | 3.92 | 14.46 | 9.82 | 4.1 | 46.35 | 34.91 | 4.10 | 8.74 | 26.66 | 143.30 | 21.10 |
| Fab-2934 | 3.13 | 61.53 | 6.61 | 3.28 | 4.78 | 34.29 | 2.86 | 3.52 | 29.43 | 2.71 | 2.67 |
| Fab-2935 | 3.46 | 4.07 | 6.79 | 4.49 | 7.3 | 29.16 | 3.37 | 3.00 | 15.82 | 3.52 | 3.34 |
| Fab-2936 | 2.81 | 3.05 | 3.52 | 3 | 3.65 | 23.50 | 2.57 | 2.55 | 7.04 | 2.74 | 2.50 |

Binding was measured via flow cytometry analysis of CHO cells overexpressing CRD of FZD1, FZD2, FZD3, FZD4, FZD5, FZD6, FZD7, FZD8, FZD9 or FZD10. Median fluorescence values are shown. Values indicating binding of Fab to Frizzled CRD (median fluorescence values >2-fold that of CHO cells not expressing Frizzled CRD) indicated in larger/bold/underlined font.

TABLE 11

Immunofluorescence analysis of binding of anti-FZD5 Fabs to cell-surface expressed Frizzled family member CRDs.

| | | | | Frizzled CRD overexpressed on CHO cells | | | | | |
|---|---|---|---|---|---|---|---|---|---|
| Fab ID | FZD1 | FZD2 | FZD3 | FZD4 | FZD5 | FZD6 | FZD7 | FZD8 | FZD9 | FZD10 |
| Fab-2898 | ++++ | +++ | – | – | +++ | – | +++ | + | – | – |
| Fab-2899 | +++ | +++ | – | – | +++ | – | +++ | + | – | – |
| Fab-2900 | – | – | – | – | ++++ | – | + | + | – | – |
| Fab-2901 | | – | – | – | ++++ | – | + | + | – | – |
| Fab-2902 | – | – | – | – | ++++ | – | + | ++ | – | – |
| Fab-2903 | + | – | – | – | ++++ | – | ++ | + | – | – |
| Fab-2904 | +++ | +++ | – | – | ++++ | – | ++++ | + | – | – |
| Fab-2905 | | – | – | – | + | – | + | – | – | – |
| Fab-2906 | – | – | – | – | ++++ | – | + | + | – | +++ |
| Fab-2907 | – | – | – | – | ++++ | – | + | + | – | – |
| Fab-2908 | – | | – | – | ++++ | – | ++ | – | – | – |
| Fab-2909 | – | – | – | – | +++ | – | + | – | – | – |
| Fab-2910 | – | – | – | – | ++++ | – | + | – | – | – |
| Fab-2911 | ++ | +++ | – | – | ++ | – | +++ | – | – | – |
| Fab-2912 | + | +++ | – | ++ | +++ | – | ++++ | + | – | – |
| Fab-2913 | ++ | +++ | – | – | ++ | – | ++++ | – | – | – |
| Fab-2914 | ++ | +++ | – | – | ++++ | – | ++++ | ++ | – | – |
| Fab-2915 | ++ | +++ | – | – | +++ | | ++++ | + | – | – |
| Fab-2916 | ++++ | ++++ | – | – | ++++ | – | ++++ | + | – | – |
| Fab-2917 | – | – | – | – | ++++ | – | ++ | + | – | – |

TABLE 11-continued

Immunofluorescence analysis of binding of anti-FZD5 Fabs to cell-surface expressed Frizzled family member CRDs.

| | Frizzled CRD overexpressed on CHO cells | | | | | | | | | |
| Fab ID | FZD1 | FZD2 | FZD3 | FZD4 | FZD5 | FZD6 | FZD7 | FZD8 | FZD9 | FZD10 |
| --- | --- | --- | --- | --- | --- | --- | --- | --- | --- | --- |
| Fab-2918 | – | – | – | – | ++++ | – | + | + | – | – |
| Fab-2919 | – | – | – | – | ++++ | – | – | ++ | – | – |
| Fab-2920 | – | – | – | – | ++++ | – | – | + | – | – |
| Fab-2921 | – | – | – | – | ++++ | – | – | + | – | – |
| Fab-2922 | – | – | – | – | ++++ | – | – | + | – | – |
| Fab-2923 | – | – | – | – | ++++ | – | – | + | – | – |
| Fab-2924 | – | – | – | – | ++++ | – | – | + | – | – |
| Fab-2925 | ++ | | – | – | ++++ | – | ++ | – | – | – |
| Fab-2926 | – | – | – | – | ++++ | – | – | + | – | – |
| Fab-2927 | +++ | +++ | – | – | ++++ | – | ++++ | + | – | – |
| Fab-2928 | – | – | – | – | ++++ | – | – | – | – | – |
| Fab-2929 | – | – | – | – | ++++ | – | + | – | – | – |
| Fab-2930 | – | – | – | – | ++++ | – | + | + | – | – |
| Fab-2931 | – | + | – | – | ++++ | – | + | – | – | – |
| Fab-2932 | – | – | – | – | ++++ | – | ++ | + | – | – |
| Fab-2933 | + | – | – | +++ | ++++ | – | + | + | – | – |
| Fab-2934 | – | – | – | – | ++++ | – | – | + | – | – |
| Fab-2935 | – | – | – | – | ++++ | – | – | + | – | – |
| Fab-2936 | – | – | – | – | ++++ | – | – | + | – | – |

Binding was measured via immunofluorescence analysis of CHO cells overexpressing CRD of FZD1, FZD2, FZD3, FZD4, FZD5, FZD6, FZD7, FZD8, FZD9 or FZD10. Legend: –, no binding; +, very weak binder; ++, weak binder; +++, good binder; ++++, very good binder.

To further characterize these Frizzled CRD binders, IgG molecules IgG-2910, IgG-2916, IgG-2919, IgG-2920, IgG-2921 and IgG-2929 incorporating antibody variable region Fv-2910, Fv-2916, Fv-2919, Fv-2920, Fv-2921 and Fv-2929, respectively, were produced and their binding to the CRD of FZD1, FZD2, FZD5, FZD7 and FZD8 was analyzed using surface plasmon resonance (SPR). As shown in Table 12, IgG-2910, IgG-2919, IgG-2920, IgG-2921 and IgG-2929 show sub-nanomolar affinity ($K_D$) to both FZD5 and FZD8. IgG-2916 was found to bind to all five Frizzled family members tested with single-digit nanomolar or better affinity.

Example 6: Anti-FZD5 Antibodies IgG-2910, IgG-2916, IgG-2919, IgG-2920, IgG-2921 and IgG-2929 Suppress Proliferation of Multiple Pancreatic Cancer Cell Lines with Inactivating Mutations in the Wnt Pathway Negative Regulator RNF43

Anti-FZD5 antibodies IgG-2910, IgG-2916, IgG-2919, IgG-2920, IgG-2921 and IgG-2929 were tested for their effect on proliferation of RNF43-mutant versus RNF43-wild type pancreatic cancer cells. All IgGs tested were found to suppress, to varying degrees, the proliferation of RNF43-

TABLE 12

Surface plasmon resonance analysis of binding of IgG-2910, IgG-2916, IgG-2919, IgG-2920, IgG-2921 and IgG-2929 to CRD of FZD1, FZD2, FZD5, FZD7 and FZD8.

| Binding target | Binding parameter | IgG ID | | | | | |
| | | IgG-2910 | IgG-2916 | IgG-2919 | IgG-2920 | IgG-2921 | IgG-2929 |
| --- | --- | --- | --- | --- | --- | --- | --- |
| FZD1-Fc | $K_a$ (1/Ms) | — | 3.64E+05 | — | — | — | — |
| | $K_a$ (1/s) | — | 4.51E−04 | — | — | — | — |
| | $K_D$ (M) | — | 1.24E−09 | — | — | — | — |
| FZD2-Fc | $K_a$ (1/Ms) | — | 5.00E+05 | — | — | — | — |
| | $K_a$ (1/s) | — | 4.52E−04 | — | — | — | — |
| | $K_D$ (M) | — | 9.05E−10 | — | — | — | — |
| FZD5-Fc | $K_a$ (1/Ms) | 1.52E+06 | 1.32E+06 | 4.16E+05 | 3.59E+06 | 9.22E+05 | 2.77E+06 |
| | $K_a$ (1/s) | 1.74E−04 | 1.30E−05 | 8.06E−05 | 3.17E−04 | 9.81E−05 | 2.77E+06 |
| | $K_D$ (M) | 1.15E−10 | 9.88E−12 | 1.94E−10 | 8.83E−11 | 1.06E−10 | 2.77E+06 |
| FZD7-Fc | $K_a$ (1/Ms) | — | 7.70E+05 | — | — | — | — |
| | $K_a$ (1/s) | — | 3.82E−04 | — | — | — | — |
| | $K_D$ (M) | — | 4.96E−10 | — | — | — | — |
| FZD8-Fc | $K_a$ (1/Ms) | 5.33E+05 | 1.04E+06 | 5.33E+05 | 4.25E+06 | 1.11E+06 | 3.27E+06 |
| | $K_a$ (1/s) | 2.28E−05 | 4.75E−05 | 2.28E−05 | 2.38E−04 | 2.71E−05 | 3.27E+06 |
| | $K_D$ (M) | 4.27E−11 | 4.55E−11 | 4.27E−11 | 5.60E−11 | 2.44E−11 | 3.27E+06 |

Figure 9A:
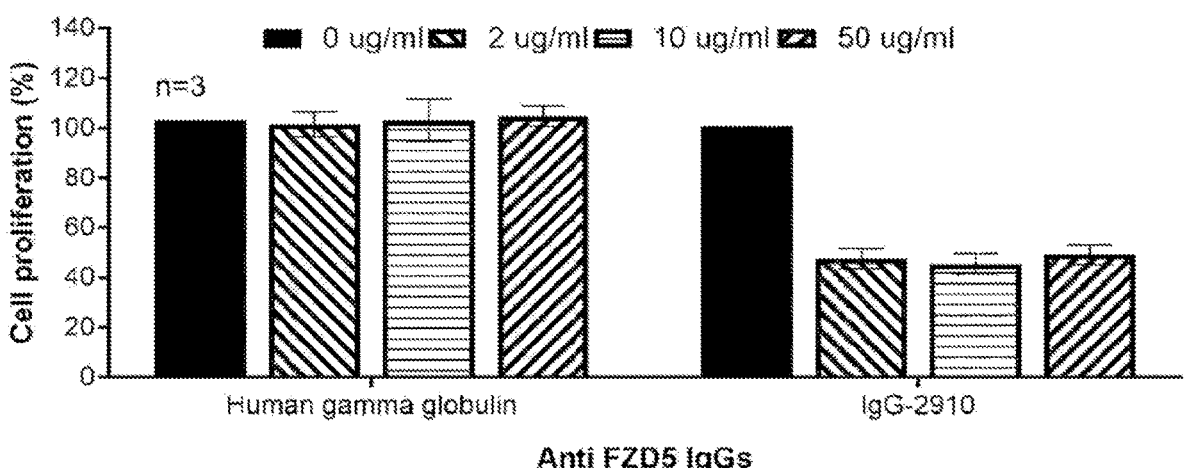
FIG. 9A is a histogram depicting the effect of treatment with IgG-2910 on proliferation of pancreatic cancer cell line ASPC-1.
Figure 9B:
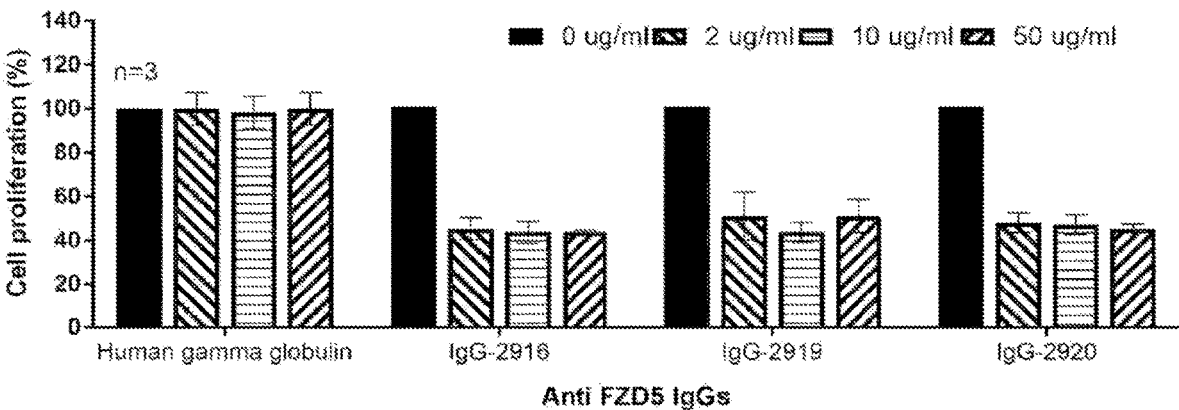
FIG. 9B is a histogram depicting the effect of treatment with IgG-2916, IgG-2919 or IgG-2920 on proliferation of pancreatic cancer cell line ASPC-1.
Figure 9C:
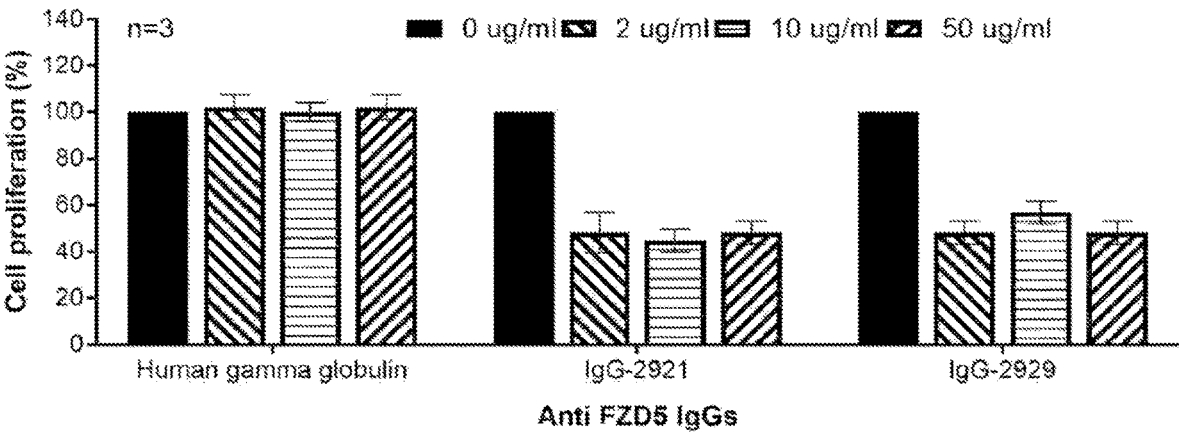
FIG. 9C is a histogram depicting the effect of treatment with IgG-2921 or IgG-2929 on proliferation of pancreatic cancer cell line ASPC-1.
Figure 9D:
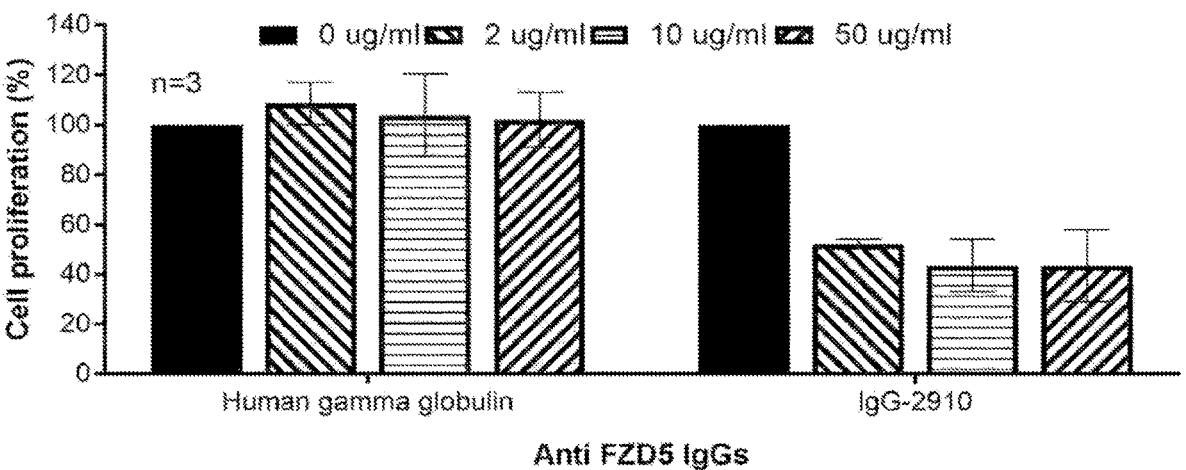
FIG. 9D is a histogram depicting the effect of treatment with IgG-2910 on proliferation of pancreatic cancer cell line HPAFII.
Figure 9E:
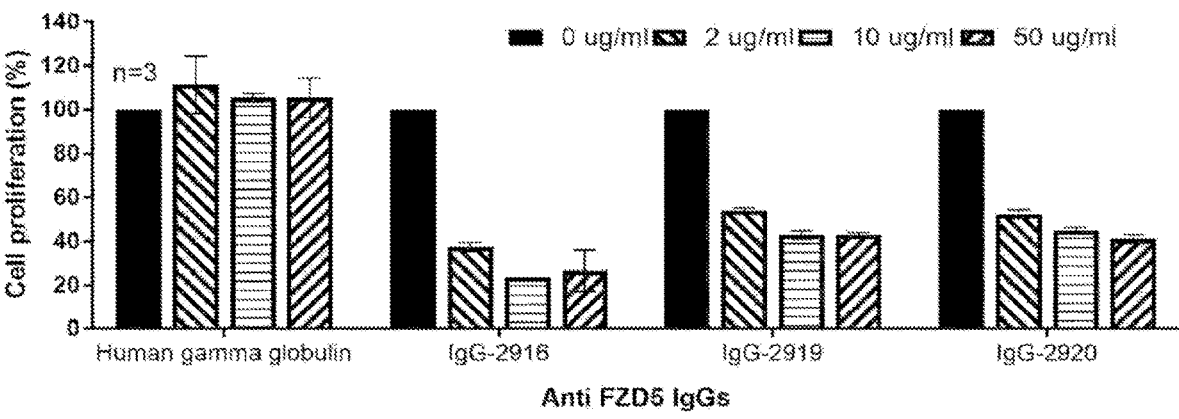
FIG. 9E is a histogram depicting the effect of treatment with IgG-2916, IgG-2919 or IgG-2920 on proliferation of pancreatic cancer cell line HPAFII.
Figure 9F:
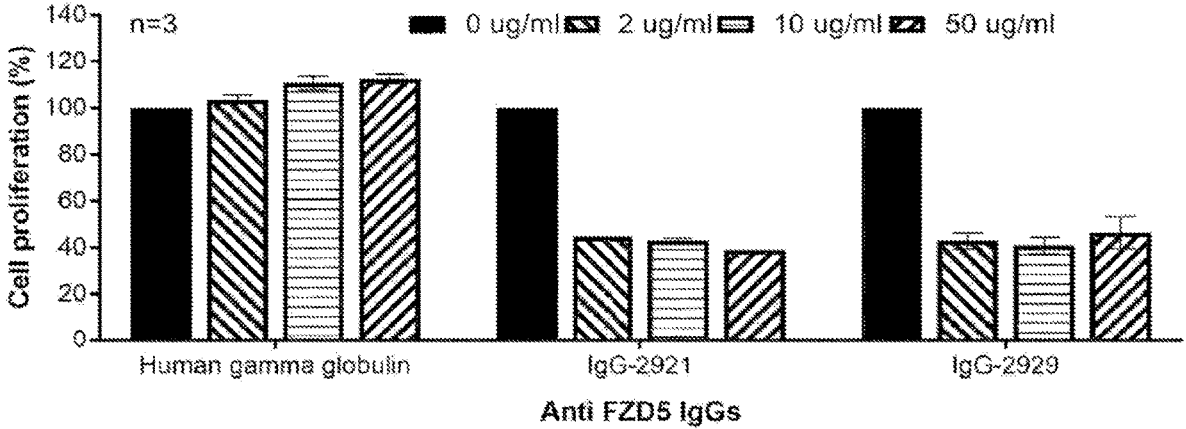
FIG. 9F is a histogram depicting the effect of treatment with IgG-2921 or IgG-2929 on proliferation of pancreatic cancer cell line HPAFII.
Figure 9G:
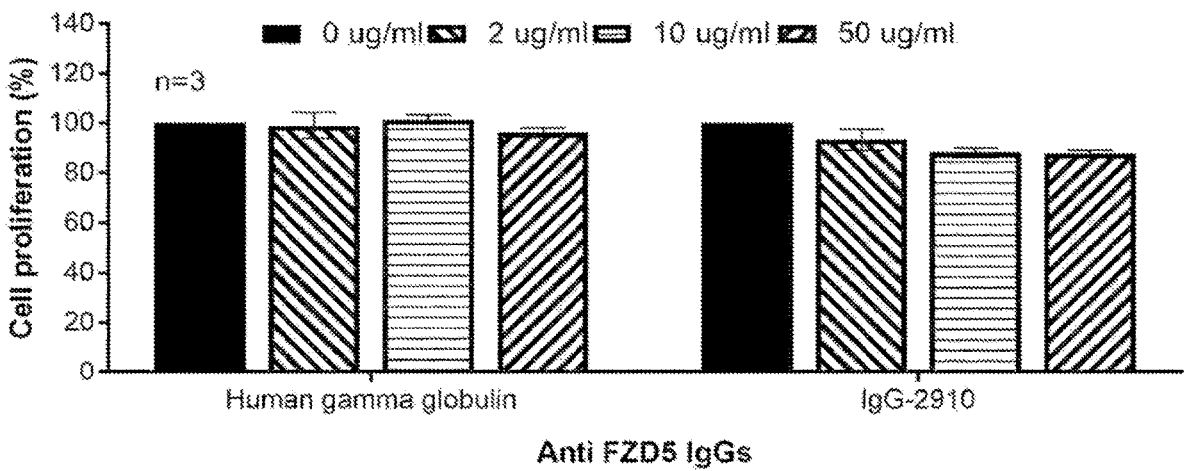
FIG. 9G is a histogram depicting the effect of treatment with IgG-2910 on proliferation of pancreatic cancer cell line CAPAN 2.
Figure 9H:
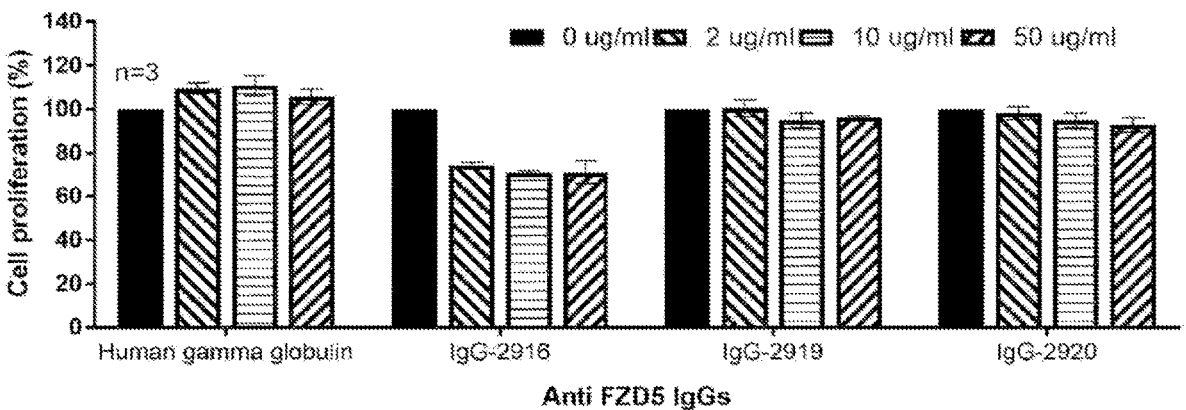
FIG. 9H is a histogram depicting the effect of treatment with IgG-2916, IgG-2919 or IgG-2920 on proliferation of pancreatic cancer cell line CAPAN 2.
Figure 9I:
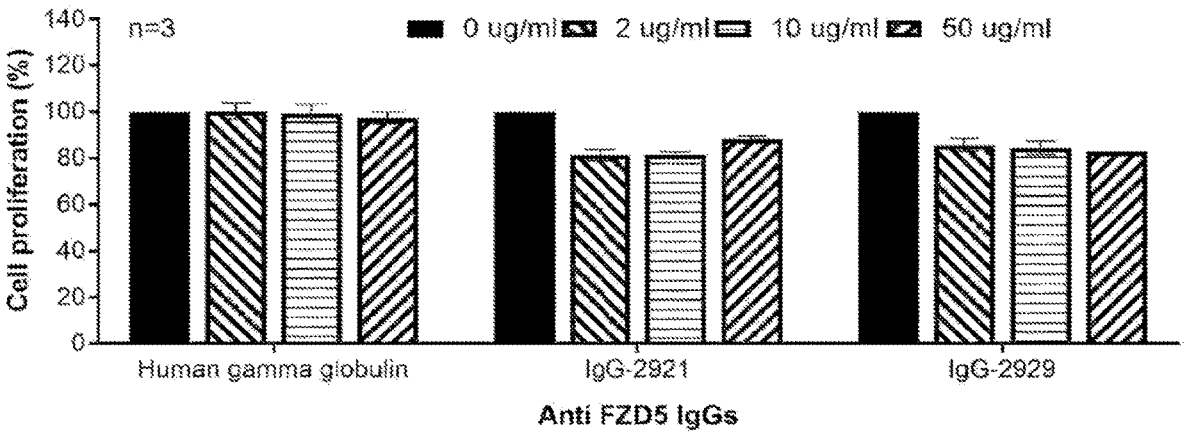
FIG. 9I is a histogram depicting the effect of treatment with IgG-2921 or IgG-2929 on proliferation of pancreatic cancer cell line CAPAN 2.
Figure 9J:
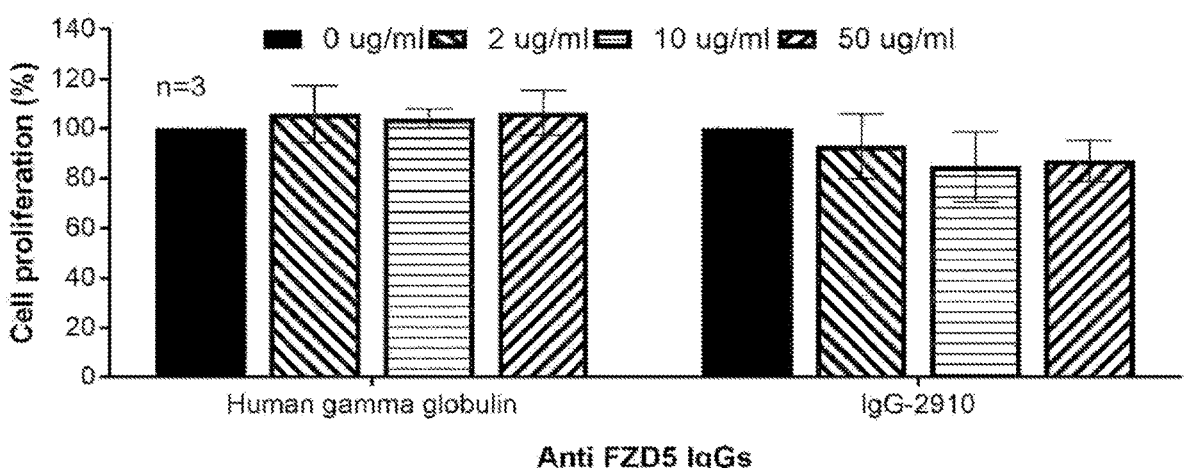
FIG. 9J is a histogram depicting the effect of treatment with IgG-2910 on proliferation of pancreatic cancer cell line IMIMPC2.
Figure 9K:
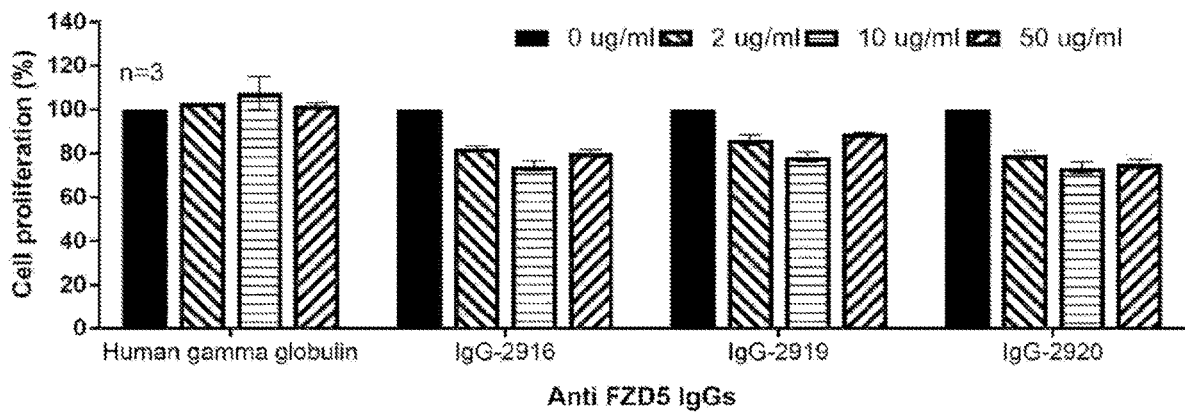
FIG. 9K is a histogram depicting the effect of treatment with IgG-2916, IgG-2919 or IgG-2920 on proliferation of pancreatic cancer cell line IMIMPC2.
Figure 9L:
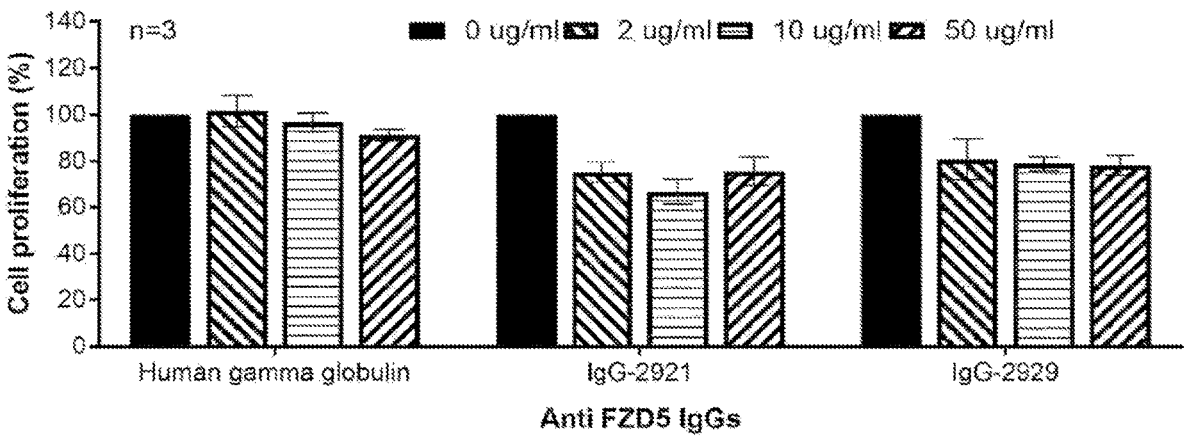
FIG. 9L is a histogram depicting the effect of treatment with IgG-2921 or IgG-2929 on proliferation of pancreatic cancer cell line IMIMPC2.
Figure 9M:
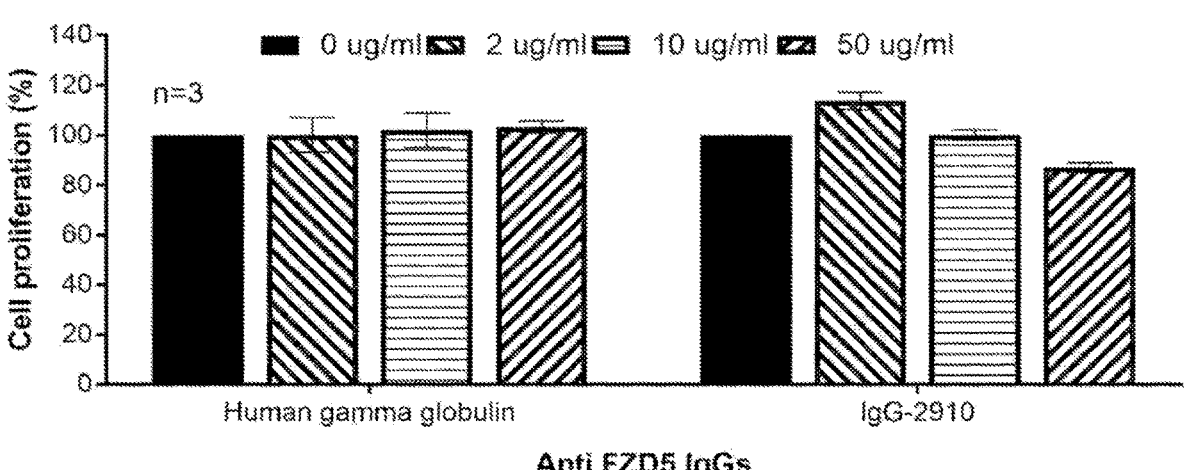
FIG. 9M is a histogram depicting the effect of treatment with IgG-2910 on proliferation of pancreatic cancer cell line PATU8988S.
Figure 9N:
FIG. 9N is a histogram depicting the effect of treatment with IgG-2916, IgG-2919 or IgG-2920 on proliferation of pancreatic cancer cell line PATU8988S.
Figure 9O:
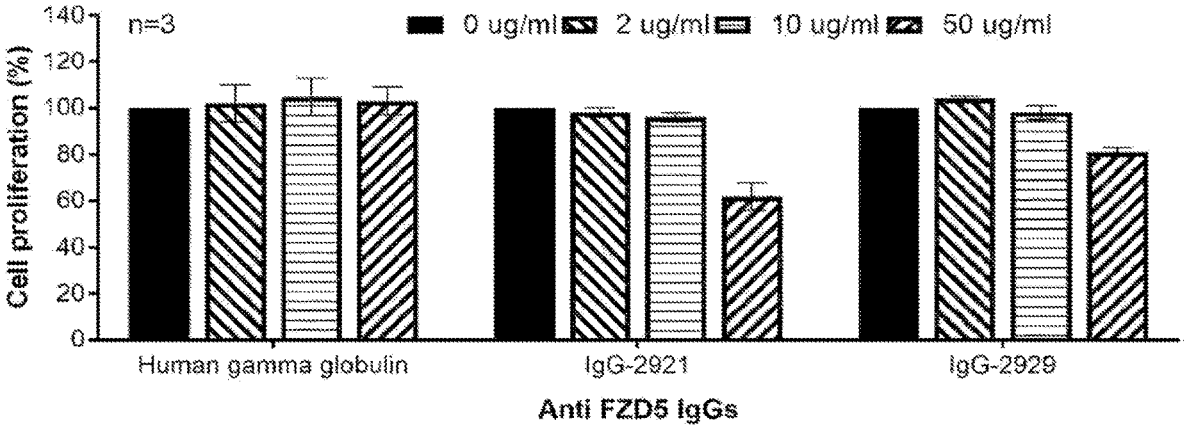
FIG. 9O is a histogram depicting the effect of treatment with IgG-2921 or IgG-2929 on proliferation of pancreatic cancer cell line PATU8988S.
Figure 9P:
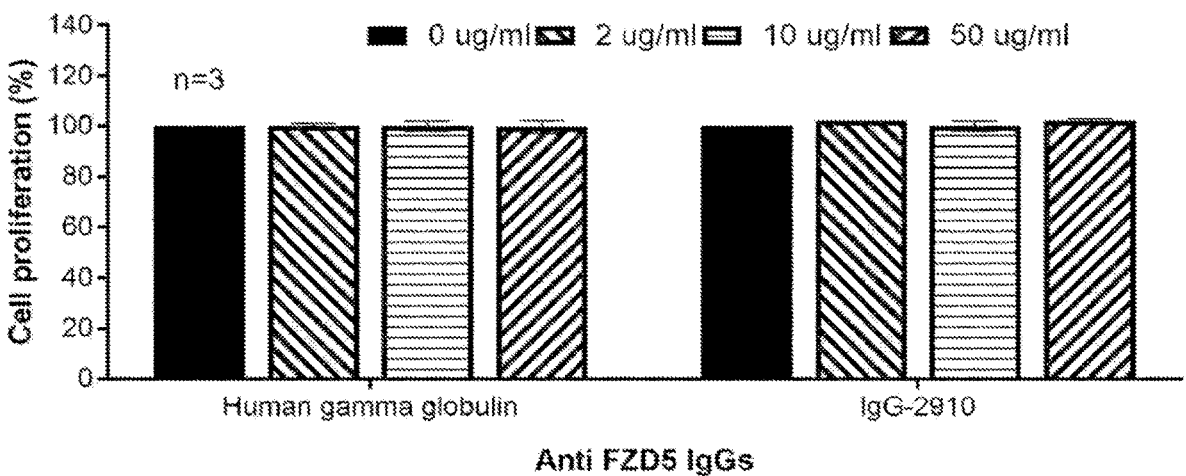
FIG. 9P is a histogram depicting the effect of treatment with IgG-2910 on proliferation of pancreatic cancer cell line BXPC3.
Figure 9Q:
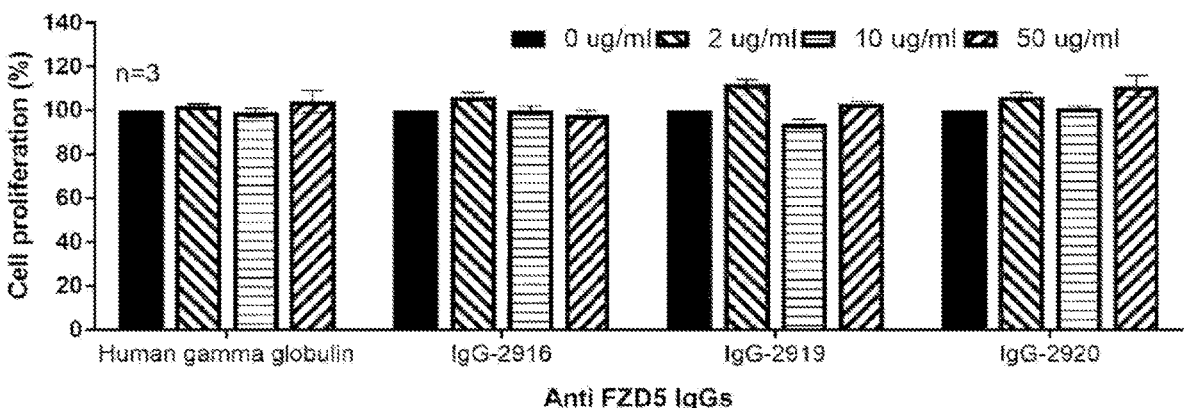
FIG. 9Q is a histogram depicting the effect of treatment with IgG-2916, IgG-2919 or IgG-2920 on proliferation of pancreatic cancer cell line BXPC3.
Figure 9R:
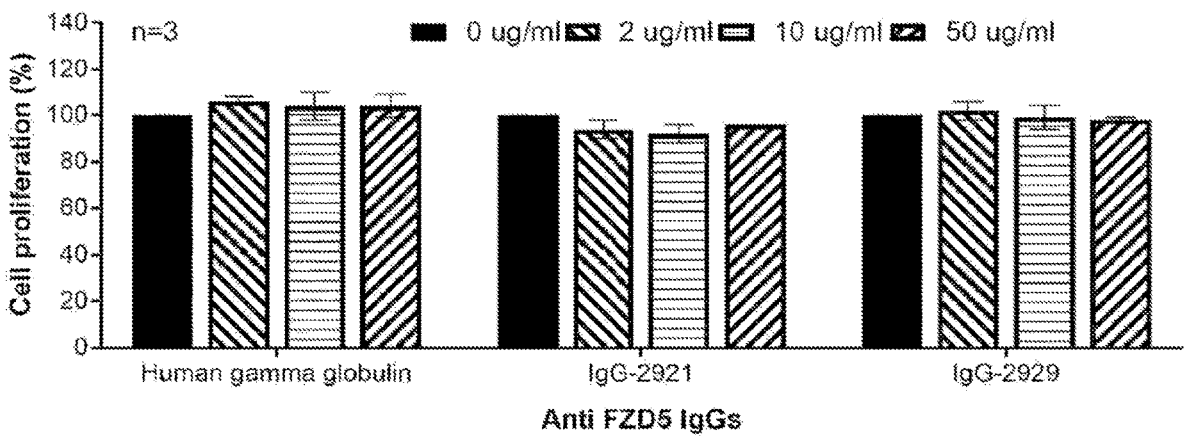
FIG. 9R is a histogram depicting the effect of treatment with IgG-2921 or IgG-2929 on proliferation of pancreatic cancer cell line BXPC3.

Analysis was performed using Frizzled-Fc chimera binding targets, in which the Frizzled segment consists of an extracellular portion of Frizzled which includes the CRD. Legend: $K_a$, association constant; $K_d$, dissociation constant; $K_D$, equilibrium dissociation constant.

mutant pancreatic cancer cell lines AsPC-1 (FIG. 9A, FIG. 9B, FIG. 9C), HPAFII (FIG. 9D, FIG. 9E, FIG. 9F), CAPAN 2 (FIG. 9G, FIG. 9H, FIG. 9I), IMIMPC2 (FIG. 9J, FIG. 9K, FIG. 9L), and PATU8988s (FIG. 9M, FIG. 9N, FIG. 9O). No effect was seen with RNF43-wild type BxPC3 (FIG. 9P, FIG. 9Q, FIG. 9R) and other cell lines (not shown), including Hs766T, PATU8988T, and IMIMPC1. Treatment of cell lines HPAF-II, AsPC-1 and PaTu8988S with IgG-2919 or IgG-2921 resulted in dose-dependent growth inhibition (FIG. 10A, FIG. 10B and FIG. 10C, respectively), but not of the RNF43-wild type cell lines PANC-1 and BxPC-3 (FIG. 10D and FIG. 10E, respectively). In addition, anti-FZD5 IgG treatment led to inhibition of AXIN2 and NKD1 mRNA when compared to control IgG, demonstrating specific Wnt-beta-catenin pathway inhibition (FIG. 10F). The effects of IgG-2919 and IgG-2921 were also tested in three patient-derived PDAC cell lines and significant anti-proliferative efficacy was observed in GP2A cells, which harbor an RNF43 mutation (R117H), but not in GP3A or GP7B (RNF43-wild type) cells (FIG. 10G). Therefore, the cancer cell lines that were sensitive to the anti-FZD5 antibodies all have inactivating mutations in the Wnt pathway negative regulator RNF43, whereas none of the RNF43-wild type pancreatic cancer cells displayed such sensitivity (summarized in Table 13).

TABLE 13

Sensitivity to FZD5 IgGs and RNF43 mutation status in cancer cells.

| Pancreatic cancer line | Sensitivity to FZD5 mAbs | RNF43 mutation |
|---|---|---|
| HPAFII | yes | yes |
| ASPC1 | yes | yes |

TABLE 13-continued

Sensitivity to FZD5 IgGs and RNF43 mutation status in cancer cells.

| Pancreatic cancer line | Sensitivity to FZD5 mAbs | RNF43 mutation |
|---|---|---|
| PATU8988S | yes | yes |
| CAPAN2 | yes | yes |
| IMIMPC2 | yes | yes |
| GP2A | yes | yes |
| BXPC3 | no | no |
| PANC-1 | no | no |
| GP3A | no | no |
| GP7B | no | no |

Example 7: Presently Disclosed Fabs Suppress Proliferation of Multiple Pancreatic Cancer Cell Lines with Inactivating Mutations in the Wnt Pathway Negative Regulator RNF43

The effect of presently disclosed anti-FZD5 Fabs on proliferation of RNF43 loss-of-function mutant pancreatic cancer cell lines HPAFII, PATU8988S and ASPC-1; and on pancreatic cancer cell line RWP1, was tested at 2 μg/ml and 10 μg/ml. As shown in Table 14, various anti-FZD5 Fabs exhibit a capacity to inhibit proliferation of multiple types of pancreatic cancer cell lines.

TABLE 14

Effect of anti-FZD5 Fabs at concentrations of 2 μg/ml and 10 μg/ml on proliferation of RNF43 loss-of-function pancreatic cancer cell lines HPAFII, PATU8988S and ASPC-1; and pancreatic cancer cell line RWP1. Values represent percent growth inhibition.

| Fab ID | HPAFII | | PATU8988s | | ASPC-1 | | RWP1 | |
|---|---|---|---|---|---|---|---|---|
| | 2 μg/ml | 10 μg/ml | 2 μg/ml | 10 μg/ml | 2 μg/ml | 10 μg/ml | 2 μg/ml | 10 μg/ml |
| Fab-2898 | 15.80 | 21.87 | 4.53 | 0.97 | 11.14 | 25.15 | 21.46 | 26.93 |
| Fab-2899 | 36.18 | 55.71 | 4.94 | −3.10 | 37.97 | 33.63 | 37.95 | 47.83 |
| Fab-2900 | 3.34 | 3.46 | −29.28 | −51.41 | −13.30 | −1.26 | −28.30 | −29.81 |
| Fab-2901 | 6.38 | 12.31 | −9.37 | −6.65 | −8.27 | 11.26 | −19.95 | 21.10 |
| Fab-2902 | 25.42 | 21.81 | −15.75 | −32.61 | 10.84 | 17.39 | 26.56 | 31.22 |
| Fab-2903 | −10.34 | −10.98 | −22.81 | −16.37 | 4.49 | 14.86 | 8.52 | 17.38 |
| Fab-2904 | 2.11 | 7.46 | −10.42 | −41.59 | 19.26 | 28.59 | 13.33 | 5.44 |
| Fab-2905 | 0.41 | −12.83 | −26.66 | −46.23 | −14.51 | −10.34 | 62.88 | 41.10 |
| Fab-2906 | 15.24 | 14.98 | −17.42 | −30.04 | 20.56 | 35.20 | 1.19 | 5.47 |
| Fab-2907 | 15.15 | 14.20 | −12.76 | −42.69 | 10.02 | 23.78 | 8.52 | 28.57 |
| Fab-2908 | 1.13 | −6.58 | −7.07 | −29.21 | −1.54 | −0.56 | 14.26 | 17.76 |
| Fab-2909 | 2.87 | −2.57 | −9.95 | −16.04 | −6.84 | −9.30 | 12.89 | 14.89 |
| Fab-2910 | 26.86 | 41.81 | 8.48 | −12.84 | 39.05 | 41.71 | 71.49 | 54.51 |
| Fab-2911 | 2.08 | na | 8.24 | na | 3.18 | na | 20.34 | na |
| Fab-2912 | 7.76 | −5.41 | 1.11 | −25.71 | 6.93 | 1.76 | 15.55 | 27.25 |
| Fab-2913 | −5.59 | −28.52 | −15.09 | −43.04 | 2.25 | −7.73 | 59.79 | 68.29 |
| Fab-2914 | −4.97 | 6.47 | −15.14 | −26.59 | 16.76 | 38.30 | 68.03 | 78.98 |
| Fab-2915 | −16.37 | −31.87 | −6.43 | −19.02 | 5.51 | 4.18 | 48.66 | 45.04 |
| Fab-2916 | 31.28 | 52.29 | −25.67 | −19.08 | 44.03 | 42.26 | 1.68 | 30.61 |
| Fab-2917 | 26.55 | 38.26 | −24.25 | −43.54 | 46.10 | 42.32 | 28.91 | 54.68 |
| Fab-2918 | 37.15 | 44.60 | −0.86 | −1.92 | 44.67 | 45.56 | 3.49 | 39.24 |
| Fab-2919 | 16.25 | 36.80 | −7.74 | −11.49 | 30.04 | 35.99 | 7.36 | 22.54 |
| Fab-2920 | 29.48 | 32.93 | 6.20 | −5.60 | 33.66 | 40.69 | −16.26 | −3.09 |
| Fab-2921 | 30.70 | 44.23 | −1.56 | −16.29 | 43.20 | 47.95 | −4.47 | −0.10 |
| Fab-2922 | 8.28 | 8.14 | 9.16 | −24.14 | 14.47 | 27.72 | −6.96 | 7.59 |
| Fab-2923 | 15.14 | 18.17 | −18.54 | −19.05 | 35.27 | 34.00 | 35.90 | 40.29 |
| Fab-2924 | −10.43 | −5.35 | −16.11 | −21.08 | 8.55 | 16.29 | 42.76 | 48.95 |
| Fab-2925 | −11.24 | −17.38 | −8.12 | −22.86 | −0.26 | −3.44 | 30.69 | 33.53 |
| Fab-2926 | −6.88 | 4.88 | −15.89 | −36.54 | 17.27 | 24.71 | 37.95 | 40.20 |
| Fab-2927 | 6.46 | −7.63 | −15.15 | −23.95 | 12.47 | 31.00 | 46.02 | 70.38 |
| Fab-2928 | −17.90 | −25.51 | −2.11 | −30.22 | 2.33 | 6.27 | −8.19 | 32.47 |

TABLE 14-continued

Effect of anti-FZD5 Fabs at concentrations of 2 µg/ml and 10 µg/ml on proliferation
of RNF43 loss-of-function pancreatic cancer cell lines HPAFII, PATU8988S and ASPC-1; and
pancreatic cancer cell line RWP1. Values represent percent growth inhibition.

| Fab | HPAFII | | PATU8988s | | ASPC-1 | | RWP1 | |
|---|---|---|---|---|---|---|---|---|
| ID | 2 µg/ml | 10 µg/ml | 2 µg/ml | 10 µg/ml | 2 µg/ml | 10 µg/ml | 2 µg/ml | 10 µg/ml |
| Fab-2929 | 20.20 | 33.42 | −24.05 | −27.58 | 41.68 | 41.25 | 0.41 | 2.21 |
| Fab-2930 | −10.77 | 7.81 | −0.39 | −13.64 | 21.31 | 37.33 | 17.91 | 10.72 |
| Fab-2931 | −19.38 | 11.37 | −20.00 | −17.27 | 10.33 | 39.20 | 15.35 | 18.70 |
| Fab-2932 | −0.17 | 3.21 | −14.70 | −8.85 | 28.71 | 28.62 | 32.22 | 25.69 |
| Fab-2933 | −14.19 | −6.12 | 6.02 | −17.17 | −1.03 | 19.44 | −21.16 | 27.16 |
| Fab-2934 | 3.40 | 20.44 | −9.14 | 1.78 | 26.80 | 36.76 | 7.90 | 0.90 |
| Fab-2935 | −9.18 | −10.62 | 2.48 | −22.12 | 4.75 | 24.63 | −14.51 | 10.15 |
| Fab-2936 | −0.56 | 12.21 | −8.03 | −23.52 | 17.01 | 22.02 | 0.02 | −5.97 |

Example 8: Dose-Dependent Suppression of In
Vivo Tumor Growth by Anti-FZD5 Antibody
IgG-2919

The efficiency of IgG-2919 to inhibit tumor growth was evaluated in a subcutaneous xenograft mouse model using HPAF-II cells and showed that twice-weekly dosing at 1 mg/kg or 2 mg/kg led to 46% or 73% tumor growth inhibition, respectively (FIG. 11, FIG. 12A and FIG. 12B), with no signs of toxicity (FIG. 12C). In addition, histological analysis of the tumors revealed increased mucin production as visualized by Alcian Blue staining, consistent with cellular differentiation (Jiang et al., 2013).

Incorporation of Sequence Listing

A computer readable form of the Sequence Listing "ModMab_17176155_Sequence_Listing.txt" (92,617 bytes), submitted via EFS-WEB and created on Feb. 25, 2021, is herein incorporated by reference. The Sequence Listing contains no new matter. The ASCII text file copy and the PDF copy of the Sequence Listing are identical.

What is claimed is:

1. A method of screening for compounds that inhibit proliferation of pancreatic cancer cells having a loss-of-function mutation in the RNF43 gene by inhibition of the binding between FZD5 and Wnt7B, the method comprising:

measuring binding between FZD5 and Wnt7B in said pancreatic cancer cells;

exposing FZD5 and Wnt7B to a test agent; and determining if the test agent inhibits binding between FZD5 and Wnt7B, wherein inhibition of said binding identifies the test agent as a compound that inhibits proliferation of said pancreatic cancer cells.

2. The method of claim 1 further comprising that the test agent inhibits binding between FZD5 and Wnt7B by at least 5%.

3. The method of claim 1 further comprising that the test agent inhibits binding between FZD5 and Wnt7B by at least 10%.

4. The method of claim 1 further comprising that the test agent inhibits binding between FZD5 and Wnt7B by at least 25%.

5. The method of claim 1 further comprising that the test agent inhibits binding between FZD5 and Wnt7B by at least 75%.

* * * * *

SEQUENCE LISTING

<160> NUMBER OF SEQ ID NOS: 377

<210> SEQ ID NO 1
<211> LENGTH: 58
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (20)..(39)
<223> OTHER INFORMATION: n is a, c, g, or t

<400> SEQUENCE: 1
agagaacctg cagagaccgn nnnnnnnnnn nnnnnnnnng tttagaggca ggtagaga          58

<210> SEQ ID NO 2
<211> LENGTH: 40
<212> TYPE: DNA
<213> ORGANISM: Artificial Sequence
<220> FEATURE:
<223> OTHER INFORMATION: Synthetic construct

<400> SEQUENCE: 2
tgtcagttgt cattcgcgaa aaagagaacc tgcagagacc          40

<210> SEQ ID NO 3
<211> LENGTH: 40
<212> TYPE: DNA
<213> ORGANISM: Artificial Sequence
<220> FEATURE:
<223> OTHER INFORMATION: Synthetic construct

<400> SEQUENCE: 3
gtcactgacg cggttttgta gatctctacc tgcctctaaa          40

```
<210> SEQ ID NO 4
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(24)
<223> OTHER INFORMATION: n is a, c, g, or t

<400> SEQUENCE: 4
accgnnnnnn nnnnnnnnnn nnnn                                                  24

<210> SEQ ID NO 5
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(20)
<223> OTHER INFORMATION: n is a, c, g, or t

<400> SEQUENCE: 5
nnnnnnnnnn nnnnnnnnnn caaa                                                  24

<210> SEQ ID NO 6
<211> LENGTH: 20
<212> TYPE: DNA
<213> ORGANISM: Escherichia coli

<400> SEQUENCE: 6
cccgaatctc tatcgtgcgg                                                       20

<210> SEQ ID NO 7
<211> LENGTH: 20
<212> TYPE: DNA
<213> ORGANISM: Homo sapiens

<400> SEQUENCE: 7
gaaaagcggc tgttagtcac                                                       20

<210> SEQ ID NO 8
<211> LENGTH: 20
<212> TYPE: DNA
<213> ORGANISM: Homo sapiens

<400> SEQUENCE: 8
agctcgtgcc caaccaggtt                                                       20

<210> SEQ ID NO 9
<211> LENGTH: 20
<212> TYPE: DNA
<213> ORGANISM: Homo sapiens

<400> SEQUENCE: 9
atgccgccgc atgggccaat                                                       20

<210> SEQ ID NO 10
<211> LENGTH: 20
<212> TYPE: DNA
<213> ORGANISM: Homo sapiens

<400> SEQUENCE: 10
```

-continued aggccaccac aatgctggcg                                                    20

<210> SEQ ID NO 11
<211> LENGTH: 20
<212> TYPE: DNA
<213> ORGANISM: Homo sapiens

<400> SEQUENCE: 11
tccgcacctt gttgtagagc                                                    20

<210> SEQ ID NO 12
<211> LENGTH: 20
<212> TYPE: DNA
<213> ORGANISM: Homo sapiens

<400> SEQUENCE: 12
gccggggcgc agccgtacca                                                    20

<210> SEQ ID NO 13
<211> LENGTH: 20
<212> TYPE: DNA
<213> ORGANISM: Homo sapiens

<400> SEQUENCE: 13
tggtacggct gcgccccggc                                                    20

<210> SEQ ID NO 14
<211> LENGTH: 20
<212> TYPE: DNA
<213> ORGANISM: Homo sapiens

<400> SEQUENCE: 14
tagccgatgc ccttacacag                                                    20

<210> SEQ ID NO 15
<211> LENGTH: 20
<212> TYPE: DNA
<213> ORGANISM: Homo sapiens

<400> SEQUENCE: 15
caaccacgac acgcaagacg                                                    20

<210> SEQ ID NO 16
<211> LENGTH: 20
<212> TYPE: DNA
<213> ORGANISM: Homo sapiens

<400> SEQUENCE: 16
ggctgcgacc gcgagaagca                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
tgtctccttc gggctaggat                                                    20

<210> SEQ ID NO 18
<211> LENGTH: 21
<212> TYPE: DNA
<213> ORGANISM: Artificial Sequence
<220> FEATURE:
<223> OTHER INFORMATION: Synthetic construct

<400> SEQUENCE: 18
cgggacgtct aaaatcccac a                                                          21

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
caggttctgc tgcctcttca                                                           20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct

<400> SEQUENCE: 20
agtgttgtgc aaagagggct                                                           20

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
ttgcccgacc agatccagac                                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
tctgtctgcc cgactaccac                                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
tgaggactct catgcgtcgg                                                           20

<210> SEQ ID NO 24
<211> LENGTH: 18
<212> TYPE: DNA
<213> ORGANISM: Artificial Sequence
<220> FEATURE:
<223> OTHER INFORMATION: Synthetic construct

<400> SEQUENCE: 24
agccgtccga cgtgttct                                                             18

-continued

```
<210> SEQ ID NO 25
<211> LENGTH: 21
<212> TYPE: DNA
<213> ORGANISM: Artificial Sequence
<220> FEATURE:
<223> OTHER INFORMATION: Synthetic construct

<400> SEQUENCE: 25
tgtcttgacg cggttgtaga g                                                    21

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
tagattatcg gcagaccccc                                                      20

<210> SEQ ID NO 27
<211> LENGTH: 19
<212> TYPE: DNA
<213> ORGANISM: Artificial Sequence
<220> FEATURE:
<223> OTHER INFORMATION: Synthetic construct

<400> SEQUENCE: 27
ggagatggca caggaggaa                                                       19

<210> SEQ ID NO 28
<211> LENGTH: 19
<212> TYPE: DNA
<213> ORGANISM: Artificial Sequence
<220> FEATURE:
<223> OTHER INFORMATION: Synthetic construct

<400> SEQUENCE: 28
gcccgtagtg cttcagttt                                                       19

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
ctccccacct tgaatgaaga                                                      20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
tggctggtgc aaagacatag                                                      20

<210> SEQ ID NO 31
<211> LENGTH: 24
<212> TYPE: DNA
<213> ORGANISM: Artificial Sequence
<220> FEATURE:
<223> OTHER INFORMATION: Synthetic construct
```

```
<400> SEQUENCE: 31
tgagaagatg gagagagtga gcga                                              24

<210> SEQ ID NO 32
<211> LENGTH: 24
<212> TYPE: DNA
<213> ORGANISM: Artificial Sequence
<220> FEATURE:
<223> OTHER INFORMATION: Synthetic construct

<400> SEQUENCE: 32
ggtgaccttg ccgttgttgt caaa                                              24

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
agccgggaac ctactactcg                                                   20

<210> SEQ ID NO 34
<211> LENGTH: 21
<212> TYPE: DNA
<213> ORGANISM: Artificial Sequence
<220> FEATURE:
<223> OTHER INFORMATION: Synthetic construct

<400> SEQUENCE: 34
aagtggtcat aggcttcgtg c                                                 21

<210> SEQ ID NO 35
<211> LENGTH: 6
<212> TYPE: PRT
<213> ORGANISM: Artificial Sequence
<220> FEATURE:
<223> OTHER INFORMATION: Synthetic construct

<400> SEQUENCE: 35

Gln Ser Val Ser Ser Ala
1               5

<210> SEQ ID NO 36
<211> LENGTH: 3
<212> TYPE: PRT
<213> ORGANISM: Artificial Sequence
<220> FEATURE:
<223> OTHER INFORMATION: Synthetic construct

<400> SEQUENCE: 36

Ser Ala Ser
1

<210> SEQ ID NO 37
<211> LENGTH: 11
<212> TYPE: PRT
<213> ORGANISM: Artificial Sequence
<220> FEATURE:
<223> OTHER INFORMATION: Synthetic construct

<400> SEQUENCE: 37

Gln Gln Trp Trp Gly Tyr Tyr Ser Leu Ile Thr
1               5                   10
```

-continued

```
<210> SEQ ID NO 38
<211> LENGTH: 11
<212> TYPE: PRT
<213> ORGANISM: Artificial Sequence
<220> FEATURE:
<223> OTHER INFORMATION: Synthetic construct

<400> SEQUENCE: 38

Gln Gln Trp Tyr Ser Ser Tyr Gly Leu Ile Thr
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic construct

<400> SEQUENCE: 39

Gln Gln Trp Tyr Ser Gly Ser Ser Leu Phe Thr
1               5                   10

<210> SEQ ID NO 40
<211> LENGTH: 8
<212> TYPE: PRT
<213> ORGANISM: Artificial Sequence
<220> FEATURE:
<223> OTHER INFORMATION: Synthetic construct

<400> SEQUENCE: 40

Gln Gln Gly Gly Phe Leu Ile Thr
1               5

<210> SEQ ID NO 41
<211> LENGTH: 11
<212> TYPE: PRT
<213> ORGANISM: Artificial Sequence
<220> FEATURE:
<223> OTHER INFORMATION: Synthetic construct

<400> SEQUENCE: 41

Gln Gln Trp Tyr Ala Phe Gly Ala Leu Ile Thr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic construct

<400> SEQUENCE: 42

Gln Gln Trp Gly Gly Gly Ser Ser Leu Phe Thr
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Synthetic construct

<400> SEQUENCE: 43

Gln Gln Ser Ser Tyr Ser Leu Ile Thr
1               5
```

```
<210> SEQ ID NO 44
<211> LENGTH: 12
<212> TYPE: PRT
<213> ORGANISM: Artificial Sequence
<220> FEATURE:
<223> OTHER INFORMATION: Synthetic construct

<400> SEQUENCE: 44

Gln Gln Ser Ser Trp Tyr Tyr Gly Tyr Pro Phe Thr
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic construct

<400> SEQUENCE: 45

Gln Gln Trp Ser Trp Gly Phe Leu Ile Thr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic construct

<400> SEQUENCE: 46

Gln Gln Val Gly Tyr Trp Trp Gly Leu Ile Thr
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Synthetic construct

<400> SEQUENCE: 47

Gln Gln Ser Ser Tyr Ser Leu Ile Thr
1               5

<210> SEQ ID NO 48
<211> LENGTH: 11
<212> TYPE: PRT
<213> ORGANISM: Artificial Sequence
<220> FEATURE:
<223> OTHER INFORMATION: Synthetic construct

<400> SEQUENCE: 48

Gln Gln Ser Trp Ser Tyr His Tyr Leu Ile Thr
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic construct

<400> SEQUENCE: 49

Gln Gln Trp Tyr Gly Ser His Leu Ile Thr
1               5                   10
```

-continued

```
<210> SEQ ID NO 50
<211> LENGTH: 9
<212> TYPE: PRT
<213> ORGANISM: Artificial Sequence
<220> FEATURE:
<223> OTHER INFORMATION: Synthetic construct

<400> SEQUENCE: 50

Gln Gln Gly Pro Trp Tyr Pro Phe Thr
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic construct

<400> SEQUENCE: 51

Gln Gln Phe Tyr Phe Pro Tyr Leu Ile Thr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic construct

<400> SEQUENCE: 52

Gln Gln Trp Gly Val Ser His Tyr Leu Phe Thr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic construct

<400> SEQUENCE: 53

Gln Gln Trp Tyr Tyr Gly Ser Leu Ile Thr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic construct

<400> SEQUENCE: 54

Gln Gln Ala Tyr Tyr His Ser Leu Ile Thr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic construct

<400> SEQUENCE: 55

Gln Gln Trp Tyr His Tyr Pro Tyr Leu Ile Thr
1               5                   10

<210> SEQ ID NO 56
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 56

Gln Gln Ser Ser Tyr Ser Leu Ile Thr
1               5

<210> SEQ ID NO 57
<211> LENGTH: 10
<212> TYPE: PRT
<213> ORGANISM: Artificial Sequence
<220> FEATURE:
<223> OTHER INFORMATION: Synthetic construct

<400> SEQUENCE: 57

Gln Gln Ala Phe Gly Ala Ser Leu Phe Thr
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic construct

<400> SEQUENCE: 58

Gln Gln Trp Tyr Ser Ser Gly His Val Leu Ile Thr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic construct

<400> SEQUENCE: 59

Gln Gln Trp Phe Ala Gly Ala Leu Ile Thr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic construct

<400> SEQUENCE: 60

Gln Gln Trp Tyr Ala Gly Ser Leu Ile Thr
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic construct

<400> SEQUENCE: 61

Gln Gln Ser Phe Val Tyr Pro Tyr Leu Ile Thr
1               5                   10

<210> SEQ ID NO 62
<211> LENGTH: 11
```

```
<212> TYPE: PRT
<213> ORGANISM: Artificial Sequence
<220> FEATURE:
<223> OTHER INFORMATION: Synthetic construct

<400> SEQUENCE: 62

Gln Gln Trp Tyr Gly Tyr Ser Ala Leu Ile Thr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic construct

<400> SEQUENCE: 63

Gln Gln Trp Tyr Ser Gly His Ser Leu Ile Thr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic construct

<400> SEQUENCE: 64

Gln Gln Ala Trp Val Tyr Ala Ser Leu Phe Thr
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic construct

<400> SEQUENCE: 65

Gln Gln Trp Tyr His Gly Gly Ser Leu Phe Thr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic construct

<400> SEQUENCE: 66

Gln Gln Trp Gly Ser His Gly Tyr Leu Ile Thr
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Synthetic construct

<400> SEQUENCE: 67

Gln Gln Ala Phe Tyr Tyr Pro Ile Thr
1               5

<210> SEQ ID NO 68
<211> LENGTH: 11
<212> TYPE: PRT
```

-continued

<213> ORGANISM: Artificial Sequence
<220> FEATURE:
<223> OTHER INFORMATION: Synthetic construct

<400> SEQUENCE: 68

Gln Gln Trp Tyr Ser Ser Tyr Gly Leu Ile Thr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Syntethic construct

<400> SEQUENCE: 69

Gln Gln Trp Tyr Gly Pro Tyr Leu Ile Thr
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic construct

<400> SEQUENCE: 70

Gln Gln Ser Ser Tyr Ser Leu Ile Thr
1               5

<210> SEQ ID NO 71
<211> LENGTH: 11
<212> TYPE: PRT
<213> ORGANISM: Artificial Sequence
<220> FEATURE:
<223> OTHER INFORMATION: Synthetic construct

<400> SEQUENCE: 71

Gln Gln Trp Tyr Gly Ser Phe Ala Leu Ile Thr
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic construct

<400> SEQUENCE: 72

Gln Gln Phe Trp Trp Tyr Ala Ser Trp Leu Phe Thr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic construct

<400> SEQUENCE: 73

Gln Gln Trp Tyr His Tyr Gly Leu Ile Thr
1               5                   10

<210> SEQ ID NO 74
<211> LENGTH: 11
<212> TYPE: PRT
<213> ORGANISM: Artificial Sequence -continued

```
<220> FEATURE:
<223> OTHER INFORMATION: Synthetic construct

<400> SEQUENCE: 74

Gln Gln Trp Tyr Gly Gly Tyr Ala Leu Ile Thr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic construct

<400> SEQUENCE: 75

Gln Gln Trp Tyr Ala Ala Ser Leu Ile Thr
1               5                   10

<210> SEQ ID NO 76
<211> LENGTH: 8
<212> TYPE: PRT
<213> ORGANISM: Artificial Sequence
<220> FEATURE:
<223> OTHER INFORMATION: Synthetic construct

<400> SEQUENCE: 76

Gly Phe Asn Ile Tyr Ser Tyr Ser
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic construct

<400> SEQUENCE: 77

Gly Phe Asn Leu Tyr Tyr Tyr Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic construct

<400> SEQUENCE: 78

Gly Phe Asn Leu Ser Ser Tyr Tyr
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic construct

<400> SEQUENCE: 79

Gly Phe Asn Ile Ser Tyr Ser Tyr
1               5

<210> SEQ ID NO 80
<211> LENGTH: 8
<212> TYPE: PRT
<213> ORGANISM: Artificial Sequence
<220> FEATURE:
```

-continued

```
<223> OTHER INFORMATION: Synthetic construct

<400> SEQUENCE: 80

Gly Phe Asn Ile Ser Tyr Tyr Tyr
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic construct

<400> SEQUENCE: 81

Gly Phe Asn Leu Ser Tyr Tyr Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic construct

<400> SEQUENCE: 82

Gly Phe Asn Ile Tyr Ser Tyr Ser
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic construct

<400> SEQUENCE: 83

Gly Phe Asn Leu Ser Tyr Tyr Tyr
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic construct

<400> SEQUENCE: 84

Gly Phe Asn Phe Ser Ser Ser Ser
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic construct

<400> SEQUENCE: 85

Gly Phe Asn Ile Tyr Ser Ser Tyr
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 86

Gly Phe Asn Phe Ser Ser Ser Ser
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic construct

<400> SEQUENCE: 87

Gly Phe Asn Ile Ser Ser Ser Tyr
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic construct

<400> SEQUENCE: 88

Gly Phe Asn Ile Ser Tyr Ser Tyr
1               5

<210> SEQ ID NO 89
<211> LENGTH: 8
<212> TYPE: PRT
<213> ORGANISM: Artificial Sequence
<220> FEATURE:
<223> OTHER INFORMATION: Synthetic construct

<400> SEQUENCE: 89

Gly Phe Asn Ile Tyr Tyr Ser Ser
1               5

<210> SEQ ID NO 90
<211> LENGTH: 8
<212> TYPE: PRT
<213> ORGANISM: Artificial Sequence
<220> FEATURE:
<223> OTHER INFORMATION: Synthetic construct

<400> SEQUENCE: 90

Gly Phe Asn Ile Ser Tyr Ser Tyr
1               5

<210> SEQ ID NO 91
<211> LENGTH: 8
<212> TYPE: PRT
<213> ORGANISM: Artificial Sequence
<220> FEATURE:
<223> OTHER INFORMATION: Synthetic construct

<400> SEQUENCE: 91

Gly Phe Asn Ile Ser Tyr Ser Ser
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic construct
```

```
<400> SEQUENCE: 92

Gly Phe Asn Ile Tyr Tyr Ser Tyr
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic construct

<400> SEQUENCE: 93

Gly Phe Asn Ile Tyr Tyr Tyr Ser
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic construct

<400> SEQUENCE: 94

Gly Phe Asn Ile Ser Tyr Ser Ser
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic construct

<400> SEQUENCE: 95

Gly Phe Asn Phe Ser Ser Ser Ser
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic construct

<400> SEQUENCE: 96

Gly Phe Asn Leu Ser Tyr Ser Ser
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic construct

<400> SEQUENCE: 97

Gly Phe Asn Ile Ser Tyr Ser Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic construct

<400> SEQUENCE: 98
```

```
Gly Phe Asn Ile Ser Tyr Tyr Tyr
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic construct

<400> SEQUENCE: 99

Gly Phe Asn Ile Ser Tyr Tyr Tyr
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic construct

<400> SEQUENCE: 100

Gly Phe Asn Ile Tyr Ser Ser Tyr
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic construct

<400> SEQUENCE: 101

Gly Phe Asn Leu Tyr Tyr Tyr Tyr
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic construct

<400> SEQUENCE: 102

Gly Phe Asn Leu Ser Tyr Ser Ser
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic construct

<400> SEQUENCE: 103

Gly Phe Asn Ile Tyr Ser Ser Tyr
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic construct

<400> SEQUENCE: 104
```

-continued

```
Gly Phe Asn Ile Tyr Tyr Ser Ser
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic construct

<400> SEQUENCE: 105

Gly Phe Asn Ile Ser Tyr Ser Ser
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic construct

<400> SEQUENCE: 106

Gly Phe Asn Ile Ser Tyr Tyr Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic construct

<400> SEQUENCE: 107

Gly Phe Asn Leu Ser Tyr Tyr Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: Synthetic construct

<400> SEQUENCE: 108

Gly Phe Asn Leu Ser Tyr Ser Ser
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic construct

<400> SEQUENCE: 109

Gly Phe Asn Ile Ser Tyr Ser Tyr
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic construct

<400> SEQUENCE: 110

Gly Phe Asn Leu Tyr Ser Ser Tyr
```

```
1               5

<210> SEQ ID NO 111
<211> LENGTH: 8
<212> TYPE: PRT
<213> ORGANISM: Artificial Sequence
<220> FEATURE:
<223> OTHER INFORMATION: Synthetic construct

<400> SEQUENCE: 111

Gly Phe Asn Ile Ser Tyr Ser Tyr
1               5

<210> SEQ ID NO 112
<211> LENGTH: 8
<212> TYPE: PRT
<213> ORGANISM: Artificial Sequence
<220> FEATURE:
<223> OTHER INFORMATION: Synthetic construct

<400> SEQUENCE: 112

Gly Phe Asn Ile Tyr Tyr Tyr Tyr
1               5

<210> SEQ ID NO 113
<211> LENGTH: 8
<212> TYPE: PRT
<213> ORGANISM: Artificial Sequence
<220> FEATURE:
<223> OTHER INFORMATION: Synthetic construct

<400> SEQUENCE: 113

Ile Tyr Ser Ser Ser Gly Ser Thr
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic construct

<400> SEQUENCE: 114

Ile Tyr Pro Ser Ser Gly Ser Thr
1               5

<210> SEQ ID NO 115
<211> LENGTH: 8
<212> TYPE: PRT
<213> ORGANISM: Artificial Sequence
<220> FEATURE:
<223> OTHER INFORMATION: Synthetic construct

<400> SEQUENCE: 115

Ile Ser Ser Ser Ser Ser Ser Thr
1               5

<210> SEQ ID NO 116
<211> LENGTH: 8
<212> TYPE: PRT
<213> ORGANISM: Artificial Sequence
<220> FEATURE:
<223> OTHER INFORMATION: Synthetic construct

<400> SEQUENCE: 116

Ile Tyr Ser Tyr Ser Ser Tyr Thr
1               5
```

-continued

```
<210> SEQ ID NO 117
<211> LENGTH: 8
<212> TYPE: PRT
<213> ORGANISM: Artificial Sequence
<220> FEATURE:
<223> OTHER INFORMATION: Synthetic construct

<400> SEQUENCE: 117

Ile Ser Ser Ser Ser Ser Ser Thr
1               5

<210> SEQ ID NO 118
<211> LENGTH: 8
<212> TYPE: PRT
<213> ORGANISM: Artificial Sequence
<220> FEATURE:
<223> OTHER INFORMATION: Synthetic construct

<400> SEQUENCE: 118

Ile Tyr Pro Tyr Ser Ser Tyr Thr
1               5

<210> SEQ ID NO 119
<211> LENGTH: 8
<212> TYPE: PRT
<213> ORGANISM: Artificial Sequence
<220> FEATURE:
<223> OTHER INFORMATION: Synthetic construct

<400> SEQUENCE: 119

Ile Ser Ser Ser Tyr Gly Tyr Thr
1               5

<210> SEQ ID NO 120
<211> LENGTH: 8
<212> TYPE: PRT
<213> ORGANISM: Artificial Sequence
<220> FEATURE:
<223> OTHER INFORMATION: Synthetic construct

<400> SEQUENCE: 120

Ile Tyr Ser Ser Tyr Ser Tyr Thr
1               5

<210> SEQ ID NO 121
<211> LENGTH: 8
<212> TYPE: PRT
<213> ORGANISM: Artificial Sequence
<220> FEATURE:
<223> OTHER INFORMATION: Synthetic construct

<400> SEQUENCE: 121

Ile Ser Ser Ser Tyr Gly Tyr Thr
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic construct

<400> SEQUENCE: 122

Ile Ser Ser Tyr Ser Gly Ser Thr
1               5
```

-continued

```
<210> SEQ ID NO 123
<211> LENGTH: 8
<212> TYPE: PRT
<213> ORGANISM: Artificial Sequence
<220> FEATURE:
<223> OTHER INFORMATION: Synthetic construct

<400> SEQUENCE: 123

Ile Tyr Pro Ser Tyr Ser Tyr Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic construct

<400> SEQUENCE: 124

Ile Ser Ser Ser Ser Gly Tyr Thr
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic construct

<400> SEQUENCE: 125

Ile Tyr Ser Ser Ser Ser Ser Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic construct

<400> SEQUENCE: 126

Ile Tyr Pro Tyr Ser Gly Tyr Thr
1               5

<210> SEQ ID NO 127
<211> LENGTH: 8
<212> TYPE: PRT
<213> ORGANISM: Artificial Sequence
<220> FEATURE:
<223> OTHER INFORMATION: Synthetic construct

<400> SEQUENCE: 127

Ile Ser Ser Ser Ser Gly Tyr Thr
1               5

<210> SEQ ID NO 128
<211> LENGTH: 8
<212> TYPE: PRT
<213> ORGANISM: Artificial Sequence
<220> FEATURE:
<223> OTHER INFORMATION: Synthetic construct

<400> SEQUENCE: 128

Ile Tyr Pro Tyr Ser Ser Ser Thr
1               5
```

-continued

```
<210> SEQ ID NO 129
<211> LENGTH: 8
<212> TYPE: PRT
<213> ORGANISM: Artificial Sequence
<220> FEATURE:
<223> OTHER INFORMATION: Synthetic construct

<400> SEQUENCE: 129

Ile Tyr Pro Ser Ser Ser Ser Thr
1               5

<210> SEQ ID NO 130
<211> LENGTH: 8
<212> TYPE: PRT
<213> ORGANISM: Artificial Sequence
<220> FEATURE:
<223> OTHER INFORMATION: Synthetic construct

<400> SEQUENCE: 130

Ile Tyr Ser Ser Tyr Gly Tyr Thr
1               5

<210> SEQ ID NO 131
<211> LENGTH: 8
<212> TYPE: PRT
<213> ORGANISM: Artificial Sequence
<220> FEATURE:
<223> OTHER INFORMATION: Synthetic construct

<400> SEQUENCE: 131

Ile Tyr Pro Ser Tyr Ser Tyr Thr
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic construct

<400> SEQUENCE: 132

Ile Ser Ser Ser Tyr Gly Tyr Thr
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic construct

<400> SEQUENCE: 133

Ile Tyr Ser Ser Tyr Ser Ser Thr
1               5

<210> SEQ ID NO 134
<211> LENGTH: 8
<212> TYPE: PRT
<213> ORGANISM: Artificial Sequence
<220> FEATURE:
<223> OTHER INFORMATION: Synthetic construct

<400> SEQUENCE: 134

Ile Tyr Ser Ser Ser Gly Ser Thr
1               5

<210> SEQ ID NO 135
```

```
<211> LENGTH: 8
<212> TYPE: PRT
<213> ORGANISM: Artificial Sequence
<220> FEATURE:
<223> OTHER INFORMATION: Synthetic construct

<400> SEQUENCE: 135

Ile Tyr Pro Ser Ser Gly Ser Thr
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic construct

<400> SEQUENCE: 136

Ile Tyr Pro Ser Ser Gly Ser Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Synthetic construct

<400> SEQUENCE: 137

Ile Ser Pro Tyr Ser Gly Tyr Thr
1               5

<210> SEQ ID NO 138
<211> LENGTH: 8
<212> TYPE: PRT
<213> ORGANISM: Artificial Sequence
<220> FEATURE:
<223> OTHER INFORMATION: Synthetic construct

<400> SEQUENCE: 138

Ile Tyr Ser Ser Ser Gly Ser Thr
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic construct

<400> SEQUENCE: 139

Ile Tyr Ser Tyr Tyr Ser Ser Thr
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic construct

<400> SEQUENCE: 140

Ile Tyr Pro Ser Tyr Gly Ser Thr
1               5

<210> SEQ ID NO 141
<211> LENGTH: 8
```

<212> TYPE: PRT
<213> ORGANISM: Artificial Sequence
<220> FEATURE:
<223> OTHER INFORMATION: Synthetic construct

<400> SEQUENCE: 141

Ile Tyr Pro Ser Ser Ser Ser Thr
1               5

<210> SEQ ID NO 142
<211> LENGTH: 8
<212> TYPE: PRT
<213> ORGANISM: Artificial Sequence
<220> FEATURE:
<223> OTHER INFORMATION: Synthetic construct

<400> SEQUENCE: 142

Ile Tyr Pro Ser Tyr Gly Tyr Thr
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic construct

<400> SEQUENCE: 143

Ile Tyr Pro Ser Tyr Ser Ser Thr
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic construct

<400> SEQUENCE: 144

Ile Tyr Pro Ser Ser Ser Ser Thr
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic construct

<400> SEQUENCE: 145

Ile Tyr Pro Tyr Ser Gly Ser Thr
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic construct

<400> SEQUENCE: 146

Ile Ser Pro Tyr Ser Gly Ser Thr
1               5

<210> SEQ ID NO 147
<211> LENGTH: 8
<212> TYPE: PRT

-continued

```
<213> ORGANISM: Artificial Sequence
<220> FEATURE:
<223> OTHER INFORMATION: Synthetic construct

<400> SEQUENCE: 147

Ile Tyr Ser Ser Tyr Ser Ser Thr
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic construct

<400> SEQUENCE: 148

Ile Tyr Ser Ser Tyr Gly Tyr Thr
1               5

<210> SEQ ID NO 149
<211> LENGTH: 8
<212> TYPE: PRT
<213> ORGANISM: Artificial Sequecne
<220> FEATURE:
<223> OTHER INFORMATION: Synthetic construct

<400> SEQUENCE: 149

Ile Tyr Ser Ser Ser Gly Ser Thr
1               5

<210> SEQ ID NO 150
<211> LENGTH: 8
<212> TYPE: PRT
<213> ORGANISM: Artificial Sequence
<220> FEATURE:
<223> OTHER INFORMATION: Synthetic construct

<400> SEQUENCE: 150

Ile Tyr Pro Ser Ser Gly Ser Thr
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic construct

<400> SEQUENCE: 151

Ile Tyr Ser Ser Ser Gly Ser Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic construct

<400> SEQUENCE: 152

Ala Arg Ala Val Trp Gly Leu Asp Tyr
1               5

<210> SEQ ID NO 153
<211> LENGTH: 7
<212> TYPE: PRT
<213> ORGANISM: Artificial Sequence
```

-continued

```
<220> FEATURE:
<223> OTHER INFORMATION: Synthetic construct

<400> SEQUENCE: 153

Ala Arg Gly Ala Leu Asp Tyr
1               5

<210> SEQ ID NO 154
<211> LENGTH: 15
<212> TYPE: PRT
<213> ORGANISM: Artificial Sequence
<220> FEATURE:
<223> OTHER INFORMATION: Synthetic construct

<400> SEQUENCE: 154

Ala Arg Ser Trp Tyr Tyr Trp Ser Pro Ser Ser Gly Met Asp Tyr
1               5                   10                  15

<210> SEQ ID NO 155
<211> LENGTH: 7
<212> TYPE: PRT
<213> ORGANISM: Artificial Sequence
<220> FEATURE:
<223> OTHER INFORMATION: Synthetic construct

<400> SEQUENCE: 155

Ala Arg Gly Ala Ile Asp Tyr
1               5

<210> SEQ ID NO 156
<211> LENGTH: 11
<212> TYPE: PRT
<213> ORGANISM: Artificial Sequence
<220> FEATURE:
<223> OTHER INFORMATION: Synthetic construct

<400> SEQUENCE: 156

Ala Arg Ser Trp Tyr Ala Trp Ala Met Asp Tyr
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Synthetic construct

<400> SEQUENCE: 157

Ala Arg Ser Gly Tyr Ala Leu Asp Tyr
1               5

<210> SEQ ID NO 158
<211> LENGTH: 19
<212> TYPE: PRT
<213> ORGANISM: Artificial Sequence
<220> FEATURE:
<223> OTHER INFORMATION: Synthetic construct

<400> SEQUENCE: 158

Ala Arg Thr Val Arg Gly Ser Lys Lys Pro Tyr Phe Ser Gly Trp Ala
1               5                   10                  15

Met Asp Tyr

<210> SEQ ID NO 159
<211> LENGTH: 16
<212> TYPE: PRT
```

-continued

```
<213> ORGANISM: Artificial Sequence
<220> FEATURE:
<223> OTHER INFORMATION: Synthetic construct

<400> SEQUENCE: 159

Ala Arg Ser Ser Trp Gly Ala Tyr Ile Val Ser Tyr Gly Phe Asp Tyr
1               5                   10                  15

<210> SEQ ID NO 160
<211> LENGTH: 13
<212> TYPE: PRT
<213> ORGANISM: Artificial Sequence
<220> FEATURE:
<223> OTHER INFORMATION: Synthetic construct

<400> SEQUENCE: 160

Ala Arg Ala Tyr Tyr Gly His Phe His Ala Met Asp Tyr
1               5                   10

<210> SEQ ID NO 161
<211> LENGTH: 19
<212> TYPE: PRT
<213> ORGANISM: Artificial Sequence
<220> FEATURE:
<223> OTHER INFORMATION: Synthetic construct

<400> SEQUENCE: 161

Ala Arg Thr Val Arg Gly Ser Lys Lys Pro Tyr Phe Ser Gly Trp Ala
1               5                   10                  15

Met Asp Tyr

<210> SEQ ID NO 162
<211> LENGTH: 7
<212> TYPE: PRT
<213> ORGANISM: Artificial Sequence
<220> FEATURE:
<223> OTHER INFORMATION: Synthetic construct

<400> SEQUENCE: 162

Ala Arg Gly Ala Met Asp Tyr
1               5

<210> SEQ ID NO 163
<211> LENGTH: 11
<212> TYPE: PRT
<213> ORGANISM: Artificial Sequence
<220> FEATURE:
<223> OTHER INFORMATION: Synthetic construct

<400> SEQUENCE: 163

Ala Arg Tyr Phe Trp Trp Tyr Gly Phe Asp Tyr
1               5                   10

<210> SEQ ID NO 164
<211> LENGTH: 19
<212> TYPE: PRT
<213> ORGANISM: Artificial Sequence
<220> FEATURE:
<223> OTHER INFORMATION: Synthetic construct

<400> SEQUENCE: 164

Ala Arg Thr Val Arg Gly Ser Lys Lys Pro Tyr Phe Ser Gly Trp Ala
1               5                   10                  15

Met Asp Tyr
```

-continued

```
<210> SEQ ID NO 165
<211> LENGTH: 10
<212> TYPE: PRT
<213> ORGANISM: Artificial Sequence
<220> FEATURE:
<223> OTHER INFORMATION: Synthetic construct

<400> SEQUENCE: 165

Ala Arg Tyr Gly Tyr Tyr Gly Leu Asp Tyr
1               5                   10

<210> SEQ ID NO 166
<211> LENGTH: 15
<212> TYPE: PRT
<213> ORGANISM: Artificial Sequence
<220> FEATURE:
<223> OTHER INFORMATION: Synthetic construct

<400> SEQUENCE: 166

Ala Arg Gly Tyr His Tyr Tyr Pro Tyr Tyr Ser Gly Leu Asp Tyr
1               5                   10                  15

<210> SEQ ID NO 167
<211> LENGTH: 10
<212> TYPE: PRT
<213> ORGANISM: Artificial Sequence
<220> FEATURE:
<223> OTHER INFORMATION: Synthetic construct

<400> SEQUENCE: 167

Ala Arg Tyr Gly Tyr Tyr Gly Met Asp Tyr
1               5                   10

<210> SEQ ID NO 168
<211> LENGTH: 16
<212> TYPE: PRT
<213> ORGANISM: Artificial Sequence
<220> FEATURE:
<223> OTHER INFORMATION: Synthetic construct

<400> SEQUENCE: 168

Ala Arg Ala Val Trp Tyr Tyr Trp Trp Val Trp Gly Gly Phe Asp Tyr
1               5                   10                  15

<210> SEQ ID NO 169
<211> LENGTH: 10
<212> TYPE: PRT
<213> ORGANISM: Artificial Sequence
<220> FEATURE:
<223> OTHER INFORMATION: Synthetic construct

<400> SEQUENCE: 169

Ala Arg Phe Gly Tyr Trp Ala Ile Asp Tyr
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Synthetic construct

<400> SEQUENCE: 170

Ala Arg Gly Gly Met Asp Tyr
1               5

<210> SEQ ID NO 171
```

-continued

```
<211> LENGTH: 19
<212> TYPE: PRT
<213> ORGANISM: Artificial Sequence
<220> FEATURE:
<223> OTHER INFORMATION: Synthetic construct

<400> SEQUENCE: 171

Ala Arg Thr Val Arg Gly Ser Lys Lys Pro Tyr Phe Ser Gly Trp Ala
1               5                   10                  15

Met Asp Tyr

<210> SEQ ID NO 172
<211> LENGTH: 10
<212> TYPE: PRT
<213> ORGANISM: Artificial Sequence
<220> FEATURE:
<223> OTHER INFORMATION: Synthetic construct

<400> SEQUENCE: 172

Ala Arg Tyr Gly Tyr Phe Gly Leu Asp Tyr
1               5                   10

<210> SEQ ID NO 173
<211> LENGTH: 7
<212> TYPE: PRT
<213> ORGANISM: Artificial Sequence
<220> FEATURE:
<223> OTHER INFORMATION: Synthetic construct

<400> SEQUENCE: 173

Ala Arg Gly Gly Leu Asp Tyr
1               5

<210> SEQ ID NO 174
<211> LENGTH: 10
<212> TYPE: PRT
<213> ORGANISM: Artificial Sequence
<220> FEATURE:
<223> OTHER INFORMATION: Synthetic construct

<400> SEQUENCE: 174

Ala Arg Tyr Gly Tyr Tyr Gly Phe Asp Tyr
1               5                   10

<210> SEQ ID NO 175
<211> LENGTH: 8
<212> TYPE: PRT
<213> ORGANISM: Artificial Sequence
<220> FEATURE:
<223> OTHER INFORMATION: Synthetic construct

<400> SEQUENCE: 175

Ala Arg Tyr Tyr Ala Met Asp Tyr
1               5

<210> SEQ ID NO 176
<211> LENGTH: 22
<212> TYPE: PRT
<213> ORGANISM: Artificial Sequence
<220> FEATURE:
<223> OTHER INFORMATION: Synthetic construct

<400> SEQUENCE: 176

Ala Arg Gly Ser Tyr Trp Tyr Val Gly Gly Gly Trp Trp Val Ser Gly
1               5                   10                  15

His Gly Gly Met Asp Tyr
```

-continued

```
        20
```

<210> SEQ ID NO 177
<211> LENGTH: 19
<212> TYPE: PRT
<213> ORGANISM: Artificial Sequence
<220> FEATURE:
<223> OTHER INFORMATION: Synthetic construct

<400> SEQUENCE: 177

Ala Arg Thr Val Arg Gly Ser Lys Lys Pro Tyr Phe Ser Gly Trp Ala
1               5                   10                  15

Met Asp Tyr

<210> SEQ ID NO 178
<211> LENGTH: 7
<212> TYPE: PRT
<213> ORGANISM: Artificial Sequence
<220> FEATURE:
<223> OTHER INFORMATION: Synthetic construct

<400> SEQUENCE: 178

Ala Arg Ala Ala Phe Asp Tyr
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic construct

<400> SEQUENCE: 179

Ala Arg Ala Ala Met Asp Tyr
1               5

<210> SEQ ID NO 180
<211> LENGTH: 18
<212> TYPE: DNA
<213> ORGANISM: Artificial Sequence
<220> FEATURE:
<223> OTHER INFORMATION: Synthetic construct

<400> SEQUENCE: 180
cagtccgtgt ccagcgct                                              18

<210> SEQ ID NO 181
<211> LENGTH: 9
<212> TYPE: DNA
<213> ORGANISM: Artificial Sequence
<220> FEATURE:
<223> OTHER INFORMATION: Synthetic construct

<400> SEQUENCE: 181 tcggcatcc                                                        9

<210> SEQ ID NO 182
<211> LENGTH: 33
<212> TYPE: DNA
<213> ORGANISM: Artificial Sequence
<220> FEATURE:
<223> OTHER INFORMATION: Synthetic construct

<400> SEQUENCE: 182
cagcaatggt ggggttacta ctctctgatc acg                             33

-continued

```
<210> SEQ ID NO 183
<211> LENGTH: 33
<212> TYPE: DNA
<213> ORGANISM: Artificial Sequence
<220> FEATURE:
<223> OTHER INFORMATION: Synthetic construct

<400> SEQUENCE: 183
cagcaatggt actcttctta cggtctgatc acg                               33

<210> SEQ ID NO 184
<211> LENGTH: 33
<212> TYPE: DNA
<213> ORGANISM: Artificial Sequence
<220> FEATURE:
<223> OTHER INFORMATION: Synthetic construct

<400> SEQUENCE: 184
cagcaatggt actctggttc ttctctgttc acg                               33

<210> SEQ ID NO 185
<211> LENGTH: 24
<212> TYPE: DNA
<213> ORGANISM: Artificial Sequence
<220> FEATURE:
<223> OTHER INFORMATION: Synthetic construct

<400> SEQUENCE: 185
cagcaaggtg gtttcctgat cacg                                         24

<210> SEQ ID NO 186
<211> LENGTH: 33
<212> TYPE: DNA
<213> ORGANISM: Artificial Sequence
<220> FEATURE:
<223> OTHER INFORMATION: Synthetic construct

<400> SEQUENCE: 186
cagcaatggt acgctttcgg tgctctgatc acg                               33

<210> SEQ ID NO 187
<211> LENGTH: 33
<212> TYPE: DNA
<213> ORGANISM: Artificial Sequence
<220> FEATURE:
<223> OTHER INFORMATION: Synthetic construct

<400> SEQUENCE: 187
cagcaatggg gtggtggttc ttctctgttc acg                               33

<210> SEQ ID NO 188
<211> LENGTH: 27
<212> TYPE: DNA
<213> ORGANISM: Artificial Sequence
<220> FEATURE:
<223> OTHER INFORMATION: Synthetic construct

<400> SEQUENCE: 188
cagcaatctt cttattctct gatcacg                                      27

<210> SEQ ID NO 189
<211> LENGTH: 36
<212> TYPE: DNA
<213> ORGANISM: Artificial Sequence
<220> FEATURE:
<223> OTHER INFORMATION: Synthetic construct
```

```
<400> SEQUENCE: 189
cagcaatctt cttggtacta cggttacccg ttcacg                              36

<210> SEQ ID NO 190
<211> LENGTH: 30
<212> TYPE: DNA
<213> ORGANISM: Artificial Sequence
<220> FEATURE:
<223> OTHER INFORMATION: Synthetic construct

<400> SEQUENCE: 190
cagcaatggt cttggggttt cctgatcacg                                     30

<210> SEQ ID NO 191
<211> LENGTH: 33
<212> TYPE: DNA
<213> ORGANISM: Artificial Sequence
<220> FEATURE:
<223> OTHER INFORMATION: Synthetic construct

<400> SEQUENCE: 191
cagcaagttg gttactggtg gggtctgatc acg                                 33

<210> SEQ ID NO 192
<211> LENGTH: 27
<212> TYPE: DNA
<213> ORGANISM: Artificial Sequence
<220> FEATURE:
<223> OTHER INFORMATION: Synthetic construct

<400> SEQUENCE: 192
cagcaatctt cttattctct gatcacg                                        27

<210> SEQ ID NO 193
<211> LENGTH: 33
<212> TYPE: DNA
<213> ORGANISM: Artificial Sequence
<220> FEATURE:
<223> OTHER INFORMATION: Synthetic construct

<400> SEQUENCE: 193
cagcaatctt ggtcttacca ttacctgatc acg                                 33

<210> SEQ ID NO 194
<211> LENGTH: 30
<212> TYPE: DNA
<213> ORGANISM: Artificial Sequence
<220> FEATURE:
<223> OTHER INFORMATION: Synthetic construct

<400> SEQUENCE: 194
cagcaatggt acggttctca tctgatcacg                                     30

<210> SEQ ID NO 195
<211> LENGTH: 27
<212> TYPE: DNA
<213> ORGANISM: Artificial Sequence
<220> FEATURE:
<223> OTHER INFORMATION: Synthetic construct

<400> SEQUENCE: 195
cagcaaggtc cgtggtaccc gttcacg                                        27

<210> SEQ ID NO 196
```

```
<211> LENGTH: 30
<212> TYPE: DNA
<213> ORGANISM: Artificial Sequence
<220> FEATURE:
<223> OTHER INFORMATION: Synthetic construct

<400> SEQUENCE: 196
cagcaattct acttcccgta cctgatcacg                                    30

<210> SEQ ID NO 197
<211> LENGTH: 33
<212> TYPE: DNA
<213> ORGANISM: Artificial Sequence
<220> FEATURE:
<223> OTHER INFORMATION: Synthetic construct

<400> SEQUENCE: 197
cagcaatggg gtgtttctca ttacctgttc acg                                33

<210> SEQ ID NO 198
<211> LENGTH: 30
<212> TYPE: DNA
<213> ORGANISM: Artificial Sequence
<220> FEATURE:
<223> OTHER INFORMATION: Synthetic construct

<400> SEQUENCE: 198
cagcaatggt actacggttc tctgatcacg                                    30

<210> SEQ ID NO 199
<211> LENGTH: 30
<212> TYPE: DNA
<213> ORGANISM: Artificial Sequence
<220> FEATURE:
<223> OTHER INFORMATION: Synthetic construct

<400> SEQUENCE: 199
cagcaagctt actaccattc tctgatcacg                                    30

<210> SEQ ID NO 200
<211> LENGTH: 33
<212> TYPE: DNA
<213> ORGANISM: Artificial Sequence
<220> FEATURE:
<223> OTHER INFORMATION: Synthetic construct

<400> SEQUENCE: 200
cagcaatggt accattaccc gtacctgatc acg                                33

<210> SEQ ID NO 201
<211> LENGTH: 27
<212> TYPE: DNA
<213> ORGANISM: Artificial Sequence
<220> FEATURE:
<223> OTHER INFORMATION: Synthetic construct

<400> SEQUENCE: 201
cagcaatctt cttattctct gatcacg                                       27

<210> SEQ ID NO 202
<211> LENGTH: 30
<212> TYPE: DNA
<213> ORGANISM: Artificial Sequence
<220> FEATURE:
<223> OTHER INFORMATION: Synthetic construct

<400> SEQUENCE: 202
```

```
cagcaagctt tcggtgcttc tctgttcacg                                      30

<210> SEQ ID NO 203
<211> LENGTH: 36
<212> TYPE: DNA
<213> ORGANISM: Artificial Sequence
<220> FEATURE:
<223> OTHER INFORMATION: Synthetic construct

<400> SEQUENCE: 203
cagcaatggt actcttctgg tcatgttctg atcacg                               36

<210> SEQ ID NO 204
<211> LENGTH: 30
<212> TYPE: DNA
<213> ORGANISM: Artificial Sequence
<220> FEATURE:
<223> OTHER INFORMATION: Synthetic construct

<400> SEQUENCE: 204
cagcaatggt tcgctggtgc tctgatcacg                                      30

<210> SEQ ID NO 205
<211> LENGTH: 30
<212> TYPE: DNA
<213> ORGANISM: Artificial Sequence
<220> FEATURE:
<223> OTHER INFORMATION: Synthetic construct

<400> SEQUENCE: 205
cagcaatggt acgctggttc tctgatcacg                                      30

<210> SEQ ID NO 206
<211> LENGTH: 33
<212> TYPE: DNA
<213> ORGANISM: Artificial Sequence
<220> FEATURE:
<223> OTHER INFORMATION: Synthetic construct

<400> SEQUENCE: 206
cagcaatctt tcgtttaccc gtacctgatc acg                                  33

<210> SEQ ID NO 207
<211> LENGTH: 33
<212> TYPE: DNA
<213> ORGANISM: Artificial Sequence
<220> FEATURE:
<223> OTHER INFORMATION: Synthetic construct

<400> SEQUENCE: 207
cagcaatggt acggttactc tgctctgatc acg                                  33

<210> SEQ ID NO 208
<211> LENGTH: 33
<212> TYPE: DNA
<213> ORGANISM: Artificial Sequence
<220> FEATURE:
<223> OTHER INFORMATION: Synthetic construct

<400> SEQUENCE: 208
cagcaatggt actctggtca ttctctgatc acg                                  33

<210> SEQ ID NO 209
<211> LENGTH: 33
<212> TYPE: DNA
```

-continued

```
<213> ORGANISM: Artificial Sequence
<220> FEATURE:
<223> OTHER INFORMATION: Synthetic construct

<400> SEQUENCE: 209
cagcaagctt gggtttacgc ttctctgttc acg                                  33

<210> SEQ ID NO 210
<211> LENGTH: 33
<212> TYPE: DNA
<213> ORGANISM: Artificial Sequence
<220> FEATURE:
<223> OTHER INFORMATION: Synthetic construct

<400> SEQUENCE: 210
cagcaatggt accatggtgg ttctctgttc acg                                  33

<210> SEQ ID NO 211
<211> LENGTH: 33
<212> TYPE: DNA
<213> ORGANISM: Artificial Sequence
<220> FEATURE:
<223> OTHER INFORMATION: Synthetic construct

<400> SEQUENCE: 211
cagcaatggg gttctcatgg ttacctgatc acg                                  33

<210> SEQ ID NO 212
<211> LENGTH: 27
<212> TYPE: DNA
<213> ORGANISM: Artificial Sequence
<220> FEATURE:
<223> OTHER INFORMATION: Synthetic construct

<400> SEQUENCE: 212
cagcaagctt tctactaccc gatcacg                                         27

<210> SEQ ID NO 213
<211> LENGTH: 33
<212> TYPE: DNA
<213> ORGANISM: Artificial Sequence
<220> FEATURE:
<223> OTHER INFORMATION: Synthetic construct

<400> SEQUENCE: 213
cagcaatggt actcttctta cggtctgatc acg                                  33

<210> SEQ ID NO 214
<211> LENGTH: 30
<212> TYPE: DNA
<213> ORGANISM: Artificial Sequence
<220> FEATURE:
<223> OTHER INFORMATION: Synthetic construct

<400> SEQUENCE: 214
cagcaatggt acggtccgta cctgatcacg                                      30

<210> SEQ ID NO 215
<211> LENGTH: 27
<212> TYPE: DNA
<213> ORGANISM: Artificial Sequence
<220> FEATURE:
<223> OTHER INFORMATION: Synthetic construct

<400> SEQUENCE: 215
cagcaatctt cttattctct gatcacg                                         27
```

```
<210> SEQ ID NO 216
<211> LENGTH: 33
<212> TYPE: DNA
<213> ORGANISM: Artificial Sequence
<220> FEATURE:
<223> OTHER INFORMATION: Synthetic construct

<400> SEQUENCE: 216
cagcaatggt acggttcttt cgctctgatc acg                                 33

<210> SEQ ID NO 217
<211> LENGTH: 36
<212> TYPE: DNA
<213> ORGANISM: Artificial Sequence
<220> FEATURE:
<223> OTHER INFORMATION: Synthetic construct

<400> SEQUENCE: 217
cagcaattct ggtggtacgc ttcttggctg ttcacg                              36

<210> SEQ ID NO 218
<211> LENGTH: 30
<212> TYPE: DNA
<213> ORGANISM: Artificial Sequence
<220> FEATURE:
<223> OTHER INFORMATION: Synthetic construct

<400> SEQUENCE: 218
cagcaatggt accattacgg tctgatcacg                                     30

<210> SEQ ID NO 219
<211> LENGTH: 33
<212> TYPE: DNA
<213> ORGANISM: Artificial Sequence
<220> FEATURE:
<223> OTHER INFORMATION: Synthetic construct

<400> SEQUENCE: 219
cagcaatggt acggtggtta cgctctgatc acg                                 33

<210> SEQ ID NO 220
<211> LENGTH: 30
<212> TYPE: DNA
<213> ORGANISM: Artificial Sequence
<220> FEATURE:
<223> OTHER INFORMATION: Synthetic construct

<400> SEQUENCE: 220
cagcaatggt acgctgcttc tctgatcacg                                     30

<210> SEQ ID NO 221
<211> LENGTH: 24
<212> TYPE: DNA
<213> ORGANISM: Artificial Sequence
<220> FEATURE:
<223> OTHER INFORMATION: Synthetic construct

<400> SEQUENCE: 221
ggcttcaaca tctattctta ttct                                           24

<210> SEQ ID NO 222
<211> LENGTH: 24
<212> TYPE: DNA
<213> ORGANISM: Artificial Sequence
<220> FEATURE:
```

<223> OTHER INFORMATION: Synthetic construct

<400> SEQUENCE: 222
ggcttcaacc tctattatta ttat                                      24

<210> SEQ ID NO 223
<211> LENGTH: 24
<212> TYPE: DNA
<213> ORGANISM: Artificial Sequence
<220> FEATURE:
<223> OTHER INFORMATION: Synthetic construct

<400> SEQUENCE: 223
ggcttcaacc tctcttctta ttat                                      24

<210> SEQ ID NO 224
<211> LENGTH: 24
<212> TYPE: DNA
<213> ORGANISM: Artificial Sequence
<220> FEATURE:
<223> OTHER INFORMATION: Synthetic construct

<400> SEQUENCE: 224
ggcttcaaca tctcttattc ttat                                      24

<210> SEQ ID NO 225
<211> LENGTH: 24
<212> TYPE: DNA
<213> ORGANISM: Artificial Sequence
<220> FEATURE:
<223> OTHER INFORMATION: Synthetic construct

<400> SEQUENCE: 225
ggcttcaaca tctcttatta ttat                                      24

<210> SEQ ID NO 226
<211> LENGTH: 24
<212> TYPE: DNA
<213> ORGANISM: Artificial Sequence
<220> FEATURE:
<223> OTHER INFORMATION: Synthetic contruct

<400> SEQUENCE: 226
ggcttcaacc tctcttatta ttat                                      24

<210> SEQ ID NO 227
<211> LENGTH: 24
<212> TYPE: DNA
<213> ORGANISM: Artificial Sequence
<220> FEATURE:
<223> OTHER INFORMATION: Synthetic construct

<400> SEQUENCE: 227
ggcttcaaca tctattctta ttct                                      24

<210> SEQ ID NO 228
<211> LENGTH: 24
<212> TYPE: DNA
<213> ORGANISM: Artificial Sequence
<220> FEATURE:
<223> OTHER INFORMATION: Synthetic construct

<400> SEQUENCE: 228
ggcttcaacc tctcttatta ttat                                      24

-continued

```
<210> SEQ ID NO 229
<211> LENGTH: 24
<212> TYPE: DNA
<213> ORGANISM: Artificial Sequence
<220> FEATURE:
<223> OTHER INFORMATION: Synthetic construct

<400> SEQUENCE: 229
ggcttcaact tttcttcttc ttct                                              24

<210> SEQ ID NO 230
<211> LENGTH: 24
<212> TYPE: DNA
<213> ORGANISM: Artificial Sequence
<220> FEATURE:
<223> OTHER INFORMATION: Synthetic construct

<400> SEQUENCE: 230
ggcttcaaca tctattcttc ttat                                              24

<210> SEQ ID NO 231
<211> LENGTH: 24
<212> TYPE: DNA
<213> ORGANISM: Artificial Sequence
<220> FEATURE:
<223> OTHER INFORMATION: Synthetic construct

<400> SEQUENCE: 231
ggcttcaact tttcttcttc ttct                                              24

<210> SEQ ID NO 232
<211> LENGTH: 24
<212> TYPE: DNA
<213> ORGANISM: Artificial Sequence
<220> FEATURE:
<223> OTHER INFORMATION: Synthetic construct

<400> SEQUENCE: 232
ggcttcaaca tctcttcttc ttat                                              24

<210> SEQ ID NO 233
<211> LENGTH: 24
<212> TYPE: DNA
<213> ORGANISM: Artificial Sequence
<220> FEATURE:
<223> OTHER INFORMATION: Synthetic construct

<400> SEQUENCE: 233
ggcttcaaca tctcttattc ttat                                              24

<210> SEQ ID NO 234
<211> LENGTH: 24
<212> TYPE: DNA
<213> ORGANISM: Artificial Sequence
<220> FEATURE:
<223> OTHER INFORMATION: Synthetic construct

<400> SEQUENCE: 234
ggcttcaaca tctattattc ttct                                              24

<210> SEQ ID NO 235
<211> LENGTH: 24
<212> TYPE: DNA
<213> ORGANISM: Artificial Sequence
<220> FEATURE:
<223> OTHER INFORMATION: Synthetic construct
```

```
<400> SEQUENCE: 235
ggcttcaaca tctcttattc ttat                                                24

<210> SEQ ID NO 236
<211> LENGTH: 24
<212> TYPE: DNA
<213> ORGANISM: Artificial Sequence
<220> FEATURE:
<223> OTHER INFORMATION: Synthetic construct

<400> SEQUENCE: 236
ggcttcaaca tctcttattc ttct                                                24

<210> SEQ ID NO 237
<211> LENGTH: 24
<212> TYPE: DNA
<213> ORGANISM: Artificial Sequence
<220> FEATURE:
<223> OTHER INFORMATION: Synthetic contstruct

<400> SEQUENCE: 237
ggcttcaaca tctattattc ttat                                                24

<210> SEQ ID NO 238
<211> LENGTH: 24
<212> TYPE: DNA
<213> ORGANISM: Artificial Sequence
<220> FEATURE:
<223> OTHER INFORMATION: Synthetic construct

<400> SEQUENCE: 238
ggcttcaaca tctattatta ttct                                                24

<210> SEQ ID NO 239
<211> LENGTH: 24
<212> TYPE: DNA
<213> ORGANISM: Artificial Sequence
<220> FEATURE:
<223> OTHER INFORMATION: Synthetic construct

<400> SEQUENCE: 239
ggcttcaaca tctcttattc ttct                                                24

<210> SEQ ID NO 240
<211> LENGTH: 24
<212> TYPE: DNA
<213> ORGANISM: Artificial Sequence
<220> FEATURE:
<223> OTHER INFORMATION: Synthetic construct

<400> SEQUENCE: 240
ggcttcaact tttcttcttc ttct                                                24

<210> SEQ ID NO 241
<211> LENGTH: 24
<212> TYPE: DNA
<213> ORGANISM: Artificial Sequence
<220> FEATURE:
<223> OTHER INFORMATION: Synthetic construct

<400> SEQUENCE: 241
ggcttcaacc tctcttattc ttct                                                24

<210> SEQ ID NO 242
<211> LENGTH: 24
```

-continued

```
<212> TYPE: DNA
<213> ORGANISM: Artificial Sequnece
<220> FEATURE:
<223> OTHER INFORMATION: Synthetic construct

<400> SEQUENCE: 242
ggcttcaaca tctcttattc ttat                                        24

<210> SEQ ID NO 243
<211> LENGTH: 24
<212> TYPE: DNA
<213> ORGANISM: Artificial Sequence
<220> FEATURE:
<223> OTHER INFORMATION: Synthetic construct

<400> SEQUENCE: 243
ggcttcaaca tctcttatta ttat                                        24

<210> SEQ ID NO 244
<211> LENGTH: 24
<212> TYPE: DNA
<213> ORGANISM: Artificial Sequence
<220> FEATURE:
<223> OTHER INFORMATION: Synthetic construct

<400> SEQUENCE: 244
ggcttcaaca tctcttatta ttat                                        24

<210> SEQ ID NO 245
<211> LENGTH: 24
<212> TYPE: DNA
<213> ORGANISM: Artificial Sequence
<220> FEATURE:
<223> OTHER INFORMATION: Synthetic construct

<400> SEQUENCE: 245
ggcttcaaca tctattcttc ttat                                        24

<210> SEQ ID NO 246
<211> LENGTH: 24
<212> TYPE: DNA
<213> ORGANISM: Artificial Sequence
<220> FEATURE:
<223> OTHER INFORMATION: Synthetic construct

<400> SEQUENCE: 246
ggcttcaacc tctattatta ttat                                        24

<210> SEQ ID NO 247
<211> LENGTH: 24
<212> TYPE: DNA
<213> ORGANISM: Artificial Sequence
<220> FEATURE:
<223> OTHER INFORMATION: Synthetic construct

<400> SEQUENCE: 247
ggcttcaaca tctcttattc ttat                                        24

<210> SEQ ID NO 248
<211> LENGTH: 24
<212> TYPE: DNA
<213> ORGANISM: Artificial Sequence
<220> FEATURE:
<223> OTHER INFORMATION: Synthetic construct

<400> SEQUENCE: 248
```
ggcttcaacc tctcttattc ttct                                               24

<210> SEQ ID NO 249
<211> LENGTH: 24
<212> TYPE: DNA
<213> ORGANISM: Artificial Sequence
<220> FEATURE:
<223> OTHER INFORMATION: Synthetic construct

<400> SEQUENCE: 249
ggcttcaaca tctattcttc ttat                                               24

<210> SEQ ID NO 250
<211> LENGTH: 24
<212> TYPE: DNA
<213> ORGANISM: Artificial Sequence
<220> FEATURE:
<223> OTHER INFORMATION: Synthetic construct

<400> SEQUENCE: 250
ggcttcaaca tctattattc ttct                                               24

<210> SEQ ID NO 251
<211> LENGTH: 24
<212> TYPE: DNA
<213> ORGANISM: Artificial Sequence
<220> FEATURE:
<223> OTHER INFORMATION: Synthetic construct

<400> SEQUENCE: 251
ggcttcaaca tctcttattc ttct                                               24

<210> SEQ ID NO 252
<211> LENGTH: 24
<212> TYPE: DNA
<213> ORGANISM: Artificial Sequence
<220> FEATURE:
<223> OTHER INFORMATION: Synthetic construct

<400> SEQUENCE: 252
ggcttcaaca tctcttatta ttat                                               24

<210> SEQ ID NO 253
<211> LENGTH: 24
<212> TYPE: DNA
<213> ORGANISM: Artificial Sequence
<220> FEATURE:
<223> OTHER INFORMATION: Synthetic construct

<400> SEQUENCE: 253
ggcttcaacc tctcttatta ttat                                               24

<210> SEQ ID NO 254
<211> LENGTH: 24
<212> TYPE: DNA
<213> ORGANISM: Artificial Sequence
<220> FEATURE:
<223> OTHER INFORMATION: Synthetic construct

<400> SEQUENCE: 254
ggcttcaacc tctcttattc ttct                                               24

<210> SEQ ID NO 255
<211> LENGTH: 24
<212> TYPE: DNA
<213> ORGANISM: Artificial Sequence
<220> FEATURE:
<223> OTHER INFORMATION: Synthetic construct

<400> SEQUENCE: 255
ggcttcaaca tctcttattc ttat                                              24

<210> SEQ ID NO 256
<211> LENGTH: 24
<212> TYPE: DNA
<213> ORGANISM: Artificial Sequence
<220> FEATURE:
<223> OTHER INFORMATION: Synthetic construct

<400> SEQUENCE: 256
ggcttcaacc tctattcttc ttat                                              24

<210> SEQ ID NO 257
<211> LENGTH: 24
<212> TYPE: DNA
<213> ORGANISM: Artificial Sequence
<220> FEATURE:
<223> OTHER INFORMATION: Synthetic construct

<400> SEQUENCE: 257
ggcttcaaca tctcttattc ttat                                              24

<210> SEQ ID NO 258
<211> LENGTH: 24
<212> TYPE: DNA
<213> ORGANISM: Artificial Sequence
<220> FEATURE:
<223> OTHER INFORMATION: Synthetic construct

<400> SEQUENCE: 258
ggcttcaaca tctattatta ttat                                              24

<210> SEQ ID NO 259
<211> LENGTH: 24
<212> TYPE: DNA
<213> ORGANISM: Artificial Sequence
<220> FEATURE:
<223> OTHER INFORMATION: Synthetic construct

<400> SEQUENCE: 259
ggcttcaaca tctcttatta ttat                                              24

<210> SEQ ID NO 260
<211> LENGTH: 24
<212> TYPE: DNA
<213> ORGANISM: Artificial Sequence
<220> FEATURE:
<223> OTHER INFORMATION: Synthetic construct

<400> SEQUENCE: 260
atttattctt cttctggctc tact                                              24

<210> SEQ ID NO 261
<211> LENGTH: 24
<212> TYPE: DNA
<213> ORGANISM: Artificial Sequence
<220> FEATURE:
<223> OTHER INFORMATION: Synthetic construct

<400> SEQUENCE: 261
atttatcctt cttctggctc tact                                              24

-continued

```
<210> SEQ ID NO 262
<211> LENGTH: 24
<212> TYPE: DNA
<213> ORGANISM: Artificial Sequence
<220> FEATURE:
<223> OTHER INFORMATION: Synthetic construct

<400> SEQUENCE: 262
atttcttctt cttctagctc tact                                          24

<210> SEQ ID NO 263
<211> LENGTH: 24
<212> TYPE: DNA
<213> ORGANISM: Artificial Sequence
<220> FEATURE:
<223> OTHER INFORMATION: Synthetic construct

<400> SEQUENCE: 263
atttattctt attctagcta tact                                          24

<210> SEQ ID NO 264
<211> LENGTH: 24
<212> TYPE: DNA
<213> ORGANISM: Artificial Sequence
<220> FEATURE:
<223> OTHER INFORMATION: Synthetic construct

<400> SEQUENCE: 264
atttcttctt cttctagctc tact                                          24

<210> SEQ ID NO 265
<211> LENGTH: 24
<212> TYPE: DNA
<213> ORGANISM: Artificial Sequence
<220> FEATURE:
<223> OTHER INFORMATION: Synthetic construct

<400> SEQUENCE: 265
atttatcctt attctagcta tact                                          24

<210> SEQ ID NO 266
<211> LENGTH: 24
<212> TYPE: DNA
<213> ORGANISM: Artificial Sequence
<220> FEATURE:
<223> OTHER INFORMATION: Synthetic construct

<400> SEQUENCE: 266
atttcttctt cttatggcta tact                                          24

<210> SEQ ID NO 267
<211> LENGTH: 24
<212> TYPE: DNA
<213> ORGANISM: Artificial Sequence
<220> FEATURE:
<223> OTHER INFORMATION: Synthetic construct

<400> SEQUENCE: 267
atttattctt cttatagcta tact                                          24

<210> SEQ ID NO 268
<211> LENGTH: 24
<212> TYPE: DNA
<213> ORGANISM: Artificial Sequence
<220> FEATURE:
<223> OTHER INFORMATION: Synthetic construct
```

-continued

```
<400> SEQUENCE: 268
atttcttctt cttatggcta tact                                       24

<210> SEQ ID NO 269
<211> LENGTH: 24
<212> TYPE: DNA
<213> ORGANISM: Artificial Sequence
<220> FEATURE:
<223> OTHER INFORMATION: Synthetic construct

<400> SEQUENCE: 269
atttcttctt attctggctc tact                                       24

<210> SEQ ID NO 270
<211> LENGTH: 24
<212> TYPE: DNA
<213> ORGANISM: Artificial Sequence
<220> FEATURE:
<223> OTHER INFORMATION: Synthetic construct

<400> SEQUENCE: 270
atttatcctt cttatagcta tact                                       24

<210> SEQ ID NO 271
<211> LENGTH: 24
<212> TYPE: DNA
<213> ORGANISM: Artificial Sequence
<220> FEATURE:
<223> OTHER INFORMATION: Synthetic construct

<400> SEQUENCE: 271
atttcttctt cttctggcta tact                                       24

<210> SEQ ID NO 272
<211> LENGTH: 24
<212> TYPE: DNA
<213> ORGANISM: Artificial Sequence
<220> FEATURE:
<223> OTHER INFORMATION: Synthetic construct

<400> SEQUENCE: 272
atttattctt cttctagctc tact                                       24

<210> SEQ ID NO 273
<211> LENGTH: 24
<212> TYPE: DNA
<213> ORGANISM: Artificial Sequence
<220> FEATURE:
<223> OTHER INFORMATION: Synthetic construct

<400> SEQUENCE: 273
atttatcctt attctggcta tact                                       24

<210> SEQ ID NO 274
<211> LENGTH: 24
<212> TYPE: DNA
<213> ORGANISM: Artificial Sequence
<220> FEATURE:
<223> OTHER INFORMATION: Synthetic construct

<400> SEQUENCE: 274
atttcttctt cttctggcta tact                                       24

<210> SEQ ID NO 275
```

```
<211> LENGTH: 24
<212> TYPE: DNA
<213> ORGANISM: Artificial Sequence
<220> FEATURE:
<223> OTHER INFORMATION: Synthetic construct

<400> SEQUENCE: 275
atttatcctt attctagctc tact                                           24

<210> SEQ ID NO 276
<211> LENGTH: 24
<212> TYPE: DNA
<213> ORGANISM: Artificial Sequence
<220> FEATURE:
<223> OTHER INFORMATION: Synthetic construct

<400> SEQUENCE: 276
atttatcctt cttctagctc tact                                           24

<210> SEQ ID NO 277
<211> LENGTH: 24
<212> TYPE: DNA
<213> ORGANISM: Artificial Sequence
<220> FEATURE:
<223> OTHER INFORMATION: Synthetic construct

<400> SEQUENCE: 277
atttattctt cttatggcta tact                                           24

<210> SEQ ID NO 278
<211> LENGTH: 24
<212> TYPE: DNA
<213> ORGANISM: Artificial Sequence
<220> FEATURE:
<223> OTHER INFORMATION: Synthetic construct

<400> SEQUENCE: 278
atttatcctt cttatagcta tact                                           24

<210> SEQ ID NO 279
<211> LENGTH: 24
<212> TYPE: DNA
<213> ORGANISM: Artificial Sequence
<220> FEATURE:
<223> OTHER INFORMATION: Synthetic construct

<400> SEQUENCE: 279
atttcttctt cttatggcta tact                                           24

<210> SEQ ID NO 280
<211> LENGTH: 24
<212> TYPE: DNA
<213> ORGANISM: Artificial Sequence
<220> FEATURE:
<223> OTHER INFORMATION: Synthetic construct

<400> SEQUENCE: 280
atttattctt cttatagctc tact                                           24

<210> SEQ ID NO 281
<211> LENGTH: 24
<212> TYPE: DNA
<213> ORGANISM: Artificial Sequence
<220> FEATURE:
<223> OTHER INFORMATION: Synthetic construct

<400> SEQUENCE: 281
```

```
atttattctt cttctggctc tact                                 24

<210> SEQ ID NO 282
<211> LENGTH: 24
<212> TYPE: DNA
<213> ORGANISM: Artificial Sequence
<220> FEATURE:
<223> OTHER INFORMATION: Synthetic construct

<400> SEQUENCE: 282
atttatcctt cttctggctc tact                                 24

<210> SEQ ID NO 283
<211> LENGTH: 24
<212> TYPE: DNA
<213> ORGANISM: Artificial Sequence
<220> FEATURE:
<223> OTHER INFORMATION: Synthetic construct

<400> SEQUENCE: 283
atttatcctt cttctggctc tact                                 24

<210> SEQ ID NO 284
<211> LENGTH: 24
<212> TYPE: DNA
<213> ORGANISM: Artificial Sequence
<220> FEATURE:
<223> OTHER INFORMATION: Synthetic construct

<400> SEQUENCE: 284
atttctcctt attctggcta tact                                 24

<210> SEQ ID NO 285
<211> LENGTH: 24
<212> TYPE: DNA
<213> ORGANISM: Artificial Sequence
<220> FEATURE:
<223> OTHER INFORMATION: Synthetic construct

<400> SEQUENCE: 285
atttattctt cttctggctc tact                                 24

<210> SEQ ID NO 286
<211> LENGTH: 24
<212> TYPE: DNA
<213> ORGANISM: Artificial Sequence
<220> FEATURE:
<223> OTHER INFORMATION: Synthetic construct

<400> SEQUENCE: 286
atttattctt attatagctc tact                                 24

<210> SEQ ID NO 287
<211> LENGTH: 24
<212> TYPE: DNA
<213> ORGANISM: Artificial Sequence
<220> FEATURE:
<223> OTHER INFORMATION: Synthetic construct

<400> SEQUENCE: 287
atttatcctt cttatggctc tact                                 24

<210> SEQ ID NO 288
<211> LENGTH: 24
<212> TYPE: DNA
```

-continued

```
<213> ORGANISM: Artificial Sequence
<220> FEATURE:
<223> OTHER INFORMATION: Synthetic construct

<400> SEQUENCE: 288
atttatcctt cttctagctc tact                                          24

<210> SEQ ID NO 289
<211> LENGTH: 24
<212> TYPE: DNA
<213> ORGANISM: Artificial Sequence
<220> FEATURE:
<223> OTHER INFORMATION: Synthetic construct

<400> SEQUENCE: 289
atttatcctt cttatggcta tact                                          24

<210> SEQ ID NO 290
<211> LENGTH: 24
<212> TYPE: DNA
<213> ORGANISM: Artificial Sequence
<220> FEATURE:
<223> OTHER INFORMATION: Synthetic construct

<400> SEQUENCE: 290
atttatcctt cttatagctc tact                                          24

<210> SEQ ID NO 291
<211> LENGTH: 24
<212> TYPE: DNA
<213> ORGANISM: Artificial Sequence
<220> FEATURE:
<223> OTHER INFORMATION: Synthetic construct

<400> SEQUENCE: 291
atttatcctt cttctagctc tact                                          24

<210> SEQ ID NO 292
<211> LENGTH: 24
<212> TYPE: DNA
<213> ORGANISM: Artificial Sequnence
<220> FEATURE:
<223> OTHER INFORMATION: Synthetic construct

<400> SEQUENCE: 292
atttatcctt attctggctc tact                                          24

<210> SEQ ID NO 293
<211> LENGTH: 24
<212> TYPE: DNA
<213> ORGANISM: Artificial Sequence
<220> FEATURE:
<223> OTHER INFORMATION: Synthetic construct

<400> SEQUENCE: 293
atttctcctt attctggctc tact                                          24

<210> SEQ ID NO 294
<211> LENGTH: 24
<212> TYPE: DNA
<213> ORGANISM: Artificial Sequence
<220> FEATURE:
<223> OTHER INFORMATION: Synthetic construct

<400> SEQUENCE: 294
atttattctt cttatagctc tact                                          24
```

<210> SEQ ID NO 295
<211> LENGTH: 24
<212> TYPE: DNA
<213> ORGANISM: Artificial Sequence
<220> FEATURE:
<223> OTHER INFORMATION: Synthetic construct

<400> SEQUENCE: 295
atttattctt cttatggcta tact                                             24

<210> SEQ ID NO 296
<211> LENGTH: 24
<212> TYPE: DNA
<213> ORGANISM: Artificial Sequence
<220> FEATURE:
<223> OTHER INFORMATION: Synthetic construct

<400> SEQUENCE: 296
atttattctt cttctggctc tact                                             24

<210> SEQ ID NO 297
<211> LENGTH: 24
<212> TYPE: DNA
<213> ORGANISM: Artificial Sequence
<220> FEATURE:
<223> OTHER INFORMATION: Synthetic construct

<400> SEQUENCE: 297
atttatcctt cttctggctc tact                                             24

<210> SEQ ID NO 298
<211> LENGTH: 24
<212> TYPE: DNA
<213> ORGANISM: Artificial Sequence
<220> FEATURE:
<223> OTHER INFORMATION: Synthetic construct

<400> SEQUENCE: 298
atttattctt cttctggctc tact                                             24

<210> SEQ ID NO 299
<211> LENGTH: 27
<212> TYPE: DNA
<213> ORGANISM: Artificial Sequence
<220> FEATURE:
<223> OTHER INFORMATION: Synthetic construct

<400> SEQUENCE: 299
gctcgcgctg tttggggttt ggactac                                          27

<210> SEQ ID NO 300
<211> LENGTH: 21
<212> TYPE: DNA
<213> ORGANISM: Artificial Sequence
<220> FEATURE:
<223> OTHER INFORMATION: Synthetic construct

<400> SEQUENCE: 300
gctcgcggtg ctttggacta c                                                21

<210> SEQ ID NO 301
<211> LENGTH: 21
<212> TYPE: DNA
<213> ORGANISM: Artificial Sequence
<220> FEATURE:

-continued

<223> OTHER INFORMATION: Synthetic construct

<400> SEQUENCE: 301
gctcgcggtg ctttggacta c                                                 21

<210> SEQ ID NO 302
<211> LENGTH: 45
<212> TYPE: DNA
<213> ORGANISM: Artificial Sequence
<220> FEATURE:
<223> OTHER INFORMATION: Synthetic construct

<400> SEQUENCE: 302
gctcgctctt ggtactactg gtctccgtct tctggtatgg actac                       45

<210> SEQ ID NO 303
<211> LENGTH: 21
<212> TYPE: DNA
<213> ORGANISM: Artificial Sequence
<220> FEATURE:
<223> OTHER INFORMATION: Synthetic construct

<400> SEQUENCE: 303
gctcgcggtg ctttggacta c                                                 21

<210> SEQ ID NO 304
<211> LENGTH: 21
<212> TYPE: DNA
<213> ORGANISM: Artificial Sequence
<220> FEATURE:
<223> OTHER INFORMATION: Synthetic construct

<400> SEQUENCE: 304
gctcgcggtg ctattgacta c                                                 21

<210> SEQ ID NO 305
<211> LENGTH: 33
<212> TYPE: DNA
<213> ORGANISM: Artificial Sequence
<220> FEATURE:
<223> OTHER INFORMATION: Synthetic construct

<400> SEQUENCE: 305
gctcgctctt ggtacgcttg ggctatggac tac                                    33

<210> SEQ ID NO 306
<211> LENGTH: 27
<212> TYPE: DNA
<213> ORGANISM: Artificial Sequence
<220> FEATURE:
<223> OTHER INFORMATION: Synthetic construct

<400> SEQUENCE: 306
gctcgctctg gttacgcttt ggactac                                           27

<210> SEQ ID NO 307
<211> LENGTH: 57
<212> TYPE: DNA
<213> ORGANISM: Artificial Sequence
<220> FEATURE:
<223> OTHER INFORMATION: Synthetic construct

<400> SEQUENCE: 307
gctcgcactg ttcgtggatc caaaaaaccg tacttctctg gttgggctat ggactac         57

-continued

<210> SEQ ID NO 308
<211> LENGTH: 48
<212> TYPE: DNA
<213> ORGANISM: Artificial Sequence
<220> FEATURE:
<223> OTHER INFORMATION: Synthetic construct

<400> SEQUENCE: 308
gctcgctctt cttggggtgc ttacattgtt tcttacggtt ttgactac                48

<210> SEQ ID NO 309
<211> LENGTH: 39
<212> TYPE: DNA
<213> ORGANISM: Artificial Sequence
<220> FEATURE:
<223> OTHER INFORMATION: Synthetic construct

<400> SEQUENCE: 309
gctcgcgctt actacggtca tttccatgct atggactac                39

<210> SEQ ID NO 310
<211> LENGTH: 57
<212> TYPE: DNA
<213> ORGANISM: Artificial Sequence
<220> FEATURE:
<223> OTHER INFORMATION: Synthetic construct

<400> SEQUENCE: 310
gctcgcactg ttcgtggatc caaaaaaccg tacttctctg gttgggctat ggactac                57

<210> SEQ ID NO 311
<211> LENGTH: 21
<212> TYPE: DNA
<213> ORGANISM: Artificial Sequence
<220> FEATURE:
<223> OTHER INFORMATION: Synthetic construct

<400> SEQUENCE: 311
gctcgcggtg ctatggacta c                21

<210> SEQ ID NO 312
<211> LENGTH: 33
<212> TYPE: DNA
<213> ORGANISM: Artificial Sequence
<220> FEATURE:
<223> OTHER INFORMATION: Synthetic construct

<400> SEQUENCE: 312
gctcgctact tctggtggta cggttttgac tac                33

<210> SEQ ID NO 313
<211> LENGTH: 57
<212> TYPE: DNA
<213> ORGANISM: Artificial Sequence
<220> FEATURE:
<223> OTHER INFORMATION: Synthetic construct

<400> SEQUENCE: 313
gctcgcactg ttcgtggatc caaaaaaccg tacttctctg gttgggctat ggactac                57

<210> SEQ ID NO 314
<211> LENGTH: 30
<212> TYPE: DNA
<213> ORGANISM: Artificial Sequence
<220> FEATURE:
<223> OTHER INFORMATION: Synthetic construct -continued

<400> SEQUENCE: 314
gctcgctacg gttactacgg tttggactac                                    30

<210> SEQ ID NO 315
<211> LENGTH: 21
<212> TYPE: DNA
<213> ORGANISM: Artificial Sequence
<220> FEATURE:
<223> OTHER INFORMATION: Synthetic construct

<400> SEQUENCE: 315
gctcgcggtg ctatggacta c                                             21

<210> SEQ ID NO 316
<211> LENGTH: 45
<212> TYPE: DNA
<213> ORGANISM: Artificial Sequence
<220> FEATURE:
<223> OTHER INFORMATION: Synthetic construct

<400> SEQUENCE: 316
gctcgcggtt accattacta cccgtactac tctggtttgg actac                   45

<210> SEQ ID NO 317
<211> LENGTH: 30
<212> TYPE: DNA
<213> ORGANISM: Artificial Sequence
<220> FEATURE:
<223> OTHER INFORMATION: Synthetic construct

<400> SEQUENCE: 317
gctcgctacg gttactacgg tatggactac                                    30

<210> SEQ ID NO 318
<211> LENGTH: 48
<212> TYPE: DNA
<213> ORGANISM: Artificial Sequence
<220> FEATURE:
<223> OTHER INFORMATION: Synthetic construct

<400> SEQUENCE: 318
gctcgcgctg tttggtacta ctggtgggtt tggggtggtt ttgactac                48

<210> SEQ ID NO 319
<211> LENGTH: 30
<212> TYPE: DNA
<213> ORGANISM: Artificial Sequence
<220> FEATURE:
<223> OTHER INFORMATION: Synthetic construct

<400> SEQUENCE: 319
gctcgcttcg gttactgggc tattgactac                                    30

<210> SEQ ID NO 320
<211> LENGTH: 21
<212> TYPE: DNA
<213> ORGANISM: Artificial Sequence
<220> FEATURE:
<223> OTHER INFORMATION: Synthetic construct

<400> SEQUENCE: 320
gctcgcggtg ctattgacta c                                             21

<210> SEQ ID NO 321
<211> LENGTH: 21

-continued

```
<212> TYPE: DNA
<213> ORGANISM: Artificial Sequence
<220> FEATURE:
<223> OTHER INFORMATION: Synthetic construct

<400> SEQUENCE: 321
gctcgcggtg gtatggacta c                                                      21

<210> SEQ ID NO 322
<211> LENGTH: 21
<212> TYPE: DNA
<213> ORGANISM: Artificial Sequence
<220> FEATURE:
<223> OTHER INFORMATION: Synthetic construct

<400> SEQUENCE: 322
gctcgcggtg ctatggacta c                                                      21

<210> SEQ ID NO 323
<211> LENGTH: 57
<212> TYPE: DNA
<213> ORGANISM: Artificial Sequence
<220> FEATURE:
<223> OTHER INFORMATION: Synthetic construct

<400> SEQUENCE: 323
gctcgcactg ttcgtggatc caaaaaaccg tacttctctg gttgggctat ggactac       57

<210> SEQ ID NO 324
<211> LENGTH: 21
<212> TYPE: DNA
<213> ORGANISM: Artificial Sequence
<220> FEATURE:
<223> OTHER INFORMATION: Synthetic construct

<400> SEQUENCE: 324
gctcgcggtg ctatggacta c                                                      21

<210> SEQ ID NO 325
<211> LENGTH: 21
<212> TYPE: DNA
<213> ORGANISM: Artificial Sequence
<220> FEATURE:
<223> OTHER INFORMATION: Synthetic construct

<400> SEQUENCE: 325
gctcgcggtg ctttggacta c                                                      21

<210> SEQ ID NO 326
<211> LENGTH: 30
<212> TYPE: DNA
<213> ORGANISM: Artificial Sequence
<220> FEATURE:
<223> OTHER INFORMATION: Synthetic construct

<400> SEQUENCE: 326
gctcgctacg gttacttcgg tttggactac                                             30

<210> SEQ ID NO 327
<211> LENGTH: 21
<212> TYPE: DNA
<213> ORGANISM: Artificial Sequence
<220> FEATURE:
<223> OTHER INFORMATION: Synthetic construct

<400> SEQUENCE: 327
```

-continued gctcgcggtg gtttggacta c                                                              21

<210> SEQ ID NO 328
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (29)..(29)
<223> OTHER INFORMATION: n is a, c, g, or t

<400> SEQUENCE: 328
gctcgctacg gttactacgg ttttgactna c                                                   31

<210> SEQ ID NO 329
<211> LENGTH: 24
<212> TYPE: DNA
<213> ORGANISM: Artificial Sequence
<220> FEATURE:
<223> OTHER INFORMATION: Synthetic construct

<400> SEQUENCE: 329
gctcgctact acgctatgga ctac                                                           24

<210> SEQ ID NO 330
<211> LENGTH: 21
<212> TYPE: DNA
<213> ORGANISM: Artificial Sequence
<220> FEATURE:
<223> OTHER INFORMATION: Synthetic construct

<400> SEQUENCE: 330
gctcgcggtg ctatggacta c                                                              21

<210> SEQ ID NO 331
<211> LENGTH: 21
<212> TYPE: DNA
<213> ORGANISM: Artificial Sequence
<220> FEATURE:
<223> OTHER INFORMATION: Synthetic construct

<400> SEQUENCE: 331
gctcgcggtg ctttggacta c                                                              21

<210> SEQ ID NO 332
<211> LENGTH: 66
<212> TYPE: DNA
<213> ORGANISM: Artificial Sequence
<220> FEATURE:
<223> OTHER INFORMATION: Synthetic construct

<400> SEQUENCE: 332
gctcgcggtt cttactggta cgttggtggt ggttggtggg tttctggtca tggtggtatg    60
gactac                                                               66

<210> SEQ ID NO 333
<211> LENGTH: 21
<212> TYPE: DNA
<213> ORGANISM: Artificial Sequence
<220> FEATURE:
<223> OTHER INFORMATION: Synthetic construct

<400> SEQUENCE: 333
gctcgcggtg ctttggacta c                                                              21

```
<210> SEQ ID NO 334
<211> LENGTH: 57
<212> TYPE: DNA
<213> ORGANISM: Artificial Sequence
<220> FEATURE:
<223> OTHER INFORMATION: Synthetic construct

<400> SEQUENCE: 334
gctcgcactg ttcgtggatc caaaaaaccg tacttctctg gttgggctat ggactac        57

<210> SEQ ID NO 335
<211> LENGTH: 21
<212> TYPE: DNA
<213> ORGANISM: Artificial Sequence
<220> FEATURE:
<223> OTHER INFORMATION: Synthetic construct

<400> SEQUENCE: 335
gctcgcggtg ctattgacta c                                               21

<210> SEQ ID NO 336
<211> LENGTH: 21
<212> TYPE: DNA
<213> ORGANISM: Artificial Sequence
<220> FEATURE:
<223> OTHER INFORMATION: Synthetic construct

<400> SEQUENCE: 336
gctcgcgctg cttttgacta c                                               21

<210> SEQ ID NO 337
<211> LENGTH: 21
<212> TYPE: DNA
<213> ORGANISM: Artificial Sequence
<220> FEATURE:
<223> OTHER INFORMATION: Synthetic construct

<400> SEQUENCE: 337
gctcgcgctg ctatggacta c                                               21

<210> SEQ ID NO 338
<211> LENGTH: 217
<212> TYPE: PRT
<213> ORGANISM: Artificial Sequence
<220> FEATURE:
<223> OTHER INFORMATION: Synthetic construct

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Tyr Ser Ser Gly His
                85                  90                  95

Val Leu Ile Thr Phe Gly Gln Gly Thr Lys Val Glu Ile Lys Arg Thr
            100                 105                 110
```

-continued

```
Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

```
<210> SEQ ID NO 339
<211> LENGTH: 659
<212> TYPE: DNA
<213> ORGANISM: Artificial Sequence
<220> FEATURE:
<223> OTHER INFORMATION: Synthetic construct

<400> SEQUENCE: 339
gatatccaga tgacccagtc cccgagctcc ctgtccgcct ctgtgggcga tagggtcacc      60
atcacctgcc gtgccagtca gtccgtgtcc agcgctgtag cctggtatca acagaaacca     120
ggaaaagctc cgaagcttct gatttactcg gcatccagcc tctactctac tctggagtcc     180
cttctcgctt ctctggtagc cgttccggga cggatttcac tctgaccatc agcagtctgc     240
agccggaaga cttcgcaact tattactgtc agcagcaatg gtactcttct ggtcatgttc     300
tgatcacgtt cggacagggt accaaggtgg agatcaaacg tacggtggct gcaccatctg     360
tcttcatctt cccgccatct gatgagcagt tgaaatctgg aactgcctct gttgtgtgcc     420
tgctgaataa cttctatccc agagaggcca agtacagtg gaaggtggat aacgccctcc      480
aatcgggtaa ctcccaggag agtgtcacag agcaggacag caaggacagc acctacagcc     540
tcagcagcac cctgacgctg agcaaagcag actacgagaa acacaaagtc tacgcctgcg     600
aagtcaccca tcagggcctg agctcgcccg tcacaaagag cttcaacagg ggagagtgt      659
```

```
<210> SEQ ID NO 340
<211> LENGTH: 444
<212> TYPE: PRT
<213> ORGANISM: Artificial Sequence
<220> FEATURE:
<223> OTHER INFORMATION: Synthetic construct

<400> SEQUENCE: 340

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Asn Ile Ser Tyr Ser
            20                  25                  30

Tyr Ile His Trp Val Arg Gln Ala Pro Gly Lys Gly Leu Glu Trp Val
        35                  40                  45

Ala Ser Ile Tyr Ser Ser Ser Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                85                  90                  95

Ala Arg Gly Ala Ile Asp Tyr Trp Gly Gln Gly Thr Leu Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440
```

```
<210> SEQ ID NO 341
<211> LENGTH: 1343
<212> TYPE: DNA
<213> ORGANISM: Artificial Sequence
<220> FEATURE:
<223> OTHER INFORMATION: Synthetic construct

<400> SEQUENCE: 341
```

```
gaggttcagc tggtggagtc tggcggtggc ctggtgcagc caggggggctc actccgtttg        60 tcctgtgcag cttctggctt caacggcttc aacatctctt attcttatat ctgggtgcgt       120
caggccccgg gtaagggcct ggaatgggtt tctatttatt cttcttctgg ctctactctg       180
ccgatagcgt caagggccgt ttcactataa gcgcagacac atccaaaaac acagcctacc       240
tacaaatgaa cagcttaaga gctgaggaca ctgccgtcta ttattgtgct cgcgctcgcg       300
gtgctattga ctacgactac tggggtcaag gaaccctggt caccgtctcc tcggctagca       360
ccaagggccc atcggtcttc cccctggcac cctcctccaa gagcacctct ggggggcacag      420 cggccctggg ctgcctggtc aaggactact ccccgaacc ggtgacggtg tcgtggaact       480
caggcgccct gaccagcggc gtgcacacct cccggctgt cctacagtcc tcaggactct       540
actccctcag cagcgtggtg accgtgccct ccagcagctt gggcacccag acctacatct      600
gcaacgtgaa tcacaagccc agcaacacca aggtggacaa gaaagttgag cccaaatctt       660
gtgacaaaac tcacacatgc ccaccgtgcc cagcacctga actcctgggg ggaccgtcag       720
tcttcctctt ccccccaaaa cccaaggaca cctcatgat ctcccggacc cctgaggtca       780
catgcgtggt ggtggacgtg agccacgaag accctgaggt caagttcaac tggtacgtgg       840
acggcgtgga ggtgcataat gccaagacaa agccgcggga ggagcagtac aacagcacgt       900
accgtgtggt cagcgtcctc accgtcctgc accaggactg gctgaatggc aaggagtaca       960
agtgcaaggt ctccaacaaa gccctcccag cccccatcga gaaaaccatc tccaaagcca      1020
aagggcagcc ccgagaacca caggtgtaca ccctgccccc atcccgggag gagatgacca      1080
agaaccaggt cagcctgacc tgcctggtca aaggcttcta tcccagcgac atcgccgtgg      1140
agtgggagag caatgggcag ccggagaaca actacaagac cacgcctccc gtgctggact      1200
ccgacggctc cttcttcctc tacagcaagc tcaccgtgga caagagcagg tggcagcagg      1260
ggaacgtctt ctcatgctcc gtgatgcatg aggctctgca caaccactac acgcagaaga      1320
gcctctccct gtctccgggt aaa                                              1343
```

```
<210> SEQ ID NO 342
<211> LENGTH: 24
<212> TYPE: DNA
<213> ORGANISM: Artificial Sequence
<220> FEATURE:
<223> OTHER INFORMATION: Synthetic construct

<400> SEQUENCE: 342
agggcctatt tcccatgatt cctt                                              24

<210> SEQ ID NO 343
<211> LENGTH: 20
<212> TYPE: DNA
<213> ORGANISM: Artificial Sequence
<220> FEATURE:
<223> OTHER INFORMATION: Synthetic construct

<400> SEQUENCE: 343
tcaaaaaagc accgactcgg                                                   20

<210> SEQ ID NO 344
<211> LENGTH: 90
<212> TYPE: DNA
<213> ORGANISM: Artificial Sequence
<220> FEATURE:
<223> OTHER INFORMATION: Synthetic construct

<400> SEQUENCE: 344
```

-continued

```
aatgatacgg cgaccaccga gatctacact atagcctaca ctctttccct acacgacgct    60
cttccgatct tgtggaagga cgaggtaccg                                    90

<210> SEQ ID NO 345
<211> LENGTH: 90
<212> TYPE: DNA
<213> ORGANISM: Artificial Sequence
<220> FEATURE:
<223> OTHER INFORMATION: Synthetic construct

<400> SEQUENCE: 345
aatgatacgg cgaccaccga gatctacaca tagaggcaca ctctttccct acacgacgct    60
cttccgatct tgtggaagga cgaggtaccg                                    90

<210> SEQ ID NO 346
<211> LENGTH: 90
<212> TYPE: DNA
<213> ORGANISM: Artificial Sequence
<220> FEATURE:
<223> OTHER INFORMATION: Synthetic construct

<400> SEQUENCE: 346
aatgatacgg cgaccaccga gatctacacc ctatcctaca ctctttccct acacgacgct    60
cttccgatct tgtggaagga cgaggtaccg                                    90

<210> SEQ ID NO 347
<211> LENGTH: 90
<212> TYPE: DNA
<213> ORGANISM: Artificial Sequence
<220> FEATURE:
<223> OTHER INFORMATION: Synthetic construct

<400> SEQUENCE: 347
aatgatacgg cgaccaccga gatctacacg gctctgaaca ctctttccct acacgacgct    60
cttccgatct tgtggaagga cgaggtaccg                                    90

<210> SEQ ID NO 348
<211> LENGTH: 96
<212> TYPE: DNA
<213> ORGANISM: Artificial Sequence
<220> FEATURE:
<223> OTHER INFORMATION: Synthetic construct

<400> SEQUENCE: 348
caagcagaag acggcatacg agatcgagta atgtgactgg agttcagacg tgtgctcttc    60
cgatctattt taacttgcta tttctagctc taaaac                            96

<210> SEQ ID NO 349
<211> LENGTH: 96
<212> TYPE: DNA
<213> ORGANISM: Artificial Sequence
<220> FEATURE:
<223> OTHER INFORMATION: Synthetic construct

<400> SEQUENCE: 349
caagcagaag acggcatacg agattctccg gagtgactgg agttcagacg tgtgctcttc    60
cgatctattt taacttgcta tttctagctc taaaac                            96

<210> SEQ ID NO 350
<211> LENGTH: 96
<212> TYPE: DNA
```

<213> ORGANISM: Artificial Sequence
<220> FEATURE:
<223> OTHER INFORMATION: Synthetic construct

<400> SEQUENCE: 350
caagcagaag acggcatacg agataatgag cggtgactgg agttcagacg tgtgctcttc        60
cgatctattt taacttgcta tttctagctc taaaac                                  96

<210> SEQ ID NO 351
<211> LENGTH: 96
<212> TYPE: DNA
<213> ORGANISM: Artificial Sequence
<220> FEATURE:
<223> OTHER INFORMATION: Synthetic construct

<400> SEQUENCE: 351
caagcagaag acggcatacg agatggaatc tcgtgactgg agttcagacg tgtgctcttc        60
cgatctattt taacttgcta tttctagctc taaaac                                  96

<210> SEQ ID NO 352
<211> LENGTH: 26
<212> TYPE: PRT
<213> ORGANISM: Homo sapiens

<400> SEQUENCE: 352

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 353
<211> LENGTH: 17
<212> TYPE: PRT
<213> ORGANISM: Homo sapiens

<400> SEQUENCE: 353

Val Ala Trp Tyr Gln Gln Lys Pro Gly Lys Ala Pro Lys Leu Leu Ile
1               5                   10                  15

Tyr

<210> SEQ ID NO 354
<211> LENGTH: 36
<212> TYPE: PRT
<213> ORGANISM: Homo sapiens

<400> SEQUENCE: 354

Ser Leu Tyr Ser Gly Val Pro Ser Arg Phe Ser Gly Ser Arg Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 355
<211> LENGTH: 10
<212> TYPE: PRT
<213> ORGANISM: Homo sapiens

<400> SEQUENCE: 355

Phe Gly Gln Gly Thr Lys Val Glu Ile Lys
1               5                   10

<210> SEQ ID NO 356
<211> LENGTH: 78
<212> TYPE: DNA
<213> ORGANISM: Homo sapiens

<400> SEQUENCE: 356
gatatccaga tgacccagtc cccgagctcc ctgtccgcct ctgtgggcga tagggtcacc          60
atcacctgcc gtgccagt                                                       78

<210> SEQ ID NO 357
<211> LENGTH: 51
<212> TYPE: DNA
<213> ORGANISM: Homo sapiens

<400> SEQUENCE: 357
gtagcctggt atcaacagaa accaggaaaa gctccgaagc ttctgattta c                  51

<210> SEQ ID NO 358
<211> LENGTH: 116
<212> TYPE: DNA
<213> ORGANISM: Homo sapiens

<400> SEQUENCE: 358
agcctctact ctactctgga gtcccttctc gcttctctgg tagccgttcc gggacggatt          60
tcactctgac catcagcagt ctgcagccgg aagacttcgc aacttattac tgtcag            116

<210> SEQ ID NO 359
<211> LENGTH: 30
<212> TYPE: DNA
<213> ORGANISM: Homo sapiens

<400> SEQUENCE: 359
ttcggacagg gtaccaaggt ggagatcaaa                                          30

<210> SEQ ID NO 360
<211> LENGTH: 25
<212> TYPE: PRT
<213> ORGANISM: Homo sapiens

<400> SEQUENCE: 360

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 361
<211> LENGTH: 15
<212> TYPE: PRT
<213> ORGANISM: Homo sapiens

<400> SEQUENCE: 361

His Trp Val Arg Gln Ala Pro Gly Lys Gly Leu Glu Trp Val Ala
1               5                   10                  15

<210> SEQ ID NO 362
<211> LENGTH: 37
<212> TYPE: PRT
<213> ORGANISM: Homo sapiens

<400> SEQUENCE: 362

Tyr Ala Asp Ser Val Lys Gly Arg Phe Thr Ile Ser Ala Asp Thr Ser
1               5                   10                  15

```
Lys Asn Thr Ala Tyr Leu Gln Met Asn Ser Leu Arg Ala Glu Asp Thr
            20                  25                  30

Ala Val Tyr Tyr Cys
        35

<210> SEQ ID NO 363
<211> LENGTH: 11
<212> TYPE: PRT
<213> ORGANISM: Homo sapiens

<400> SEQUENCE: 363

Trp Gly Gln Gly Thr Leu Val Thr Val Ser Ser
1               5                   10

<210> SEQ ID NO 364
<211> LENGTH: 84
<212> TYPE: DNA
<213> ORGANISM: Homo sapiens

<400> SEQUENCE: 364
gaggttcagc tggtggagtc tggcggtggc ctggtgcagc caggggggctc actccgtttg        60 tcctgtgcag cttctggctt caac                                               84

<210> SEQ ID NO 365
<211> LENGTH: 39
<212> TYPE: DNA
<213> ORGANISM: Homo sapiens

<400> SEQUENCE: 365
tgggtgcgtc aggccccggg taagggcctg gaatgggtt                                39

<210> SEQ ID NO 366
<211> LENGTH: 114
<212> TYPE: DNA
<213> ORGANISM: Homo sapiens

<400> SEQUENCE: 366
gccgatagcg tcaagggccg tttcactata agcgcagaca catccaaaaa cacagcctac        60
ctacaaatga acagcttaag agctgaggac actgccgtct attattgtgc tcgc             114

<210> SEQ ID NO 367
<211> LENGTH: 39
<212> TYPE: DNA
<213> ORGANISM: Homo sapiens

<400> SEQUENCE: 367
gactactggg gtcaaggaac cctggtcacc gtctcctcg                                39

<210> SEQ ID NO 368
<211> LENGTH: 141
<212> TYPE: PRT
<213> ORGANISM: Homo sapiens

<400> SEQUENCE: 368

Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
            20                  25                  30

Thr Gln Asp Glu Ala Gly Leu Glu Val His Gln Phe Trp Pro Leu Val
        35                  40                  45
```

```
Glu Ile Gln Cys Ser Pro Asp Leu Arg Phe Phe Leu Cys Ser Met Tyr
    50                  55                  60

Thr Pro Ile Cys Leu Pro Asp Tyr His Lys Pro Leu Pro Pro Cys Arg
65                  70                  75                  80

Ser Val Cys Glu Arg Ala Lys Ala Gly Cys Ser Pro Leu Met Arg Gln
                85                  90                  95

Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg Ser Glu
            115                 120                 125

Ala Thr Thr Ala Pro Pro Arg Pro Phe Pro Ala Lys Pro
    130                 135                 140
```

<210> SEQ ID NO 369
<211> LENGTH: 127
<212> TYPE: PRT
<213> ORGANISM: Homo sapiens

<400> SEQUENCE: 369

```
Asp His Gly Tyr Cys Gln Pro Ile Ser Ile Pro Leu Cys Thr Asp Ile
1               5                   10                  15

Ala Tyr Asn Gln Thr Ile Met Pro Asn Leu Leu Gly His Thr Asn Gln
                20                  25                  30

Glu Asp Ala Gly Leu Glu Val His Gln Phe Tyr Pro Leu Val Lys Val
            35                  40                  45

Gln Cys Ser Ala Glu Leu Lys Phe Phe Leu Cys Ser Met Tyr Ala Pro
    50                  55                  60

Val Cys Thr Val Leu Glu Gln Ala Leu Pro Pro Cys Arg Ser Leu Cys
65                  70                  75                  80

Glu Arg Ala Arg Gln Gly Cys Glu Ala Leu Met Asn Lys Phe Gly Phe
                85                  90                  95

Gln Trp Pro Asp Thr Leu Lys Cys Glu Lys Phe Pro Val His Gly Ala
            100                 105                 110

Gly Glu Leu Cys Val Gly Gln Asn Thr Ser Asp Lys Gly Thr Pro
            115                 120                 125
```

<210> SEQ ID NO 370
<211> LENGTH: 127
<212> TYPE: PRT
<213> ORGANISM: Homo sapiens

<400> SEQUENCE: 370

```
Asp His Gly Phe Cys Gln Pro Ile Ser Ile Pro Leu Cys Thr Asp Ile
1               5                   10                  15

Ala Tyr Asn Gln Thr Ile Met Pro Asn Leu Leu Gly His Thr Asn Gln
                20                  25                  30

Glu Asp Ala Gly Leu Glu Val His Gln Phe Tyr Pro Leu Val Lys Val
            35                  40                  45

Gln Cys Ser Pro Glu Leu Arg Phe Phe Leu Cys Ser Met Tyr Ala Pro
    50                  55                  60

Val Cys Thr Val Leu Glu Gln Ala Ile Pro Pro Cys Arg Ser Ile Cys
65                  70                  75                  80

Glu Arg Ala Arg Gln Gly Cys Glu Ala Leu Met Asn Lys Phe Gly Phe
                85                  90                  95

Gln Trp Pro Glu Arg Leu Arg Cys Glu His Phe Pro Arg His Gly Ala
            100                 105                 110
```

-continued

```
Glu Gln Ile Cys Val Gly Gln Asn His Ser Glu Asp Gly Ala Pro
    115                 120                 125

<210> SEQ ID NO 371
<211> LENGTH: 126
<212> TYPE: PRT
<213> ORGANISM: Homo sapiens

<400> SEQUENCE: 371

Glu Arg Arg Cys Asp Pro Ile Arg Ile Ser Met Cys Gln Asn Leu Gly
1               5                   10                  15

Tyr Asn Val Thr Lys Met Pro Asn Leu Val Gly His Glu Leu Gln Thr
            20                  25                  30

Asp Ala Glu Leu Gln Leu Thr Thr Phe Thr Pro Leu Ile Gln Tyr Gly
        35                  40                  45

Cys Ser Ser Gln Leu Gln Phe Phe Leu Cys Ser Val Tyr Val Pro Met
    50                  55                  60

Cys Thr Glu Lys Ile Asn Ile Pro Ile Gly Pro Cys Gly Gly Met Cys
65                  70                  75                  80

Leu Ser Val Lys Arg Arg Cys Glu Pro Val Leu Lys Glu Phe Gly Phe
                85                  90                  95

Ala Trp Pro Glu Ser Leu Asn Cys Ser Lys Phe Pro Pro Gln Asn Asp
            100                 105                 110

His Asn His Met Cys Met Glu Gly Pro Gly Asp Glu Glu Val
        115                 120                 125

<210> SEQ ID NO 372
<211> LENGTH: 128
<212> TYPE: PRT
<213> ORGANISM: Homo sapiens

<400> SEQUENCE: 372

Lys Ala Pro Val Cys Gln Glu Ile Thr Val Pro Met Cys Arg Gly Ile
1               5                   10                  15

Gly Tyr Asn Leu Thr His Met Pro Asn Gln Phe Asn His Asp Thr Gln
            20                  25                  30

Asp Glu Ala Gly Leu Glu Val His Gln Phe Trp Pro Leu Val Glu Ile
        35                  40                  45

Gln Cys Ser Pro Asp Leu Arg Phe Phe Leu Cys Ser Met Tyr Thr Pro
    50                  55                  60

Ile Cys Leu Pro Asp Tyr His Lys Pro Leu Pro Pro Cys Arg Ser Val
65                  70                  75                  80

Cys Glu Arg Ala Lys Ala Gly Cys Ser Pro Leu Met Arg Gln Tyr Gly
                85                  90                  95

Phe Ala Trp Pro Glu Arg Met Ser Cys Asp Arg Leu Pro Val Leu Gly
            100                 105                 110

Arg Asp Ala Glu Val Leu Cys Met Asp Tyr Asn Arg Ser Glu Ala Thr
        115                 120                 125

<210> SEQ ID NO 373
<211> LENGTH: 127
<212> TYPE: PRT
<213> ORGANISM: Homo sapiens

<400> SEQUENCE: 373

Ser Leu Phe Thr Cys Glu Pro Ile Thr Val Pro Arg Cys Met Lys Met
1               5                   10                  15

Ala Tyr Asn Met Thr Phe Phe Pro Asn Leu Met Gly His Tyr Asp Gln
```

```
                20              25              30

Ser Ile Ala Ala Val Glu Met Glu His Phe Leu Pro Leu Ala Asn Leu
            35              40              45

Glu Cys Ser Pro Asn Ile Glu Thr Phe Leu Cys Lys Ala Phe Val Pro
        50              55              60

Thr Cys Ile Glu Gln Ile His Val Val Pro Pro Cys Arg Lys Leu Cys
65              70              75              80

Glu Lys Val Tyr Ser Asp Cys Lys Lys Leu Ile Asp Thr Phe Gly Ile
                85              90              95

Arg Trp Pro Glu Glu Leu Glu Cys Asp Arg Leu Gln Tyr Cys Asp Glu
                100             105             110

Thr Val Pro Val Thr Phe Asp Pro His Thr Glu Phe Leu Gly Pro
                115             120             125

<210> SEQ ID NO 374
<211> LENGTH: 125
<212> TYPE: PRT
<213> ORGANISM: Homo sapiens

<400> SEQUENCE: 374

Asp His Gly Phe Cys Gln Pro Ile Ser Ile Pro Leu Cys Thr Asp Ile
1               5               10              15

Ala Tyr Asn Gln Thr Ile Leu Pro Asn Leu Leu Gly His Thr Asn Gln
                20              25              30

Glu Asp Ala Gly Leu Glu Val His Gln Phe Tyr Pro Leu Val Lys Val
            35              40              45

Gln Cys Ser Pro Glu Leu Arg Phe Phe Leu Cys Ser Met Tyr Ala Pro
        50              55              60

Val Cys Thr Val Leu Asp Gln Ala Ile Pro Pro Cys Arg Ser Leu Cys
65              70              75              80

Glu Arg Ala Arg Gln Gly Cys Glu Ala Leu Met Asn Lys Phe Gly Phe
                85              90              95

Gln Trp Pro Glu Arg Leu Arg Cys Glu Asn Phe Pro Val His Gly Ala
                100             105             110

Gly Glu Ile Cys Val Gly Gln Asn Thr Ser Asp Gly Ser
            115             120             125

<210> SEQ ID NO 375
<211> LENGTH: 125
<212> TYPE: PRT
<213> ORGANISM: Homo sapiens

<400> SEQUENCE: 375

Lys Glu Leu Ala Cys Gln Glu Ile Thr Val Pro Leu Cys Lys Gly Ile
1               5               10              15

Gly Tyr Asn Tyr Thr Tyr Met Pro Asn Gln Phe Asn His Asp Thr Gln
                20              25              30

Asp Glu Ala Gly Leu Glu Val His Gln Phe Trp Pro Leu Val Glu Ile
            35              40              45

Gln Cys Ser Pro Asp Leu Lys Phe Phe Leu Cys Ser Met Tyr Thr Pro
        50              55              60

Ile Cys Leu Glu Asp Tyr Lys Lys Pro Leu Pro Pro Cys Arg Ser Val
65              70              75              80

Cys Glu Arg Ala Lys Ala Gly Cys Ala Pro Leu Met Arg Gln Tyr Gly
                85              90              95

Phe Ala Trp Pro Asp Arg Met Arg Cys Asp Arg Leu Pro Glu Gln Gly
```

```
                100                 105                 110

Asn Pro Asp Thr Leu Cys Met Asp Tyr Asn Arg Thr Asp
        115                 120                 125

<210> SEQ ID NO 376
<211> LENGTH: 127
<212> TYPE: PRT
<213> ORGANISM: Homo sapiens

<400> SEQUENCE: 376

Gly Ala Ala Pro Cys Gln Ala Val Glu Ile Pro Met Cys Arg Gly Ile
1               5                   10                  15

Gly Tyr Asn Leu Thr Arg Met Pro Asn Leu Leu Gly His Thr Ser Gln
            20                  25                  30

Gly Glu Ala Ala Ala Glu Leu Ala Glu Phe Ala Pro Leu Val Gln Tyr
        35                  40                  45

Gly Cys His Ser His Leu Arg Phe Phe Leu Cys Ser Leu Tyr Ala Pro
    50                  55                  60

Met Cys Thr Asp Gln Val Ser Thr Pro Ile Pro Ala Cys Arg Pro Met
65                  70                  75                  80

Cys Glu Gln Ala Arg Leu Arg Cys Ala Pro Ile Met Glu Gln Phe Asn
                85                  90                  95

Phe Gly Trp Pro Asp Ser Leu Asp Cys Ala Arg Leu Pro Thr Arg Asn
            100                 105                 110

Asp Pro His Ala Leu Cys Met Glu Ala Pro Glu Asn Ala Thr Ala
        115                 120                 125

<210> SEQ ID NO 377
<211> LENGTH: 127
<212> TYPE: PRT
<213> ORGANISM: Homo sapiens

<400> SEQUENCE: 377

Gly Asp Gly Lys Cys Gln Pro Ile Glu Ile Pro Met Cys Lys Asp Ile
1               5                   10                  15

Gly Tyr Asn Met Thr Arg Met Pro Asn Leu Met Gly His Glu Asn Gln
            20                  25                  30

Arg Glu Ala Ala Ile Gln Leu His Glu Phe Ala Pro Leu Val Glu Tyr
        35                  40                  45

Gly Cys His Gly His Leu Arg Phe Phe Leu Cys Ser Leu Tyr Ala Pro
    50                  55                  60

Met Cys Thr Glu Gln Val Ser Thr Pro Ile Pro Ala Cys Arg Val Met
65                  70                  75                  80

Cys Glu Gln Ala Arg Leu Lys Cys Ser Pro Ile Met Glu Gln Phe Asn
                85                  90                  95

Phe Lys Trp Pro Asp Ser Leu Asp Cys Arg Lys Leu Pro Asn Lys Asn
            100                 105                 110

Asp Pro Asn Tyr Leu Cys Met Glu Ala Pro Asn Asn Gly Ser Asp
        115                 120                 125
```